US006753167B2

(12) United States Patent
Moloney et al.

(10) Patent No.: US 6,753,167 B2
(45) Date of Patent: *Jun. 22, 2004

(54) PREPARATION OF HETEROLOGOUS PROTEINS ON OIL BODIES

(75) Inventors: Maurice M. Moloney, Calgary (CA); Gijs van Rooijen, Calgary (CA)

(73) Assignee: SemBioSys Genetics Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/893,525

(22) Filed: Jun. 29, 2001

(65) Prior Publication Data

US 2003/0126631 A1 Jul. 3, 2003

Related U.S. Application Data

(63) Continuation-in-part of application No. 09/210,843, filed on Dec. 18, 1998, now Pat. No. 6,288,304, which is a continuation-in-part of application No. 08/846,021, filed on Apr. 25, 1997, now Pat. No. 5,948,682, which is a continuation-in-part of application No. 08/366,783, filed on Dec. 30, 1994, now Pat. No. 5,650,554, which is a continuation-in-part of application No. 08/142,418, filed on Nov. 16, 1993, now abandoned, which is a continuation-in-part of application No. 07/659,835, filed on Feb. 22, 1991, now abandoned.

(51) Int. Cl.[7] .......................... C12N 15/62; C12N 15/12; C12N 15/29; C12N 15/82; A01H 5/00
(52) U.S. Cl. ...................... 435/69.8; 800/278; 800/288; 800/306; 800/312; 800/314; 800/320.1; 800/320; 800/322; 435/69.7; 435/69.2; 435/69.4; 435/69.52; 435/69.6; 435/200; 435/419; 435/468; 536/23.2; 536/23.4; 536/23.5; 536/23.51; 536/23.53; 536/23.6
(58) Field of Search ................................. 800/278, 288, 800/306, 322, 312, 314, 320.1, 320; 536/23.6, 23.2, 23.4, 23.5, 23.51, 23.53; 435/468, 419, 69.7, 69.8, 69.2, 69.4, 69.52, 69.6, 200

(56) References Cited

U.S. PATENT DOCUMENTS 5,650,554 A 7/1997 Moloney et al. ............ 800/205

FOREIGN PATENT DOCUMENTS

EP 0193259 9/1986

OTHER PUBLICATIONS

Radke et al., "Transformation of *Brassica napus* L. using *Agrobacterium tumefaciens*: Developmentally Regulated Expression of a Reintroduced Napin Gene", Theor. Appln. Genet. (1988) 75:685–694.
Taylor et al., "Storage–protein Regulation and Lipid Accumulation in Microspore embryos of *Brassica napus* L.", Planta (1990) 181:18–26.
Sijmons et al., "Production of Correctly Processed Human Serum Albumin in Transgenic Plants" Bio/Technology (1990) 8:217–221.
Huang, "Lipid Bodies" Modern Methods Plant Analysis (1985) 1:145–151.
Misra and Gedamu, "Heavy Metal Tolerant Transgenic *Brassica napus* L. and *Nicotiana tabacum* L. Plants" Theor. Appl. Genet. (1989) 78:161–168.
Hatzopoulos et al., "Interaction of Nuclear Factors with Upstream Sequences of Lipid Body Membrane Protein Gene from Carrot" The Plant Cell (1990) 2:457–467.
Lee et al., "Maize Oleosin is Correctly Targeted to Seed Oil Bodies in *Brassica napus* Transformed with the Maize Olesin Gene" PNAS USA (1991) 88:6181–6185.
Vance and Huang, "Expression of Lipid Body Protein Gene during Maize Seed Development" J. Biol. Chem. (1988) 263:1476–1481.
Vance and Huang, "The Major Protein from Lipid Bodies of Maize" J. Biol. Chem. (1987) 262:11275–11279.
Qu and Huang, "Oleosin KD 18 on the Surface of Oil Bodies in Maize" J. Biol. Chem (1990) 265:2238–2243.
Sengupta–Gopalan et al., "Developmentally Regulated Expression of the Bean Beta–phaseolin Gene in Tobacco Seed" PNAS USA (1985) 82:3320–3324.
Fraley et al., "Expression of Bacterial Genes in Plant Cells" PNAS USA (1983) 80:4803–4807.
Vanderkerckhove et al., "Enkephalins Produced in transgenic Plants using Modified 2S Seed Storage Proteins" BIO/Technology (1989) 7:929–932.
Murphy et al., "Synthesis of the Major Oil–body Membrane Protein in Developing Rapeseed (*Brassica napus*) Embryos" Biochem J. (1989) 258:285–293.
Qu et al., "Characterisitics and Biosynthesis of Membrane Proteins of Lipid Bodies in the Scutella of Maize (*Zea mays* L.)" Biochem. J. (1986) 235:57–65.

(List continued on next page.)

*Primary Examiner*—David T. Fox
(74) *Attorney, Agent, or Firm*—Bereskin & Parr; Micheline Gravelle

(57) ABSTRACT

The present invention relates to the use of a class of genes called oil body protein genes that have unique features. The discovery of these features allowed the invention of methods for the production of recombinant proteins wherein a protein of interest can be easily separated from other host cell components. The invention is further exemplified by methods for exploitation of the unique characteristics of the oil body proteins and oil body genes for expression of polypeptides of interest in many organisms, particularly plant seeds. Said polypeptides may include but are not limited to: seed storage proteins, enzymes, bioactive peptides, antibodies and the like. The invention can also be modified to recover recombinant polypeptides fused to oil body proteins from non-plant host cells. Additionally the invention provides a method of using recombinant proteins associated with seed oil bodies released during seed germination for expression of polypeptides that afford protection to seedlings from pathogens. Finally, the persistent association of oil body proteins with the oil body can be further utilized to develop a biological means to create novel immobilized enzymes useful for bioconversion of substrates.

29 Claims, 20 Drawing Sheets

OTHER PUBLICATIONS

Josefsson et al., "Structure of a Gene Encoding the 1.7 S Storage Protein Napin, from *Brassica napus*" J. Biol. Chem (1987) 262:12196–12201.

Scofield and Crouch, "Nucleotide Sequence of A Member of the Napin Storage Protein Family From *Brassica napus*"J. Biol. Chem. (1987) 262:12202–12208.

Fujikawa et al., "Bovine Factor X1 (Stuart Factor), Mechanism of Activation by a Protein from Russell's Viper Venom" Biochemistry (1972) 11:4892–4899.

Nagai et al., "Oxygen Binding Properties of Human Mutant Hemoglobins Synthesized in *Escherichia coli*" PNAS USA (1985) 82:7252–7255.

Scholtissek and Grosse, "A Plasmid Vector System for the Expression of a Triprotein Consisting of Beta–galactosidase, a Collagenase Recognition Site and a Foreign Gene Product" Gene (1988) 62:55–64.

Bevan, "Binary Agrobacterium Vectors for Plant Transformation" Nucl. Acids. Res. (1984) 12:8711–8721.

Murphy et al., "A class of Amphipathic Proteins Associated with Lipid Storage Bodies in Plants" Biochem. Biophys. Acta (1991) 1088:86–94.

Antoni et al., "A Short Synthetic Peptide Fragment of Human Interleukin 1 with Immunostimulatory But not Inflammatory Activity" J. Immunol. (1986) 137:3201–3204.

An et al., "New Cloning Vehicles for Transformation of Higher Plants" Embo J. (1985) 4:277–284.

Hood et al., "The Hypervirulence of *Agrobacterium tumefaciens* A281 is encoded in a Region of pTiBo542 outside of T–DNA" J. Bacteriol. (1986) 168:1291–1301.

Holbrook et al., "Oilbody Proteins in Microspore–derived Embryos of *Brassica napus*" Plant Physiol. (1991) 97:1051–1058.

Kalinski et al., "Molecular Cloning of a Protein Associated with Soybean Seed Oil Bodies that is Similar to Thiol Proteases of the Papain Family" J. Biol. Chem. (1990) 265:13843–13848.

Bosch et al., "A trout growth hormone is expressed, correctly folded and partially glycosylated in the leaves but not the seeds of transgenic plants" Transgenic Research (1994) 3:304–310.

Chen, Jeff C.F. et al., "Cloning and Secondary Structure Analysis of Caleosin, a Unique Calcium–Binding Protein in Oil Bodies of Plant Seeds", *Plant Cell Physiol.* 40 (10), 1079–1086 (1999).

Naested, Henrich, et al., "Caleosin: $Ca^{2+}$–binding proteins associated with lipid bodies", *Plant Molecular Biology*, 44:463–476, 2000.

Nuccio, Michael L. and Terry L. Thomas, "ATS1 and ATS3: two novel embryo–specific genes in Arabidopsis thaliana", *Plant Molecular Biology* 39:1153–1163, 1999.

FIGURE 2

```
         NcoI
-867 CCATGGCTATACCCAACCTCGGTCTTGGTCACACCAGGAACTCTCTGGTAAGCTAGCTCCACTCCCCAGAAACAACCGGCGCCAAATTGC

-777 CGGAATTGCTGACCTGAAGACGGAACATCATCGTCGGGTCCTTGGGCGATTGCGGCGGAAGATGGGTCAGCTTGGGCTTGAGGACGAGAC

-687 CCGAATCGAGTCTGTTGAAAGGTTGTTCATTGGGATTTGTATACGGAGATTGGTCGTCGAGAGGTTTGAGGGAAAGGACAAATGGGTTTG
                                                            R1
-597 GCTCTGGAGAAAGAGAGTGCGGCTTTAGAGAGAGAATTGAGAGGTTTAGAGAGAGATGCGGCGGCGATGACGGGAGGAGAGACGACGAGG
                      R2                     R2
-507 ACCTGCATTATCAAAGCAGTGACGTGGTGAAATTTGGAACTTTTAAGAGGCAGATAGATTTATTATTTGTATCCATTTTCTTCATTGTTC
                                           R1
-417 TAGAATGTCGCGGAACAAATTTTAAAACTAAATCCTAAATTTTTCTAATTTTGTTGCCAATAGTGGATATGTGGGCCGTATAGAAGGAAT

-327 CTATTGAAGGCCCAAACCCATACTGACGAGCCCAAAGGTTCGTTTTGCGTTTTATGTTTCGGTTCGATGCCAACGCCACATTCTGAGCTA
                I
-237 GGCAAAAAACAAACGTGTCTTTGAATAGACTCCTCTCGTTAACACATGCAGCGGCTGCATGGTGACGCCATTAACACGTGGCCTACAATT

-147 GCATGATGTCTCCATTGACACGTGACTTCTCGTCTCCTTTCTTAATATATCTAACAAACACTCCTACCTCTTCCAAAATATATACACATC
                                                              M A D T A R G T H H D
 -57 TTTTTCATCAATCTCTCATTCAAAATCTCATTCTCTCTAGTAAACAAGAACAAAAAAATGGCGGATACAGCTAGAGGAACCCATCACGAT
          I I G R D Q Y P M M G R D R D Q Y Q M S G R G S D Y S K S R
  34 ATCATCGGCAGAGACCAGTACCCGATGATGGGCCGAGACCGAGACCAGTACCAGATGTCCGGACGAGGATCTGACTACTCCAAGTCTAGG
        Q I A K A A T A V T A G G S L L V L S S L T L V G T V I A L
 124 CAGATTGCTAAAGCTGCAACTGCTGTCACAGCTGGTGGTTCCCTCCTTGTTCTCTCCAGCCTTACCCTTGTTGGAACTGTCATAGCTTTG
       T V A T P L L V I F S P I L V P A L I T V A L L I T G F L S
 214 ACTGTTGCAACACCTCTGCTCGTTATCTTCAGCCCAATCCTTGTCCCGGCTCTCATCACAGTTGCACTCCTCATCACCGGTTTTCTTTCC
      S G G F G I A A I T V F S W I Y K
 304 TCTGGAGGGTTTGGCATTGCCGCTATAACCGTTTTCTCTTGGATTTACAAgtaagcacacatttatcatcttacttcataattttgtgca 394 atatgtgcatgcatgtgttgagccagtagctttggatcaattttttggtcgaataacaaatgtaacaataagaaattgcaaattctagg 484 gaacatttggttaactaaatacgaaatttgacctagctagcttgaatgtgtctgtgtatatcatctatataggtaaaatgcttggtatga
                                Y A T G E H P Q G S D K L D S A R M K L G S K
 574 tacctattgattgtgaataggTACGCAACGGGAGAGCACCCACAGGGATCAGACAAGTTGGACAGTGCAAGGATGAAGTTGGGAAGCAAA
         A Q D L K D R A Q Y Y G Q Q H T G G E H D R D R T R G G Q H
 664 GCTCAGGATCTGAAAGACAGAGCTCAGTACTACGGACAGCAACATACTGGTGGGGAACATGACCGTGACCGTACTCGTGGTGGCCAGCAC
       T T *
 754 ACTACTTAAGTTACCCCACTGATGTCATCGTCATAGTCCAATAACTCCAATGTCGGGGAGTTAGTTTATGAGGAATAAAGTGTTTAGAAT
                                                                                   KpnI
 844 TTGATCAGGGGGAGATAATAAAAGCCGAGTTTGAATCTTTTTGTTATAAGTAATGTTTATGTGTGTTTCTATATGTTGTCAAATGGTACC
```

FIGURE 4

```
  1 ATG GCG GAT ACA GCT AGA ACC CAT CAC GAT GTC ACA AGT CGA GAT CAG TAT CCC CGA GAC  60
  1 M   A   D   T   A   R   T   H   H   D   V   T   S   R   D   Q   Y   P   R   D    20

61 CGA GAC CAG TAT TCT ATG ATC GGT CGA GAC CGT GAC CAG TAC TCT ATG ATG GGC CGA GAC  120
 21 R   D   Q   Y   S   M   I   G   R   D   R   D   Q   Y   S   M   M   G   R   D    40

121 CGA GAC CAG TAC AAC ATG TAT GGT CGA GAC TAC TCC AAG TCT AGA CAG ATT GCT AAG GCT  180
 41 R   D   Q   Y   N   M   Y   G   R   D   Y   S   K   S   R   Q   I   A   K   A    60

181 GTT ACC GCA GTC ACG GCG GGT GGG TCC CTC CTT GTC CTC TCC AGT CTC ACC CTT GTT GGT  240
 61 V   T   A   V   T   A   G   G   S   L   L   V   L   S   S   L   T   L   V   G    80

241 ACT GTC ATT GCT TTG ACT GTT GCC ACT CCA CTC CTC GTT ATC TTT AGC CCA ATC CTC GTG  300
 81 T   V   I   A   L   T   V   A   T   P   L   L   V   I   F   S   P   I   L   V    100

301 CCG GCT CTC ATC ACC GTA GCA CTT CTC ATC ACT GGC TTT CTC TCC TCT GGT GGG TTT GCC  360
101 P   A   L   I   T   V   A   L   L   I   T   G   F   L   S   S   G   G   F   A    120

361 ATT GCA GCT ATA ACC GTC TTC TCC TGG ATC TAT AAG TAC GCA ACG GGA GAG CAC CCA CAG  420
121 I   A   A   I   T   V   F   S   W   I   Y   K   Y   A   T   G   E   H   P   Q    140

421 GGG TCA GAT AAG TTG GAC AGT GCA AGG ATG AAG CTG GAA ACC AAA GCT CAG GAT ATT AAA  480
141 G   S   D   K   L   D   S   A   R   M   K   L   G   T   K   A   Q   D   I   K    160

481 GAC AGA GCT CAA TAC TAC GGA CAG CAA CAT ACA GGT GGT GAG CAT GAC CGT GAC CGT ACT  540
161 D   R   A   Q   Y   Y   G   Q   Q   H   T   G   G   E   H   D   R   D   R   T    180

541 CGT GGT GGC CAG CAC ACT ACT TAA                                                   564
181 R   G   G   Q   H   T   T   *                                                     188
```

FIGURE 6A

```
HindIII
   1 ATAAGCTTGCATGCCTGCGGAACTCTCTGGTAAGCTAGCTCCACTCCCCAGAAACAACCG    60
  61 GCGCCAAATTGCCGGAATTGCTGACCTGAAGACGGAACATCATCGTCGGGTCCTTGGGCG   120
 121 ATTGCGGCGAAGATGGGTCAGCTTGGGCTTGAGGACGAGACCCGAATCGAGTCTGTTGA   180
 181 AAGGTTGTTCATTGGGATTTGTATACGGAGATTGGTCGTCGAGAGGTTTGAGGGAAAGGA   240
 241 CAAATGGGTTTGGCTCTGGAGAAAGAGAGTGCGGCTTTAGAGAGAGAATTGAGAGGTTTA   300
 301 GAGAGAGATGCGGCGGCGATGACGGGAGGAGAGACGACGAGGACCTGCATTATCAAAGCA   360
 361 GTGACGTGGTGAAATTTGGAACTTTTAAGAGGCAGATAGATTTATTATTTGTATCCATTT   420
 421 TCTTCATTGTTCTAGAATGTCGCGGAACAAATTTTAAAACTAAATCCTAAATTTTTCTAA   480
 481 TTTTGTTGCCAATAGTGGATATGTGGGCCGTATAGAAGGAATCTATTGAAGGCCCAAACC   540
 541 CATACTGACGAGCCCAAAGGTTCGTTTTGCGTTTTATGTTTCGGTTCGATGCCAACGCCA   600
 601 CATTCTGAGCTAGGCAAAAAACAAACGTGTCTTTGAATAGACTCCTCTCGTTAACACATG   660
 661 CAGCGGCTGCATGGTGACGCCATTAACACGTGGCCTACAATTGCATGATGTCTCCATTGA   720
 721 CACGTGACTTCTCGTCTCCTTTCTTAATATATCTAACAAACACTCCTACCTCTTCCAAAA   780
 781 TATATACACATCTTTTTGATCAATCTCTCATTCAAAATCTCATTCTCTCTAGTAAACAAG   840
                  M  A  D  T  A  R  G  T  H  H  D  I  I  G  R  D  Q
 841 AACAAAAAAATGGCGGATACAGCTAGAGGAACCCATCACGATATCATCGGCAGAGACCAG   900
       Y  P  M  M  G  R  D  R  D  Q  Y  Q  M  S  G  R  G  S  D  Y
 901 TACCCGATGATGGGCCGAGACCGAGACCAGTACCAGATGTCCGGACGAGGATCTGACTAC   960
       S  K  S  R  Q  I  A  K  A  A  T  A  V  T  A  G  G  S  L  L
 961 TCCAAGTCTAGGCAGATTGCTAAAGCTGCAACTGCTGTCACAGCTGGTGGTTCCCTCCTT  1020
       V  L  S  S  L  T  L  V  G  T  V  I  A  L  T  V  A  T  P  L
1021 GTTCTCTCCAGCCTTACCCTTGTTGGAACTGTCATAGCTTTGACTGTTGCAACACCTCTG  1080
       L  V  I  F  S  P  I  L  V  P  A  L  I  T  V  A  L  L  I  T
1081 CTCGTTATCTTCAGCCCAATCCTTGTCCCGGCTCTCATCACAGTTGCACTCCTCATCACC  1140
       G  F  L  S  S  G  G  F  G  I  A  A  I  T  V  F  S  W  I  Y
1141 GGTTTTCTTTCCTCTGGAGGGTTTGGCATTGCCGCTATAACCGTTTTCTCTTGGATTTAC  1200
       K
1201 AAGTAAGCACACATTTATCATCTTACTTCATAATTTTGTGCAATATGTGCATGCATGTGT  1260
1261 TGAGCCAGTAGCTTTGGATCAATTTTTTTGGTCGAATAACAAATGTAACAATAAGAAATT  1320
1321 GCAAATTCTAGGGAACATTTGGTTAACTAAATACGAAATTTGACCTAGCTAGCTTGAATG  1380
1381 TGTCTGTGTATATCATCTATATAGGTAAAATGCTTGGTATGATACCTATTGATTGTGAAT  1440
             Y  A  T  G  E  H  P  Q  G  S  D  K  L  D  S  A  R  M  K
1441 AGGTACGCAACGGGAGAGCACCCACAGGGATCAGACAAGTTGGACAGTGCAAGGATGAAG  1500
       L  G  S  K  A  Q  D  L  K  D  R  A  Q  Y  Y  G  Q  Q  H  T
1501 TTGGGAAGCAAAGCTCAGGATCTGAAAGACAGAGCTCAGTACTACGGACAGCAACATACT  1560
       G  G  E  H  D  R  D  R  T  R  G  G  Q  H  T  T  L  V  P  R
1561 GGTGGGGAACATGACCGTGACCGTACTCGTGGTGGCCAGCACACTACTCTCGTTCCACGA  1620
       G  S  M  A  E  I  T  R  I  P  L  Y  K  G  K  S  L  R  K  A
1621 GGATCCATGGCTGAGATCACCAGGATCCCTCTGTACAAAGGCAAGTCTCTGAGGAAGGCG  1680
       L  K  E  H  G  L  L  E  D  F  L  Q  K  Q  Q  Y  G  I  S  S
1681 CTGAAGGAGCATGGGCTTCTGGAGGACTTCCTGCAGAAACAGCAGTATGGCATCAGCAGC  1740
       K  Y  S  G  F  G  E  V  A  S  V  P  L  T  N  Y  L  D  S  Q
1741 AAGTACTCCGGCTTCGGGGAGGTGGCCAGCGTGCCCCTGACCAACTACCTGGATAGTCAG  1800
       Y  F  G  K  I  Y  L  G  T  P  P  Q  E  F  T  V  L  F  D  T
1801 TACTTTGGGAAGATCTACCTCGGGACCCCGCCCCAGGAGTTCACCGTGCTGTTTGACACT  1860
       G  S  S  D  F  W  V  P  S  I  Y  C  K  S  N  A  C  K  N  H
1861 GGCTCCTCTGACTTCTGGGTACCCTCTATCTACTGCAAGAGCAATGCCTGCAAAAACCAC  1920
       Q  R  F  D  P  R  K  S  S  T  F  Q  N  L  G  K  P  L  S  I
```

FIGURE 6B

```
1921 CAGCGCTTCGACCCGAGAAAGTCGTCCACCTTCCAGAACCTGGGCAAGCCCCTGTCTATC     1980
       H  Y  G  T  G  S  M  Q  G  I  L  G  Y  D  T  V  T  V  S  N
1981 CACTACGGGACAGGCAGCATGCAGGGCATCCTGGGCTATGACACCGTCACTGTCTCCAAC     2040
       I  V  D  I  Q  Q  T  V  G  L  S  T  Q  E  P  G  D  V  F  T
2041 ATTGTGGACATCCAGCAGACAGTAGGCCTGAGCACCCAGGAGCCCGGGGACGTCTTCACC     2100
       Y  A  E  F  D  G  I  L  G  M  A  Y  P  S  L  A  S  E  Y  S
2101 TATGCCGAATTCGACGGGATCCTGGGGATGGCCTACCCCTCGCTCGCCTCAGAGTACTCG     2160
       I  P  V  F  D  N  M  M  N  R  H  L  V  A  Q  D  L  F  S  V
2161 ATACCCGTGTTTGACAACATGATGAACAGGCACCTGGTGGCCCAAGACCTGTTCTCGGTT     2220
       Y  M  D  R  N  G  Q  E  S  M  L  T  L  G  A  I  D  P  S  Y
2221 TACATGGACAGGAATGGCCAGGAGAGCATGCTCACGCTGGGGGCCATCGACCCGTCCTAC     2280
       Y  T  G  S  L  H  W  V  P  V  T  V  Q  Q  Y  W  Q  F  T  V
2281 TACACAGGGTCCCTGCACTGGGTGCCCGTGACAGTGCAGCAGTACTGGCAGTTCACTGTG     2340
       D  S  V  T  I  S  G  V  V  V  A  C  E  G  G  C  Q  A  I  L
2341 GACAGTGTCACCATCAGCGGTGTGGTTGTGGCCTGTGAGGGTGGCTGTCAGGCCATCTTG     2400
       D  T  G  T  S  K  L  V  G  P  S  S  D  I  L  N  I  Q  Q  A
2401 GACACGGGCACCTCCAAGCTGGTCGGGCCCAGCAGCGACATCCTCAACATCCAGCAGGCC     2460
       I  G  A  T  Q  N  Q  Y  G  E  F  D  I  D  C  D  N  L  S  Y
2461 ATTGGAGCCACACAGAACCAGTACGGTGAGTTTGACATCGACTGCGACAACCTGAGCTAC     2520
       M  P  T  V  V  F  E  I  N  G  K  M  Y  P  L  T  P  S  A  Y
2521 ATGCCCACTGTGGTCTTTGAGATCAATGGCAAAATGTACCCACTGACCCCCTCCGCCTAT     2580
       T  S  Q  D  Q  G  F  C  T  S  G  F  Q  S  E  N  H  S  Q  K
2581 ACCAGCCAAGACCAGGGCTTCTGTACCAGTGGCTTCCAGAGTGAAAATCATTCCCAGAAA     2640
       W  I  L  G  D  V  F  I  R  E  Y  Y  S  V  F  D  R  A  N  N
2641 TGGATCCTGGGGGATGTTTTCATCCGAGAGTATTACAGCGTCTTTGACAGGGCCAACAAC     2700
       L  V  G  L  A  K  A  I  *
2701 CTCGTGGGGCTGGCCAAAGCCATCTGAAAGCTT                                2733
                                     HindIII
```

FIGURE 9

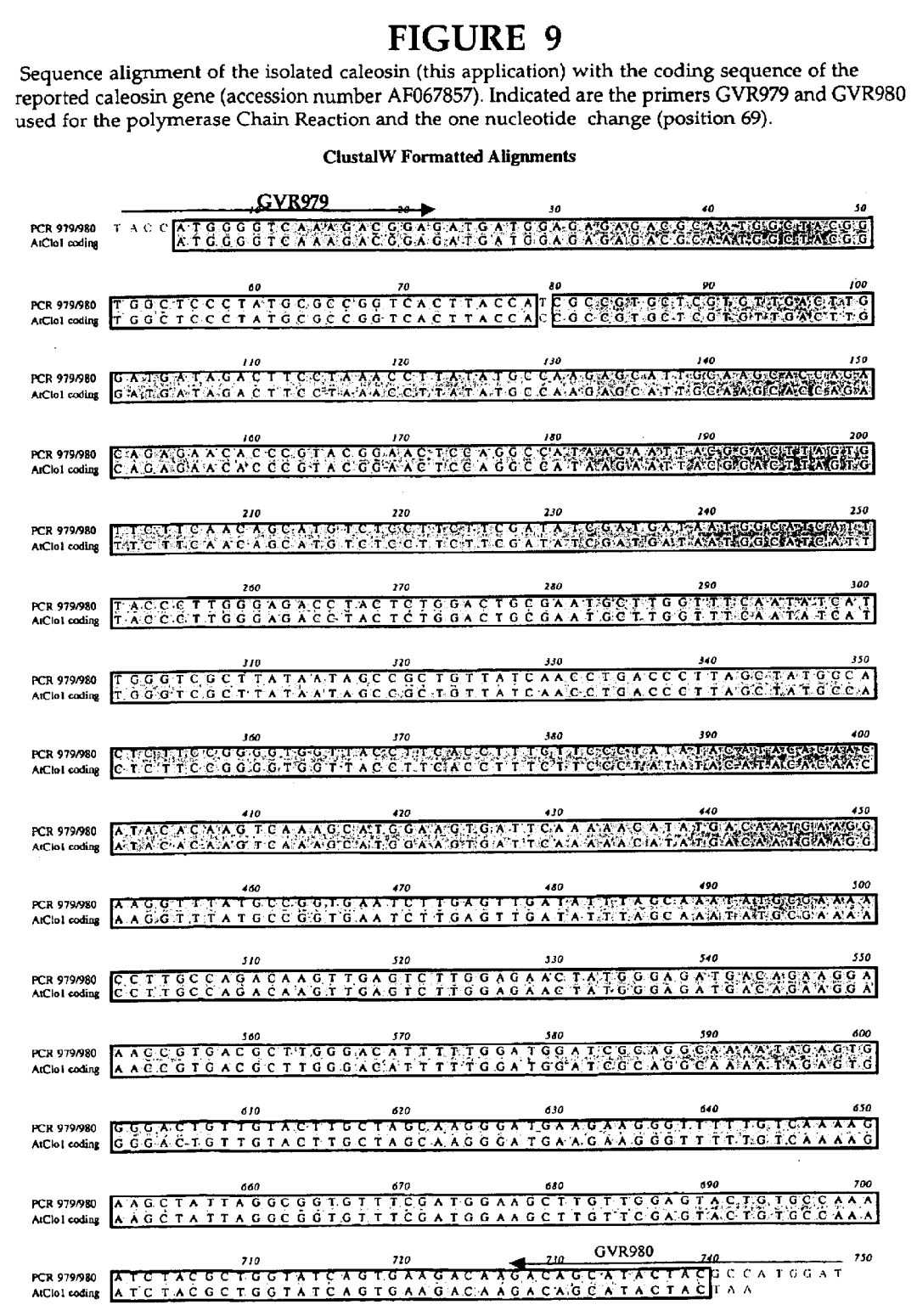

Sequence alignment of the isolated caleosin (this application) with the coding sequence of the reported caleosin gene (accession number AF067857). Indicated are the primers GVR979 and GVR980 used for the polymerase Chain Reaction and the one nucleotide change (position 69).

ClustalW Formatted Alignments

FIGURE 10A

Nucleotide sequence of insert of pSBS2098 containing the phaseolin promoter-ß Glucuronidase (GUS)-phaseolin terminator sequence. The GUS sequence and its deduced amino acid sequence is indicated in uppercase. The phaseolin promoter corresponds to nucleotide 1-1547, and the phaseolin terminator corresponds to nucleotide sequence 3426-4646. The terminator was furnished with a a KpnI site (nt 4647-4652) to facilitate cloning.

```
       EcoRI
   1 gaattcattgtactcccagtatcattatagtgaaagttttggctctctcgccggtggttttttacctctatttaaagggg   80
  81 ttttccacctaaaaattctggtatcattctcactttacttgttactttaatttctcataatctttggttgaaattatcac  160
 161 gcttccgcacacgatatccctacaaatttattatttgttaaacattttcaaaccgcataaaatttatgaagtcccgtct   240
 241 atctttaatgtagtctaacattttcatattgaaatatataatttacttaattttagcgttggtagaaagcataaagattt  320
 321 attcttattcttcttcatataaatgtttaatatacaatataaacaaattctttaccttaagaaggatttcccattttata  400
 401 ttttaaaaatatatttatcaaatattttttcaaccacgtaaatctcataataataagttgtttcaaaagtaataaaattta  480
 481 actccataatttttttattcgactgatcttaaagcaacacccagtgacacaactagccatttttttctttgaataaaaaa  560
 561 atccaattatcattgtatttttttttatacaatgaaaatttcaccaaacaatcatttgtggtatttctgaagcaagtcatg  640
 641 ttatgcaaaattctataattcccatttgacactacggaagtaactgaagatctgcttttacatgcgagacacatcttcta  720
 721 aagtaattttaataatagttactatattcaagatttcatatatcaaatactcaatattacttctaaaaaattaattagat  800
 801 ataattaaaatattacttttttaatttaagtttaattgttgaatttgtgactattgatttattattctactatgtttaa   880
 881 attgttttatagatagtttaaagtaaatataagtaatgtagtagagtgttagagtgttaccctaaaccataaactataac  960
 961 atttatggtggactaattttcatatatttcttattgcttttacctttcttggtatgtaagtccgtaactagaattacag  1040
1041 tgggttgccatgacactctgtggtcttttggttcatgcatgggtcttgcgcaagaaaaagacaaagaacaaagaaaaaag  1120
1121 acaaaacagagagacaaaacgcaatcacacaaccaactcaaattagtcactggctgatcaagatcgccgcgtccatgtat  1200
1201 gtctaaatgccatgcaaagcaacacgtgcttaacatgcactttaaatggctcacccatctcaacccacacacaaacacat  1280
1281 tgccttttcttcatcatcaccacaaccacctgtatatattcattctcttccgccacctcaatttcttcacttcaacaca   1360
1361 cgtcaacctgcatatgcgtgtcatcccatgcccaaatctccatgcatgttccaaccaccttctctcttatataataccta  1440
1441 taaatacctctaatatcactcacttctttcatcatccatccatcagagtactactactctactactataatacccaac   1520
1521 ccaactcatattcaatactactctaCC ATG GTC TTA CGT CCT GTA GAA ACC CCA ACC CGT GAA ATC  1586
   1                              M   V   L   R   P   V   E   T   P   T   R   E   I    13
1587 AAA AAA CTC GAC GGC CTG TGG GCA TTC AGT CTG GAT CGC GAA AAC TGT GGA ATT GAT CAG  1646
  14  K   K   L   D   G   L   W   A   F   S   L   D   R   E   N   C   G   I   D   Q    33
1647 CGT TGG TGG GAA AGC GCG TTA CAA GAA AGC CGG GCA ATT GCT GTG CCA GGC AGT TTT AAC  1706
  34  R   W   W   E   S   A   L   Q   E   S   R   A   I   A   V   P   G   S   F   N    53
1707 GAT CAG TTC GCC GAT GCA GAT ATT CGT AAT TAT GCG GGC AAC GTC TGG TAT CAG CGC GAA  1766
  54  D   Q   F   A   D   A   D   I   R   N   Y   A   G   N   V   W   Y   Q   R   E    73
1767 GTC TTT ATA CCG AAA GGT TGG GCA GGC CAG CGT ATC GTG CTG CGT TTC GAT GCG GTC ACT  1826
  74  V   F   I   P   K   G   W   A   G   Q   R   I   V   L   R   F   D   A   V   T    93
1827 CAT TAC GGC AAA GTG TGG GTC AAT AAT CAG GAA GTG ATG GAG CAT CAG GGC GGC TAT ACG  1886
  94  H   Y   G   K   V   W   V   N   N   Q   E   V   M   E   H   Q   G   G   Y   T   113
1887 CCA TTT GAA GCC GAT GTC ACG CCG TAT GTT ATT GCC GGG AAA AGT GTA CGT ATC ACC GTT  1946
 114  P   F   E   A   D   V   T   P   Y   V   I   A   G   K   S   V   R   I   T   V   133
1947 TGT GTG AAC AAC GAA CTG AAC TGG CAG ACT ATC CCG CCG GGA ATG GTG ATT ACC GAC GAA  2006
 134  C   V   N   N   E   L   N   W   Q   T   I   P   P   G   M   V   I   T   D   E   153
2007 AAC GGC AAG AAA AAG CAG TCT TAC TTC CAT GAT TTC TTT AAC TAT GCC GGA ATC CAT CGC  2066
 154  N   G   K   K   K   Q   S   Y   F   H   D   F   F   N   Y   A   G   I   H   R   173
2067 AGC GTA ATG CTC TAC ACC ACG CCG AAC ACC TGG GTG GAC GAT ATC ACC GTG GTG ACG CAT  2126
 174  S   V   M   L   Y   T   T   P   N   T   W   V   D   D   I   T   V   V   T   H   193
2127 GTC GCG CAA GAC TGT AAC CAC GCG TCT GTT GAC TGG CAG GTG GTG GCC AAT GGT GAT GTC  2186
 194  V   A   Q   D   C   N   H   A   S   V   D   W   Q   V   V   A   N   G   D   V   213
2187 AGC GTT GAA CTG CGT GAT GCG GAT CAA CAG GTG GTT GCA ACT GGA CAA GGC ACT AGC GGG  2246
 214  S   V   E   L   R   D   A   D   Q   Q   V   V   A   T   G   Q   G   T   S   G   233
```

FIGURE 10B

```
2247 ACT TTG CAA GTG GTG AAT CCG CAC CTC TGG CAA CCG GGT GAA GGT TAT CTC TAT GAA CTG 2306
234  T   L   Q   V   V   N   P   H   L   W   Q   P   G   E   G   Y   L   Y   E   L   253
2307 TGC GTC ACA GCC AAA AGC CAG ACA GAG TGT GAT ATC TAC CCG CTT CGC GTC GGC ATC CGG 2366
254  C   V   T   A   K   S   Q   T   E   C   D   I   Y   P   L   R   V   G   I   R   273

2367 TCA GTG GCA GTG AAG GGC CAA CAG TTC CTG ATT AAC CAC AAA CCG TTC TAC TTT ACT GGC 2426
274  S   V   A   V   K   G   Q   Q   F   L   I   N   H   K   P   F   Y   F   T   G   293
2427 TTT GGT CGT CAT GAA GAT GCG GAC TTA CGT GGC AAA GGA TTC GAT AAC GTG CTG ATG GTG 2486
294  F   G   R   H   E   D   A   D   L   R   G   K   G   F   D   N   V   L   M   V   313
2487 CAC GAC CAC GCA TTA ATG GAC TGG ATT GGG GCC AAC TCC TAC CGT ACC TCG CAT TAC CCT 2546
314  H   D   H   A   L   M   D   W   I   G   A   N   S   Y   R   T   S   H   Y   P   333
2547 TAC GCT GAA GAG ATG CTC GAC TGG GCA GAT GAA CAT GGC ATC GTG GTG ATT GAT GAA ACT 2606
334  Y   A   E   E   M   L   D   W   A   D   E   H   G   I   V   V   I   D   E   T   353
2607 GCT GCT GTC GGC TTT TCG CTC TCT TTA GGC ATT GGT TTC GAA GCG GGC AAC AAG CCG AAA 2666
354  A   A   V   G   F   S   L   S   L   G   I   G   F   E   A   G   N   K   P   K   373
2667 GAA CTG TAC AGC GAA GAG GCA GTC AAC GGG GAA ACT CAG CAA GCG CAC TTA CAG GCG ATT 2726
374  E   L   Y   S   E   E   A   V   N   G   E   T   Q   Q   A   H   L   Q   A   I   393
2727 AAA GAG CTG ATA GCG CGT GAC AAA AAC CAC CCA AGC GTG GTG ATG TGG AGT ATT GCC AAC 2786
394  K   E   L   I   A   R   D   K   N   H   P   S   V   V   M   W   S   I   A   N   413
2787 GAA CCG GAT ACC CGT CCG CAA GGT GCA CGG GAA TAT TTC GCG CCA CTG GCG GAA GCA ACG 2846
414  E   P   D   T   R   P   Q   G   A   R   E   Y   F   A   P   L   A   E   A   T   433
2847 CGT AAA CTC GAC CCG ACG CGT CCG ATC ACC TGC GTC AAT GTA ATG TTC TGC GAC GCT CAC 2906
434  R   K   L   D   P   T   R   P   I   T   C   V   N   V   M   F   C   D   A   H   453
2907 ACC GAT ACC ATC AGC GAT CTC TTT GAT GTG CTG TGC CTG AAC CGT TAT TAC GGA TGG TAT 2966
454  T   D   T   I   S   D   L   F   D   V   L   C   L   N   R   Y   Y   G   W   Y   473
2967 GTC CAA AGC GGC GAT TTG GAA ACG GCA GAG AAG GTA CTG GAA AAA GAA CTT CTG GCC TGG 3026
474  V   Q   S   G   D   L   E   T   A   E   K   V   L   E   K   E   L   L   A   W   493
3027 CAG GAG AAA CTG CAT CAA CCG ATT ATC ATC ACC GAA TAC GGC GTG GAT ACG TTA GCC GGG 3086
494  Q   E   K   L   H   Q   P   I   I   I   T   E   Y   G   V   D   T   L   A   G   513
3087 CTG CAC TCA ATG TAC ACC GAC ATG TGG AGT GAA GAG TAT CAG TGT GCA TGG CTG GAT ATG 3146
514  L   H   S   M   Y   T   D   M   W   S   E   E   Y   Q   C   A   W   L   D   M   533
3147 TAT CAC CGC GTC TTT GAT CGC GTC AGC GCC GTC GTC GGT GAA CAG GTA TGG AAT TTC GCC 3206
534  Y   H   R   V   F   D   R   V   S   A   V   V   G   E   Q   V   W   N   F   A   553
3207 GAT TTT GCG ACC TCG CAA GGC ATA TTG CGC GTT GGC GGT AAC AAG AAA GGG ATC TTC ACT 3266
554  D   F   A   T   S   Q   G   I   L   R   V   G   G   N   K   K   G   I   F   T   573
3267 CGC GAC CGC AAA CCG AAG TCG GCG GCT TTT CTG CTG CAA AAA CGC TGG ACT GGC ATG AAC 3326
574  R   D   R   K   P   K   S   A   A   F   L   L   Q   K   R   W   T   G   M   N   593
3327 TTC GGT GAA AAA CCG CAG CAG GGA GGC AAA CAA TGA ATCAACAACTCTCCTGGCGCACCATCGTCGGC 3394
594  F   G   E   K   P   Q   Q   G   G   K   Q   *                                    605
3395 TACAGCCTCGGTGGAATTCGATATCAAGCTTaaataagtatgaactaaaatgcatgtaggtgtaagagctcatggagagc 3474
3475 atggaatattgtatccgaccatgtaacagtataataactgagctccatctcacttcttctatgaataaacaaggatgtt 3554
3555 atgatatattaacactctatctatgcaccttattgttctatgataaatttcctcttattattataaatcatctgaatcgt 3634
3635 gacggcttatggaatgcttcaaatagtacaaaaacaaatgtgtactataagactttctaaacaattctaactttagcatt 3714
3715 gtgaacgagacataagtgttaagaagacataacaattataatggaagaagtttgtctccatttatatattatatattacc 3794
3795 cacttatgtattatattaggatgttaaggagacataacaattataaagagagaagtttgtatccatttatatattatata 3874
3875 ctacccatttatatattatacttatccacttatttaatgtctttataaggtttgatccatgatattctaatattttagt 3954
3955 tgatatgtatatgaaagggtactatttgaactctcttactctgtataaaggttggatcatccttaaagtgggtctattta 4034
4035 attttattgcttcttacagataaaaaaaaaattatgagttggtttgataaaatattgaaggatttaaaataataataaat 4114
4115 aataaataacatataatatatgtatataaatttattataatataacatttatctataaaaaagtaaatattgtcataaat 4194
```

FIGURE 10C

```
4195  ctatacaatcgtttagccttgctggacgactctcaattatttaaacgagagtaaacatatttgacttttggttatttaa  4274
4275  caaattattatttaacactatatgaaatttttttttttttatcggcaaggaaataaaattaaattaggagggacaatggtg  4354
4355  tgtcccaatccttatacaaccaacttccacaggaaggtcaggtcggggacaacaaaaaaacaggcaagggaaattttta  4434
4435  atttgggttgtcttgtttgctgcataatttatgcagtaaaacactacacataacccttttagcagtagagcaatggttga  4514
4515  ccgtgtgcttagcttcttttatttttattttttttatcagcaaagaataaataaaataaaatgagacacttcagggatgttt  4594
4595  caacccttatacaaaaccccaaaaacaagtttcctagcaccctaccaactaaGGTACC                         4652
```

FIGURE 11A

Nucleotide sequence of the phaseolin promoter-oleosinGUS-phaseolin terminator sequence. The oleosinGUS coding sequence and its deduced aminoacid sequence is indicated. The phaseolin promoter corresponds to nucleotide 6-1554. The sequence encoding oleosin corresponds to nt 1555-2313, the intron in this sequence (nt 1908-2147) is indicated in italics. The GUS sequence corresponds to nt 2314-4191. The phaseolin terminator corresponds to nucleotide sequence 4192-5412.

```
       PstI   EcoRI
    1  ctgcaggaattcattgtactcccagtatcattatagtgaaagttttggctctctcgccggtggttttttacctctattta    80
   81  aaggggttttccacctaaaaattctggtatcattctcacttttacttgttactttaatttctcataatctttggttgaaat   160
  161  tatcacgcttccgcacacgatatccctacaaattttattatttgttaaacattttcaaaccgcataaaatttatgaagtc   240
  241  ccgtctatctttaatgtagtctaacattttcatattgaaatatataatttacttaattttagcgttggtagaaagcataa   320
  321  tgatttattcttattcttcttcatataaatgtttaatatacaatataaacaaattctttaccttaagaaggatttcccat   400
  401  tttatattttaaaaatatatttatcaaatattttcaaccacgtaaatctcataataataagttgtttcaaaagtaataa   480
  481  aatttaactccataatttttttattcgactgatcttaaagcaacacccagtgacacaactagccattttttttctttgaat   560
  561  aaaaaatccaattatcattgtatttttttttatacaatgaaaatttcaccaaacaatcatttgtggtatttctgaagcaa   640
  641  gtcatgttatgcaaaattctataattcccatttgacactacggaagtaactgaagatctgcttttacatgcgagacacat   720
  721  cttctaaagtaattttaataatagttactatattcaagatttcatatatcaaatactcaatattacttctaaaaaattaa   800
  801  ttagatataattaaaatattactttttaattttaagtttaattgttgaatttgtgactattgatttattattctactat   880
  881  gtttaaattgttttatagatagtttaaagtaaatataagtaatgtagtagagtgttagagtgttaccctaaaccataaac   960
  961  tataagatttatggtggactaattttcatatatttcttattgcttttaccttttcttggtatgtaagtccgtaactggaa  1040
 1041  ttactgtgggttgccatggcactctgtggtcttttggttcatgcatggatgcttgcgcaagaaaaagacaaagaacaaag  1120
 1121  aaaaaagacaaaacagagagacaaaacgcaatcacacaaccaactcaaattagtcactggctgatcaagatcgccgcgtc  1200
 1201  catgtatgtctaaatgccatgcaaagcaacacgtgcttaacatgcactttaaatggctcacccatctcaacccacacaca  1280
 1281  aacacattgccttttcttcatcatcaccacaaccacctgtatatattcattctcttccgccacctcaatttcttcactt  1360
 1361  caacacacgtcaacctgcatatgcgtgtcatcccatgcccaaatctccatgcatgttccaaccacctttctctcttatata  1440
 1441  atacctataaatacctctaatatcactcacttctttcatcatccatccatccagagtactactactctactactataata  1520
 1521  ccccaacccaactcatattcaatactactctact ATG GCG GAT ACA GCT AGA GGA ACC CAT CAC GAT      1587
    1                                      M   A   D   T   A   R   G   T   H   H   D     11
 1588  ATC ATC GGC AGA GAC CAG TAC CCG ATG ATG GGC CGA GAC CGA GAC CAG TAC CAG ATG TCC    1647
   12  I   I   G   R   D   Q   Y   P   M   M   G   R   D   R   D   Q   Y   Q   M   S     31
 1648  GGA CGA GGA TCT GAC TAC TCC AAG TCT AGG CAG ATT GCT AAA GCT GCA ACT GCT GTC ACA    1707
   32  G   R   G   S   D   Y   S   K   S   R   Q   I   A   K   A   A   T   A   V   T     51
 1708  GCT GGT GGT TCC CTC CTT GTT CTC TCC AGC CTT ACC CTT GTT GGA ACT GTC ATA GCT TTG    1767
   52  A   G   G   S   L   L   V   L   S   S   L   T   L   V   G   T   V   I   A   L     71
 1768  ACT GTT GCA ACA CCT CTG CTC GTT ATC TTC AGC CCA ATC CTT GTC CCG GCT CTC ATC ACA    1827
   72  T   V   A   T   P   L   L   V   I   F   S   P   I   L   V   P   A   L   I   T     91
 1828  GTT GCA CTC CTC ATC ACC GGT TTT CTT TCC TCT GGA GGG TTT GGC ATT GCC GCT ATA ACC    1887
   92  V   A   L   L   I   T   G   F   L   S   S   G   G   F   G   I   A   A   I   T    111
 1888  GTT TTC TCT TGG ATT TAC AA gtaagcacacatttatcatcttacttcataatttgtgcaatatgtgcatgca    1960
  112  V   F   S   W   I   Y   K                                                         118
 1961  tgtgttgagccagtagcttttggatcaatttttttggtcgaataacaaatgtaacaataagaaattgcaaattctagggaa  2040
 2041  cattggttaactaaatacgaaatttgacctagctagcttgaatgtgtctgtgtatatcatctatataggtaaaatgctt  2120
 2121  ggtatgatacctattgattgtgaatag G TAC GCA ACG GGA GAG CAC CCA CAG GGA TCA GAC AAG       2184
  119                               Y   A   T   G   E   H   P   Q   G   S   D   K        130
```

FIGURE 11B

```
2185 TTG GAC AGT GCA AGG ATG AAG TTG GGA AGC AAA GCT CAG GAT CTG AAA GAC AGA GCT CAG 2244
131  L   D   S   A   R   M   K   L   G   S   K   A   Q   D   L   K   D   R   A   Q   150
2245 TAC TAC GGA CAC CAA CAT ACT GGT GGG GAA CAT GAC CGT GAC CGT ACT CGT GGT GGC CAG 2304
151  Y   Y   G   Q   Q   H   T   G   G   E   H   D   R   D   R   T   R   G   G   Q   170
2305 CAC ACT ACC ATG GTC TTA CGT CCT GTA GAA ACC CCA ACC CGT GAA ATC AAA AAA CTC GAC 2364
171  H   T   T   M   V   L   R   P   V   E   T   P   T   R   E   I   K   K   L   D   190
2365 GGC CTG TGG GCA TTC AGT CTG GAT CGC GAA AAC TGT GGA ATT GAT CAG CGT TGG TGG GAA 2424
191  G   L   W   A   F   S   L   D   R   E   N   C   G   I   D   Q   R   W   W   E   210
2425 AGC GCG TTA CAA GAA AGC CGG GCA ATT GCT GTG CCA GGC AGT TTT AAC GAT CAG TTC GCC 2484
211  S   A   L   Q   E   S   R   A   I   A   V   P   G   S   F   N   D   Q   F   A   230
2485 GAT GCA GAT ATT CGT AAT TAT GCG GGC AAC GTC TGG TAT CAG CGC GAA GTC TTT ATA CCG 2544
231  D   A   D   I   R   N   Y   A   G   N   V   W   Y   Q   R   E   V   F   I   P   250
2545 AAA GGT TGG GCA GGC CAG CGT ATC GTG CTG CGT TTC GAT GCG GTC ACT CAT TAC GGC AAA 2604
251  K   G   W   A   G   Q   R   I   V   L   R   F   D   A   V   T   H   Y   G   K   270
2605 GTG TGG GTC AAT AAT CAG GAA GTG ATG GAG CAT CAG GGC GGC TAT ACG CCA TTT GAA GCC 2664
271  V   W   V   N   N   Q   E   V   M   E   H   Q   G   G   Y   T   P   F   E   A   290
2665 GAT GTC ACG CCG TAT GTT ATT GCC GGG AAA AGT GTA CGT ATC ACC GTT TGT GTG AAC AAC 2724
291  D   V   T   P   Y   V   I   A   G   K   S   V   R   I   T   V   C   V   N   N   310
2725 GAA CTG AAC TGG CAG ACT ATC CCG CCG GGA ATG GTG ATT ACC GAC GAA AAC GGC AAG AAA 2784
311  E   L   N   W   Q   T   I   P   P   G   M   V   I   T   D   E   N   G   K   K   330
2785 AAG CAG TCT TAC TTC CAT GAT TTC TTT AAC TAT GCC GGA ATC CAT CGC AGC GTA ATG CTC 2844
331  K   Q   S   Y   F   H   D   F   F   N   Y   A   G   I   H   R   S   V   M   L   350
2845 TAC ACC ACG CCG AAC ACC TGG GTG GAC GAT ATC ACC GTG GTG ACG CAT GTC GCG CAA GAC 2904
351  Y   T   T   P   N   T   W   V   D   D   I   T   V   V   T   H   V   A   Q   D   370
2905 TGT AAC CAC GCG TCT GTT GAC TGG CAG GTG GTG GCC AAT GGT GAT GTC AGC GTT GAA CTG 2964
371  C   N   H   A   S   V   D   W   Q   V   V   A   N   G   D   V   S   V   E   L   390
2965 CGT GAT GCG GAT CAA CAG GTG GTT GCA ACT GGA CAA GGC ACT AGC GGG ACT TTG CAA GTG 3024
391  R   D   A   D   Q   Q   V   V   A   T   G   Q   G   T   S   G   T   L   Q   V   410
3025 GTG AAT CCG CAC CTC TGG CAA CCG GGT GAA GGT TAT CTC TAT GAA CTG TGC GTC ACA GCC 3084
411  V   N   P   H   L   W   Q   P   G   E   G   Y   L   Y   E   L   C   V   T   A   430
3085 AAA AGC CAG ACA GAG TGT GAT ATC TAC CCG CTT CGC GTC GGC ATC CGG TCA GTG GCA GTG 3144
431  K   S   Q   T   E   C   D   I   Y   P   L   R   V   G   I   R   S   V   A   V   450
3145 AAG GGC CAA CAG TTC CTG ATT AAC CAC AAA CCG TTC TAC TTT ACT GGC TTT GGT CGT CAT 3204
451  K   G   Q   Q   F   L   I   N   H   K   P   F   Y   F   T   G   F   G   R   H   470
3205 GAA GAT GCG GAC TTA CGT GGC AAA GGA TTC GAT AAC GTG CTG ATG GTG CAC GAC CAC GCA 3264
471  E   D   A   D   L   R   G   K   G   F   D   N   V   L   M   V   H   D   H   A   490
3265 TTA ATG GAC TGG ATT GGG GCC AAC TCC TAC CGT ACC TCG CAT TAC CCT TAC GCT GAA GAG 3324
491  L   M   D   W   I   G   A   N   S   Y   R   T   S   H   Y   P   Y   A   E   E   510
3325 ATG CTC GAC TGG GCA GAT GAA CAT GGC ATC GTG GTG ATT GAT GAA ACT GCT GCT GTC GGC 3384
511  M   L   D   W   A   D   E   H   G   I   V   V   I   D   E   T   A   A   V   G   530
3385 TTT TCG CTC TCT TTA GGC ATT GGT TTC GAA GCG GGC AAC AAG CCG AAA GAA CTG TAC AGC 3444
531  F   S   L   S   L   G   I   G   F   E   A   G   N   K   P   K   E   L   Y   S   550
3445 GAA GAG GCA GTC AAC GGG GAA ACT CAG CAA GCG CAC TTA CAG GCG ATT AAA GAG CTG ATA 3504
551  E   E   A   V   N   G   E   T   Q   Q   A   H   L   Q   A   I   K   E   L   I   570
3505 GCG CGT GAC AAA AAC CAC CCA AGC GTG GTG ATG TGG AGT ATT GCC AAC GAA CCG GAT ACC 3564
571  A   R   D   K   N   H   P   S   V   V   M   W   S   I   A   N   E   P   D   T   590
```

FIGURE 11C

```
3565 CGT CCG CAA GGT GCA CGG GAA TAT TTC GCG CCA CTG GCG GAA GCA ACG CGT AAA CTC GAC  3624
 591  R   P   Q   G   A   R   E   Y   F   A   P   L   A   E   A   T   R   K   L   D    610
3625 CCG ACG CGT CCG ATC ACC TGC GTC AAT GTA ATG TTC TGC GAC GCT CAC ACC GAT ACC ATC  3684
 611  P   T   R   P   I   T   C   V   N   V   M   F   C   D   A   H   T   D   T   I    630
3685 AGC GAT CTC TTT GAT GTG CTG TGC CTG AAC CGT TAT TAC GGA TGG TAT GTC CAA AGC GGC  3744
 631  S   D   L   F   D   V   L   C   L   N   R   Y   Y   G   W   Y   V   Q   S   G    650
3745 GAT TTG GAA ACG GCA GAG AAG GTA CTG GAA AAA GAA CTT CTG GCC TGG CAG GAG AAA CTG  3804
 651  D   L   E   T   A   E   K   V   L   E   K   E   L   L   A   W   Q   E   K   L    670
3805 CAT CAG CCG ATT ATC ATC ACC GAA TAC GGC GTG GAT ACG TTA GCC GGG CTG CAC TCA ATG  3864
 671  H   Q   P   I   I   I   T   E   Y   G   V   D   T   L   A   G   L   H   S   M    690
3865 TAC ACC GAC ATG TGG AGT GAA GAG TAT CAG TGT GCA TGG CTG GAT ATG TAT CAC CGC GTC  3924
 691  Y   T   D   M   W   S   E   E   Y   Q   C   A   W   L   D   M   Y   H   R   V    710
3925 TTT GAT CGC GTC AGC GCC GTC GGT GAA CAG GTA TGG AAT TTC GCC GAT TTT GCG ACC  3984
 711  F   D   R   V   S   A   V   V   G   E   Q   V   W   N   F   A   D   F   A   T    730
3985 TCG CAA GGC ATA TTG CGC GTT GGC GGT AAC AAG AAA GGG ATC TTC ACT CGC GAC CGC AAA  4044
 731  S   Q   G   I   L   R   V   G   G   N   K   K   G   I   F   T   R   D   R   K    750
4045 CCG AAG TCG GCG GCT TTT CTG CTG CAA AAA CGC TGG ACT GGC ATG AAC TTC GGT GAA AAA  4104
 751  P   K   S   A   A   F   L   L   Q   K   R   W   T   G   M   N   F   G   E   K    770
4105 CCG CAG CAG GGA GGC AAA CAA TGA ATCAACAACTCTCCTGGCGCACCATCGTCGGCTACAGCCTCGGTGAA  4176
 771  P   Q   Q   G   G   K   Q   *                                                    778
4177 TTCGATATCAAGCTTaaataagtatgaactaaaatgcatgtaggtgtaagagctcatggagagcatggaatattgtatcc  4256
4257 gaccatgtaacagtataataactgagctccatctcacttcttctatgaataaacaaaggatgttatgatatattaacact  4336
4337 ctatctatgcacccttattgttctatgataaatttcctcttattattataaatcatctgaatcgtgacggcttatggaatg  4416
4417 cttcaaatagtacaaaaacaaatgtgtactataagactttctaaacaattctaactttagcattgtgaacgagacataag  4496
4497 tgttaagaagacataacaattataatggaagaagtttgtctccatttatatattatatattacccacttatgtattatat  4576
4577 taggatgttaaggagacataacaattataaagagagaagtttgtatccatttatatattatatactacccatttatatat  4656
4657 tatacttatccacttatttaatgtcttttataaggtttgatccatgatatttctaatatttagttgatatgtatatgaaa  4736
4737 gggtactatttgaactctcttactctgtataaaggttggatcatccttaaagtgggtctatttaattttattgcttctta  4816
4817 cagataaaaaaaaaattatgagttggtttgataaaatattgaaggatttaaaataataaataataaataacatataa  4896
4897 tatatgtatataaatttattataatataacatttatctataaaaaagtaaatattgtcataaatctatacaatcgtttag  4976
4977 ccttgctggacgactctcaattatttaaacgagagtaaacatatttgacttttggttatttaacaaattattatttaac  5056
5057 actatatgaaatttttttttttttatcggcaaggaaataaaattaaattaggagggacaatggtgtgtcccaatccttata  5136
5137 caaccaacttccacaggaaggtcaggtcggggacaacaaaaaaacaggcaagggaaattttttaatttgggttgtcttgt  5216
5217 ttgctgcataatttatgcagtaaaacactacacataacccttttagcagtagagcaatggttgaccgtgtgcttagcttc  5296
5297 ttttatttattttttttatcagcaaagaataaataaaataaaatgagacacttcagggatgtttcaacccttatacaaaa  5376
5377 ccccaaaaacaagtttcctagcaccctaccaactaaGGTACC                                         5418
                                       KpnI
```

FIGURE 12A

Nucleotide sequence of the phaseolin promoter-caleosinGUS-phaseolin terminator sequence. The caleosinGUS coding sequence and its deduced aminoacid sequence is indicated. The phaseolin promoter corresponds to nucleotide 1-1545. The sequence encoding caleosin corresponds to nt 1548-2282, the NcoI restriction, which was used for the in-frame cloning and which separates the caleosin and GUS sequence (nt 2284-2289) is underlined. The GUS sequence corresponds to nt 2286-4163. The phaseolin terminator corresponds to nucleotide sequence 4164-5384.

```
   1 GAATTCattgtactcccagtatcattatagtgaaagtttggctctctcgccggtggttttttacctctatttaaagggg   80
  81 ttttccacctaaaaattctggtatcattctcactttacttgttactttaatttctcataatcttggttgaaattatcac  160
 161 gcttccgcacacgatatccctacaaatttattatttgttaaacatttcaaaccgcataaaattttatgaagtcccgtct  240
 241 atctttaatgtagtctaacattttcatattgaaatatataatttacttaattttagcgttggtagaaagcataaagattt  320
 321 attcttattcttcttcatataaatgtttaatatacaatataaacaaattctttaccttaagaaggatttcccattttata  400
 401 ttttaaaaatatatttatcaaatattttttcaaccacgtaaatctcataataataagttgtttcaaaagtaataaaattta  480
 481 actccataattttttttattcgactgatcttaaagcaacacccagtgacacaactagccattttttctttgaataaaaaa  560
 561 atccaattatcattgtattttttttatacaatgaaaatttcaccaaacaatcattgtggtatttctgaagcaagtcatg  640
 641 ttatgcaaaattctataattcccatttgacactacggaagtaactgaagatctgcttttacatgcgagacacatcttcta  720
 721 aagtaattttaataatagttactatattcaagatttcatatatcaaatactcaatattacttctaaaaaattaattagat  800
 801 ataattaaaatattacttttttaattttaagttttaattgttgaatttgtgactattgatttattattctactatgtttaa  880
 881 attgtttatagatagtttaaagtaaatataagtaatgtagtagagtgttagagtgttaccctaaaccataaactataac  960
 961 atttatggtggactaattttcatatatttcttattgcttttaccttttcttggtatgtaagtccgtaactagaattacag 1040
1041 tgggttgccatgacactctgtggtcttttggttcatgcatgggtcttgcgcaagaaaaagacaaagaacaaagaaaaaag 1120
1121 acaaaacagagagacaaaacgcaatcacacaaccaactcaaattagtcactggctgatcaagatcgccgcgtccatgtat 1200
1201 gtctaaatgccatgcaaagcaacacgtgcttaacatgcactttaaatggctcacccatctcaacccacacacaaacacat 1280
1281 tgcctttttcttcatcatcaccacaaccacctgtatatattcattctcttccgccaccteaatttcttcacttcaacaca 1360
1361 cgtcaacctgcatatgcgtgtcatcccatgcccaaatctccatgcatgttccaaccacttctctcttatataataccta 1440
1441 taaatacctctaatatcactcacttctttcatcatccatccatccagagtactactactctactactataataccccaac 1520
1521 ccaactcatattcaatactactctaCC ATG GGG TCA AAG ACG GAG ATG ATG GAG AGA GAC GCA ATG 1586
   1                              M   G   S   K   T   E   M   M   E   R   D   A   M   13
1587 GCT ACG GTG GCT CCC TAT GCG CCG GTC ACT TAC CAC CGC CGT GCT CGT GTT GAC TTG GAT 1646
  14 A   T   V   A   P   Y   A   P   V   T   Y   H   R   R   A   R   V   D   L   D   33
1647 GAT AGA CTT CCT AAA CCT TAT ATG CCA AGA GCA TTG CAA GCA CCA GAC AGA GAA CAC CCG 1706
  34 D   R   L   P   K   P   Y   M   P   R   A   L   Q   A   P   D   R   E   H   P   53
1707 TAC GGA ACT CCA GGC CAT AAG AAT TAC GGA CTT AGT GTT CTT CAA CAG CAT GTC TCC TTC 1766
  54 Y   G   T   P   G   H   K   N   Y   G   L   S   V   L   Q   Q   H   V   S   F   73
1767 TTC GAT ATC GAT GAT AAT GGC ATC ATT TAC CCT TGG GAG ACC TAC TCT GGA CTG CGA ATG 1826
  74 F   D   I   D   D   N   G   I   I   Y   P   W   E   T   Y   S   G   L   R   M   93
1827 CTT GGT TTC AAT ATC ATT GGG TCG CTT ATA ATA GCC GCT GTT ATC AAC CTG ACC CTT AGC 1886
  94 L   G   F   N   I   I   G   S   L   I   I   A   A   V   I   N   L   T   L   S   113
1887 TAT GCC ACT CTT CCG GGG TGG TTA CCT TCA CCT TTC TTC CCT ATA TAC ATA CAC AAC ATA 1946
 114 Y   A   T   L   P   G   W   L   P   S   P   F   F   P   I   Y   I   H   N   I   133
1947 CAC AAG TCA AAG CAT GGA AGT GAT TCA AAA ACA TAT GAC AAT GAA GGA AGG TTT ATG CCG 2006
 134 H   K   S   K   H   G   S   D   S   K   T   Y   D   N   E   G   R   F   M   P   153
2007 GTG AAT CTT GAG TTG ATA TTT AGC AAA TAT GCG AAA ACC TTG CCA GAC AAG TTG AGT CTT 2066
 154 V   N   L   E   L   I   F   S   K   Y   A   K   T   L   P   D   K   L   S   L   173
```

FIGURE 12B

```
2067 GGA GAA CTA TGG GAG ATG ACA GAA GGA AAC CGT GAC GCT TGG GAC ATT TTT GGA TGG ATC 2126
 174 G   E   L   W   E   M   T   E   G   N   R   D   A   W   D   I   F   G   W   I    193
2127 GCA GGC AAA ATA GAG TGG GGA CTG TTG TAC TTG CTA GCA AGG GAT GAA GAA GGG TTT TTG 2186
 194 A   G   K   I   E   W   G   L   L   Y   L   L   A   R   D   E   E   G   F   L    213
2187 TCA AAA GAA GCT ATT AGG CGG TGT TTC GAT GGA AGC TTG TTC GAG TAC TGT GCC AAA ATC 2246
 214 S   K   E   A   I   R   R   C   F   D   G   S   L   F   E   Y   C   A   K   I    233
2247 TAC GCT GGT ATC AGT GAA GAC AAG ACA GCA TAC TAC GCC ATG GTC TTA CGT CCT GTA GAA 2306
 234 Y   A   G   I   S   E   D   K   T   A   Y   Y   A   M   V   L   R   P   V   E    253
2307 ACC CCA ACC CGT GAA ATC AAA AAA CTC GAC GGC CTG TGG GCA TTC AGT CTG GAT CGC GAA 2366
 254 T   P   T   R   E   I   K   K   L   D   G   L   W   A   F   S   L   D   R   E    273
2367 AAC TGT GGA ATT GAT CAG CGT TGG TGG GAA AGC GCG TTA CAA GAA AGC CGG GCA ATT GCT 2426
 274 N   C   G   I   D   Q   R   W   W   E   S   A   L   Q   E   S   R   A   I   A    293
2427 GTG CCA GGC AGT TTT AAC GAT CAG TTC GCC GAT GCA GAT ATT CGT AAT TAT GCG GGC AAC 2486
 294 V   P   G   S   F   N   D   Q   F   A   D   A   D   I   R   N   Y   A   G   N    313
2487 GTC TGG TAT CAG CGC GAA GTC TTT ATA CCG AAA GGT TGG GCA GGC CAG CGT ATC GTG CTG 2546
 314 V   W   Y   Q   R   E   V   F   I   P   K   G   W   A   G   Q   R   I   V   L    333
2547 CGT TTC GAT GCG GTC ACT CAT TAC GGC AAA GTG TGG GTC AAT AAT CAG GAA GTG ATG GAG 2606
 334 R   F   D   A   V   T   H   Y   G   K   V   W   V   N   N   Q   E   V   M   E    353
2607 CAT CAG GGC GGC TAT ACG CCA TTT GAA GCC GAT GTC ACG CCG TAT GTT ATT GCC GGG AAA 2666
 354 H   Q   G   G   Y   T   P   F   E   A   D   V   T   P   Y   V   I   A   G   K    373
2667 AGT GTA CGT ATC ACC GTT TGT GTG AAC AAC GAA CTG AAC TGG CAG ACT ATC CCG CCG GGA 2726
 374 S   V   R   I   T   V   C   V   N   N   E   L   N   W   Q   T   I   P   P   G    393
2727 ATG GTG ATT ACC GAC GAA AAC GGC AAG AAA AAG CAG TCT TAC TTC CAT GAT TTC TTT AAC 2786
 394 M   V   I   T   D   E   N   G   K   K   K   Q   S   Y   F   H   D   F   F   N    413
2787 TAT GCC GGA ATC CAT CGC AGC GTA ATG CTC TAC ACC ACG CCG AAC ACC TGG GTG GAC GAT 2846
 414 Y   A   G   I   H   R   S   V   M   L   Y   T   T   P   N   T   W   V   D   D    433
2847 ATC ACC GTG GTG ACG CAT GTC GCG CAA GAC TGT AAC CAC GCG TCT GTT GAC TGG CAG GTG 2906
 434 I   T   V   V   T   H   V   A   Q   D   C   N   H   A   S   V   D   W   Q   V    453
2907 GTG GCC AAT GGT GAT GTC AGC GTT GAA CTG CGT GAT GCG GAT CAA CAG GTG GTT GCA ACT 2966
 454 V   A   N   G   D   V   S   V   E   L   R   D   A   D   Q   Q   V   V   A   T    473
2967 GGA CAA GGC ACT AGC GGG ACT TTG CAA GTG GTG AAT CCG CAC CTC TGG CAA CCG GGT GAA 3026
 474 G   Q   G   T   S   G   T   L   Q   V   V   N   P   H   L   W   Q   P   G   E    493
3027 GGT TAT CTC TAT GAA CTG TGC GTC ACA GCC AAA AGC CAG ACA GAG TGT GAT ATC TAC CCG 3086
 494 G   Y   L   Y   E   L   C   V   T   A   K   S   Q   T   E   C   D   I   Y   P    513
3087 CTT CGC GTC GGC ATC CGG TCA GTG GCA GTG AAG GGC CAA CAG TTC CTG ATT AAC CAC AAA 3146
 514 L   R   V   G   I   R   S   V   A   V   K   G   Q   Q   F   L   I   N   H   K    533
3147 CCG TTC TAC TTT ACT GGC TTT GGT CGT CAT GAA GAT GCG GAC TTA CGT GGC AAA GGA TTC 3206
 534 P   F   Y   F   T   G   F   G   R   H   E   D   A   D   L   R   G   K   G   F    553
3207 GAT AAC GTG CTG ATG GTG CAC GAC CAC GCA TTA ATG GAC TGG ATT GGG GCC AAC TCC TAC 3266
 554 D   N   V   L   M   V   H   D   H   A   L   M   D   W   I   G   A   N   S   Y    573
3267 CGT ACC TCG CAT TAC CCT TAC GCT GAA GAG ATG CTC GAC TGG GCA GAT GAA CAT GGC ATC 3326
 574 R   T   S   H   Y   P   Y   A   E   E   M   L   D   W   A   D   E   H   G   I    593
3327 GTG GTG ATT GAT GAA ACT GCT GCT GTC GGC TTT TCG CTC TCT TTA GGC ATT GGT TTC GAA 3386
 594 V   V   I   D   E   T   A   A   V   G   F   S   L   S   L   G   I   G   F   E    613
```

FIGURE 12C

```
3387 GCG GGC AAC AAG CCG AAA GAA CTG TAC AGC GAA GAG GCA GTC AAC GGG GAA ACT CAG CAA 3446
 614 A   G   N   K   P   K   E   L   Y   S   E   E   A   V   N   G   E   T   Q   Q    633
3447 GCG CAC TTA CAG GCG ATT AAA GAG CTG ATA GCG CGT GAC AAA AAC CAC CCA AGC CTG GTG 3506
 634 A   H   L   Q   A   I   K   E   L   I   A   R   D   K   N   H   P   S   V   V    653
3507 ATG TGG AGT ATT GCC AAC GAA CCG GAT ACC CGT CCG CAA GGT GCA CGG GAA TAT TTC GCG 3566
 654 M   W   S   I   A   N   E   P   D   T   R   P   Q   G   A   R   E   Y   F   A    673
3567 CCA CTG GCG GAA GCA ACG CGT AAA CTC GAC CCG ACG CGT CCG ATC ACC TGC GTC AAT GTA 3626
 674 P   L   A   E   A   T   R   K   L   D   P   T   R   P   I   T   C   V   N   V    693
3627 ATG TTC TGC GAC GCT CAC ACC GAT ACC ATC AGC GAT CTC TTT GAT GTG CTG TGC CTG AAC 3686
 694 M   F   C   D   A   H   T   D   T   I   S   D   L   F   D   V   L   C   L   N    713
3687 CGT TAT TAC GGA TGG TAT GTC CAA AGC GGC GAT TTG GAA ACG GCA GAG AAG GTA CTG GAA 3746
 714 R   Y   Y   G   W   Y   V   Q   S   G   D   L   E   T   A   E   K   V   L   E    733
3747 AAA GAA CTT CTG GCC TGG CAG GAG AAA CTG CAT CAG CCG ATT ATC ATC ACC GAA TAC GGC 3806
 734 K   E   L   L   A   W   Q   E   K   L   H   Q   P   I   I   I   T   E   Y   G    753
3807 GTG GAT ACG TTA GCC GGG CTG CAC TCA ATG TAC ACC GAC ATG TGG AGT GAA GAG TAT CAG 3866
 754 V   D   T   L   A   G   L   H   S   M   Y   T   D   M   W   S   E   E   Y   Q    773
3867 TGT GCA TGG CTG GAT ATG TAT CAC CGC GTC TTT GAT CGC GTC AGC GCC GTC GTC GGT GAA 3926
 774 C   A   W   L   D   M   Y   H   R   V   F   D   R   V   S   A   V   V   G   E    793
3927 CAG GTA TGG AAT TTC GCC GAT TTT GCG ACC TCG CAA GGC ATA TTG CGC GTT GGC GGT AAC 3986
 794 Q   V   W   N   F   A   D   F   A   T   S   Q   G   I   L   R   V   G   G   N    813
3987 AAG AAA GGG ATC TTC ACT CGC GAC CGC AAA CCG AAG TCG GCG GCT TTT CTG CTG CAA AAA 4046
 814 K   K   G   I   F   T   R   D   R   K   P   K   S   A   A   F   L   L   Q   K    833
4047 CGC TGG ACT GGC ATG AAC TTC GGT GAA AAA CCG CAG CAG GGA GGC AAA CAA TGA ATCAACAA 4108
 834 R   W   T   G   M   N   F   G   E   K   P   Q   Q   G   G   K   Q   *             851
4109 CTCTCCTGGCGCACCATCGTCGGCTACAGCCTCGGTGGAATTCGATATCAAGCTTaaataagtatgaactaaaatgcatg 4188
4189 taggtgtaagagctcatggagagcatggaatattgtatccgaccatgtaacagtataataactgagctccatctcacttc 4268
4269 ttctatgaataaacaaaggatgttatgatatattaacactctatctatgcaccttattgttctatgataaatttcctctt 4348
4349 attattataaatcatctgaatcgtgacggcttatggaatgcttcaaatagtacaaaaacaaatgtgtactataagacttt 4428
4429 ctaaacaattctaactttagcattgtgaacgagacataagtgttaagaagacataacaattataatggaagaagtttgtc 4508
4509 tccatttatatattatatattacccacttatgtattatattaggatgttaaggagacataacaattataaagagagaagt 4588
4589 ttgtatccatttatatattatatactacccatttatatattatacttatccacttatttaatgtctttataaggtttgat 4668
4669 ccatgatatttctaatatttagttgatatgtatatgaaagggtactatttgaactctcttactctgtataaaggttgga 4748
4749 tcatccttaaagtgggtctatttaattttattgcttcttacagataaaaaaaaaattatgagttggtttgataaaatatt 4828
4829 gaaggatttaaaataataataaataataaataacatataatatatgtatataaatttattataatataacatttatctat 4908
4909 aaaaagtaaatattgtcataaatctatacaatcgtttagccttgctggacgactctcaatttatttaaacgagagtaaac 4988
4989 atatttgacttttggttatttaacaaattattatttaacactatatgaaattttttttttttatcggcaaggaaataaa 5068
5069 attaaattaggagggacaatggtgtgtcccaatcctttatacaaccaacttccacaggaaggtcaggtcggggacaacaaa 5148
5149 aaaacaggcaagggaaatttttttaatttgggttgtcttgtttgctgcataatttatgcagtaaaacactacacataaccc 5228
5229 ttttagcagtagagcaatggttgaccgtgtgcttagcttcttttatttttattttttttatcagcaaagaataaataaaata 5308
5309 aaatgagacacttcagggatgtttcaacccttatacaaaaccccaaaaacaagtttcctagcaccctaccaactaaGGTA 5388
5389 CC                                                                                 5390
```

Histochemical staining of β-Glucuronidase (GUS) activity in flax embryos bombarded with vectors pBluescriptIIKS+ (negative control), pSBS2098 (GUS) pSBS2037 (oleosinGUS), and pSBS2601 (caleosinGUS).

SEQUENCE LISTING

```
<160> NUMBER OF SEQ ID NOS: 42

<210> SEQ ID NO 1
<211> LENGTH: 1800
<212> TYPE: DNA
<213> ORGANISM: Arabidopsis thaliana
<220> FEATURE:
<221> NAME/KEY: CDS
<222> LOCATION: (868)..(1221)
<223> OTHER INFORMATION:
<221> NAME/KEY: CDS
<222> LOCATION: (1462)..(1629)
<223> OTHER INFORMATION:

<400> SEQUENCE: 1
```

-continued

```
ccatggctat acccaacctc ggtcttggtc acaccaggaa ctctctggta agctagctcc      60
actccccaga acaaccggc gccaaattgc cggaattgct gacctgaaga cggaacatca      120
tcgtcgggtc cttgggcgat tgcggcggaa gatgggtcag cttgggcttg aggacgagac      180
ccgaatcgag tctgttgaaa ggttgttcat tgggatttgt atacggagat tggtcgtcga      240
gaggtttgag ggaaaggaca aatgggtttg gctctggaga aagagagtgc ggctttagag      300
agagaattga gaggtttaga gagagatgcg gcggcgatga cgggaggaga gacgacgagg      360
acctgcatta tcaaagcagt gacgtggtga aatttggaac ttttaagagg cagatagatt      420
tattatttgt atccattttc ttcattgttc tagaatgtcg cggaacaaat tttaaaacta      480
aatcctaaat ttttctaatt ttgttgccaa tagtggatat gtgggccgta tagaaggaat      540
ctattgaagg cccaaaccca tactgacgag cccaaaggtt cgttttgcgt tttatgtttc      600
ggttcgatgc caacgccaca ttctgagcta ggcaaaaaac aaacgtgtct ttgaatagac      660
tcctctcgtt aacacatgca gcggctgcat ggtgacgcca ttaacacgtg gcctacaatt      720
gcatgatgtc tccattgaca cgtgacttct cgtctccttt cttaatatat ctaacaaaca      780
ctcctacctc ttccaaaata tatacacatc tttttgatca atctctcatt caaaatctca      840
ttctctctag taaacaagaa caaaaaa atg gcg gat aca gct aga gga acc cat      894
                                 Met Ala Asp Thr Ala Arg Gly Thr His
                                  1               5 cac gat atc atc ggc aga gac cag tac ccg atg atg ggc cga gac cga      942
His Asp Ile Ile Gly Arg Asp Gln Tyr Pro Met Met Gly Arg Asp Arg
 10              15                  20                  25 gac cag tac cag atg tcc gga cga gga tct gac tac tcc aag tct agg      990
Asp Gln Tyr Gln Met Ser Gly Arg Gly Ser Asp Tyr Ser Lys Ser Arg
                 30                  35                  40 cag att gct aaa gct gca act gct gtc aca gct ggt ggt tcc ctc ctt     1038
Gln Ile Ala Lys Ala Ala Thr Ala Val Thr Ala Gly Gly Ser Leu Leu
             45                  50                  55 gtt ctc tcc agc ctt acc ctt gtt gga act gtc ata gct ttg act gtt     1086
Val Leu Ser Ser Leu Thr Leu Val Gly Thr Val Ile Ala Leu Thr Val
         60                  65                  70 gca aca cct ctg ctc gtt atc ttc agc cca atc ctt gtc ccg gct ctc     1134
Ala Thr Pro Leu Leu Val Ile Phe Ser Pro Ile Leu Val Pro Ala Leu
     75                  80                  85 atc aca gtt gca ctc ctc atc acc ggt ttt ctt tcc tct gga ggg ttt     1182
Ile Thr Val Ala Leu Leu Ile Thr Gly Phe Leu Ser Ser Gly Gly Phe
 90                  95                 100                 105 ggc att gcc gct ata acc gtt ttc tct tgg att tac aag taagcacaca     1231
Gly Ile Ala Ala Ile Thr Val Phe Ser Trp Ile Tyr Lys
                110                 115 tttatcatct tacttcataa ttttgtgcaa tatgtgcatg catgtgttga gccagtagct     1291
ttggatcaat ttttttggtc gaataacaaa tgtaacaata agaaattgca aattctaggg     1351
aacatttggt taactaaata cgaaatttga cctagctagc ttgaatgtgt ctgtgtatat     1411
catctatata ggtaaaatgc ttggtatgat acctattgat tgtgaatagg tac gca     1467
                                                         Tyr Ala
                                                             120 acg gga gag cac cca cag gga tca gac aag ttg gac agt gca agg atg     1515
Thr Gly Glu His Pro Gln Gly Ser Asp Lys Leu Asp Ser Ala Arg Met
                125                 130                 135 aag ttg gga agc aaa gct cag gat ctg aaa gac aga gct cag tac tac     1563
Lys Leu Gly Ser Lys Ala Gln Asp Leu Lys Asp Arg Ala Gln Tyr Tyr
            140                 145                 150
```

```
gga cag caa cat act ggt ggg gaa cat gac cgt gac cgt act cgt ggt    1611
Gly Gln Gln His Thr Gly Gly Glu His Asp Arg Asp Arg Thr Arg Gly
        155                 160                 165 ggc cag cac act act taa gttacccccac tgatgtcatc gtcatagtcc          1659
Gly Gln His Thr Thr
    170 aataactcca atgtcgggga gttagtttat gaggaataaa gtgtttagaa tttgatcagg   1719 gggagataat aaaagccgag tttgaatctt tttgttataa gtaatgttta tgtgtgtttc   1779 tatatgttgt caaatggtac c                                            1800
```

<210> SEQ ID NO 2
<211> LENGTH: 118
<212> TYPE: PRT
<213> ORGANISM: Arabidopsis thaliana

<400> SEQUENCE: 2

```
Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
                20                  25                  30

Arg Gly Ser Asp Tyr Ser Lys Ser Arg Gln Ile Ala Lys Ala Ala Thr
            35                  40                  45

Ala Val Thr Ala Gly Gly Ser Leu Leu Val Leu Ser Ser Leu Thr Leu
        50                  55                  60

Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
                100                 105                 110

Phe Ser Trp Ile Tyr Lys
            115
```

<210> SEQ ID NO 3
<211> LENGTH: 55
<212> TYPE: PRT
<213> ORGANISM: Arabidopsis thaliana

<400> SEQUENCE: 3

```
Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
                20                  25                  30

Tyr Tyr Gly Gln Gln His Thr Gly Gly Glu His Asp Arg Asp Arg Thr
            35                  40                  45

Arg Gly Gly Gln His Thr Thr
        50                  55
```

<210> SEQ ID NO 4
<211> LENGTH: 564
<212> TYPE: DNA
<213> ORGANISM: Brassica napus
<220> FEATURE:
<221> NAME/KEY: CDS
<222> LOCATION: (1)..(561)
<223> OTHER INFORMATION:

<400> SEQUENCE: 4

```
atg gcg gat aca gct aga acc cat cac gat gtc aca agt cga gat cag    48
```

```
Met Ala Asp Thr Ala Arg Thr His His Asp Val Thr Ser Arg Asp Gln
1               5                   10                  15 tat ccc cga gac cga gac cag tat tct atg atc ggt cga gac cgt gac      96
Tyr Pro Arg Asp Arg Asp Gln Tyr Ser Met Ile Gly Arg Asp Arg Asp
                20                  25                  30 cag tac tct atg atg ggc cga gac cga gac cag tac aac atg tat ggt      144
Gln Tyr Ser Met Met Gly Arg Asp Arg Asp Gln Tyr Asn Met Tyr Gly
            35                  40                  45 cga gac tac tcc aag tct aga cag att gct aag gct gtt acc gca gtc      192
Arg Asp Tyr Ser Lys Ser Arg Gln Ile Ala Lys Ala Val Thr Ala Val
        50                  55                  60 acg gcg ggt ggg tcc ctc ctt gtc ctc tcc agt ctc acc ctt gtt ggt      240
Thr Ala Gly Gly Ser Leu Leu Val Leu Ser Ser Leu Thr Leu Val Gly
65                  70                  75                  80 act gtc att gct ttg act gtt gcc act cca ctc ctc gtt atc ttt agc      288
Thr Val Ile Ala Leu Thr Val Ala Thr Pro Leu Leu Val Ile Phe Ser
                85                  90                  95 cca atc ctc gtg ccg gct ctc atc acc gta gca ctt ctc atc act ggc      336
Pro Ile Leu Val Pro Ala Leu Ile Thr Val Ala Leu Leu Ile Thr Gly
            100                 105                 110 ttt ctc tcc tct ggt ggg ttt gcc att gca gct ata acc gtc ttc tcc      384
Phe Leu Ser Ser Gly Gly Phe Ala Ile Ala Ala Ile Thr Val Phe Ser
        115                 120                 125 tgg atc tat aag tac gca acg gga gag cac cca cag ggg tca gat aag      432
Trp Ile Tyr Lys Tyr Ala Thr Gly Glu His Pro Gln Gly Ser Asp Lys
    130                 135                 140 ttg gac agt gca agg atg aag ctg gga acc aaa gct cag gat att aaa      480
Leu Asp Ser Ala Arg Met Lys Leu Gly Thr Lys Ala Gln Asp Ile Lys
145                 150                 155                 160 gac aga gct caa tac tac gga cag caa cat aca ggt ggt gag cat gac      528
Asp Arg Ala Gln Tyr Tyr Gly Gln Gln His Thr Gly Gly Glu His Asp
                165                 170                 175 cgt gac cgt act cgt ggt ggc cag cac act act taa                      564
Arg Asp Arg Thr Arg Gly Gly Gln His Thr Thr
            180                 185
```

<210> SEQ ID NO 5
<211> LENGTH: 187
<212> TYPE: PRT
<213> ORGANISM: Brassica napus

<400> SEQUENCE: 5

```
Met Ala Asp Thr Ala Arg Thr His His Asp Val Thr Ser Arg Asp Gln
1               5                   10                  15

Tyr Pro Arg Asp Arg Asp Gln Tyr Ser Met Ile Gly Arg Asp Arg Asp
                20                  25                  30

Gln Tyr Ser Met Met Gly Arg Asp Arg Asp Gln Tyr Asn Met Tyr Gly
            35                  40                  45

Arg Asp Tyr Ser Lys Ser Arg Gln Ile Ala Lys Ala Val Thr Ala Val
        50                  55                  60

Thr Ala Gly Gly Ser Leu Leu Val Leu Ser Ser Leu Thr Leu Val Gly
65                  70                  75                  80

Thr Val Ile Ala Leu Thr Val Ala Thr Pro Leu Leu Val Ile Phe Ser
                85                  90                  95

Pro Ile Leu Val Pro Ala Leu Ile Thr Val Ala Leu Leu Ile Thr Gly
            100                 105                 110

Phe Leu Ser Ser Gly Gly Phe Ala Ile Ala Ala Ile Thr Val Phe Ser
        115                 120                 125
```

-continued

```
Trp Ile Tyr Lys Tyr Ala Thr Gly Glu His Pro Gln Gly Ser Asp Lys
    130                 135                 140

Leu Asp Ser Ala Arg Met Lys Leu Gly Thr Lys Ala Gln Asp Ile Lys
145                 150                 155                 160

Asp Arg Ala Gln Tyr Tyr Gly Gln Gln His Thr Gly Gly Glu His Asp
                165                 170                 175

Arg Asp Arg Thr Arg Gly Gly Gln His Thr Thr
            180                 185

<210> SEQ ID NO 6
<211> LENGTH: 2733
<212> TYPE: DNA
<213> ORGANISM: Artificial Sequence
<220> FEATURE:
<223> OTHER INFORMATION: Oleosin-Chymosin Fusion
<221> NAME/KEY: CDS
<222> LOCATION: (850)..(1203)
<223> OTHER INFORMATION:
<221> NAME/KEY: CDS
<222> LOCATION: (1444)..(2727)
<223> OTHER INFORMATION:

<400> SEQUENCE: 6
ataagcttgc atgcctgcgg aactctctgg taagctagct ccactcccca gaaacaaccg      60
gcgccaaatt gccggaattg ctgacctgaa gacggaacat catcgtcggg tccttgggcg     120
attgcggcgg aagatgggtc agcttgggct tgaggacgag acccgaatcg agtctgttga     180
aaggttgttc attgggattt gtatacgagg attggtcgtc gagaggtttg agggaaagga     240
caaatgggtt tggctctgga gaaagagagt gcggctttag agagagaatt gagaggttta     300
gagagagatg cggcggcgat gacgggagga gagacgacga ggacctgcat tatcaaagca     360
gtgacgtggt gaaatttgga acttttaaga ggcagataga tttattattt gtatccattt     420
tcttcattgt tctagaatgt cgcggaacaa attttaaaac taaatcctaa atttttctaa     480
ttttgttgcc aatagtggat atgtgggccg tatagaagga atctattgaa ggcccaaacc     540
catactgacg agcccaaagg ttcgttttgc gttttatgtt tcggttcgat gccaacgcca     600
cattctgagc taggcaaaaa acaaacgtgt ctttgaatag actcctctcg ttaacacatg     660
cagcggctgc atggtgacgc cattaacacg tggcctacaa ttgcatgatg tctccattga     720
cacgtgactt ctcgtctcct tcttaatat atctaacaaa cactcctacc tcttccaaaa     780
tatatacaca tcttttgat caatctctca ttcaaaatct cattctctct agtaaacaag     840 aacaaaaaa atg gcg gat aca gct aga gga acc cat cac gat atc atc ggc     891
           Met Ala Asp Thr Ala Arg Gly Thr His His Asp Ile Ile Gly
             1               5                  10 aga gac cag tac ccg atg atg ggc cga gac cga gac cag tac cag atg     939
Arg Asp Gln Tyr Pro Met Met Gly Arg Asp Arg Asp Gln Tyr Gln Met
 15                  20                  25                  30 tcc gga cga gga tct gac tac tcc aag tct agg cag att gct aaa gct     987
Ser Gly Arg Gly Ser Asp Tyr Ser Lys Ser Arg Gln Ile Ala Lys Ala
                 35                  40                  45 gca act gct gtc aca gct ggt ggt tcc ctc ctt gtt ctc tcc agc ctt    1035
Ala Thr Ala Val Thr Ala Gly Gly Ser Leu Leu Val Leu Ser Ser Leu
             50                  55                  60 acc ctt gtt gga act gtc ata gct ttg act gtt gca aca cct ctg ctc    1083
Thr Leu Val Gly Thr Val Ile Ala Leu Thr Val Ala Thr Pro Leu Leu
 65                  70                  75 gtt atc ttc agc cca atc ctt gtc ccg gct ctc atc aca gtt gca ctc    1131
Val Ile Phe Ser Pro Ile Leu Val Pro Ala Leu Ile Thr Val Ala Leu
         80                  85                  90
```

```
ctc atc acc ggt ttt ctt tcc tct gga ggg ttt ggc att gcc gct ata    1179
Leu Ile Thr Gly Phe Leu Ser Ser Gly Gly Phe Gly Ile Ala Ala Ile
 95                 100                 105                 110 acc gtt ttc tct tgg att tac aag taagcacaca tttatcatct tacttcataa   1233
Thr Val Phe Ser Trp Ile Tyr Lys
                115 ttttgtgcaa tatgtgcatg catgtgttga gccagtagct ttggatcaat ttttttggtc   1293 gaataacaaa tgtaacaata agaaattgca aattctaggg aacatttggt taactaaata   1353 cgaaatttga cctagctagc ttgaatgtgt ctgtgtatat catctatata ggtaaaatgc   1413 ttggtatgat acctattgat tgtgaatagg tac gca acg gga gag cac cca cag   1467
                                 Tyr Ala Thr Gly Glu His Pro Gln
                                                 120         125 gga tca gac aag ttg gac agt gca agg atg aag ttg gga agc aaa gct    1515
Gly Ser Asp Lys Leu Asp Ser Ala Arg Met Lys Leu Gly Ser Lys Ala
            130                 135                 140 cag gat ctg aaa gac aga gct cag tac tac gga cag caa cat act ggt    1563
Gln Asp Leu Lys Asp Arg Ala Gln Tyr Tyr Gly Gln Gln His Thr Gly
        145                 150                 155 ggg gaa cat gac cgt gac cgt act cgt ggt ggc cag cac act act ctc    1611
Gly Glu His Asp Arg Asp Arg Thr Arg Gly Gly Gln His Thr Thr Leu
    160                 165                 170 gtt cca cga gga tcc atg gct gag atc acc agg atc cct ctg tac aaa    1659
Val Pro Arg Gly Ser Met Ala Glu Ile Thr Arg Ile Pro Leu Tyr Lys
175                 180                 185                 190 ggc aag tct ctg agg aag gcg ctg aag gag cat ggg ctt ctg gag gac    1707
Gly Lys Ser Leu Arg Lys Ala Leu Lys Glu His Gly Leu Leu Glu Asp
                195                 200                 205 ttc ctg cag aaa cag cag tat ggc atc agc agc aag tac tcc ggc ttc    1755
Phe Leu Gln Lys Gln Gln Tyr Gly Ile Ser Ser Lys Tyr Ser Gly Phe
            210                 215                 220 ggg gag gtg gcc agc gtg ccc ctg acc aac tac ctg gat agt cag tac    1803
Gly Glu Val Ala Ser Val Pro Leu Thr Asn Tyr Leu Asp Ser Gln Tyr
        225                 230                 235 ttt ggg aag atc tac ctc ggg acc ccg ccc cag gag ttc acc gtg ctg    1851
Phe Gly Lys Ile Tyr Leu Gly Thr Pro Pro Gln Glu Phe Thr Val Leu
    240                 245                 250 ttt gac act ggc tcc tct gac ttc tgg gta ccc tct atc tac tgc aag    1899
Phe Asp Thr Gly Ser Ser Asp Phe Trp Val Pro Ser Ile Tyr Cys Lys
255                 260                 265                 270 agc aat gcc tgc aaa aac cac cag cgc ttc gac ccg aga aag tcg tcc    1947
Ser Asn Ala Cys Lys Asn His Gln Arg Phe Asp Pro Arg Lys Ser Ser
                275                 280                 285 acc ttc cag aac ctg ggc aag ccc ctg tct atc cac tac ggg aca ggc    1995
Thr Phe Gln Asn Leu Gly Lys Pro Leu Ser Ile His Tyr Gly Thr Gly
            290                 295                 300 agc atg cag ggc atc ctg ggc tat gac acc gtc act gtc tcc aac att    2043
Ser Met Gln Gly Ile Leu Gly Tyr Asp Thr Val Thr Val Ser Asn Ile
        305                 310                 315 gtg gac atc cag cag aca gta ggc ctg agc acc cag gag ccc ggg gac    2091
Val Asp Ile Gln Gln Thr Val Gly Leu Ser Thr Gln Glu Pro Gly Asp
    320                 325                 330 gtc ttc acc tat gcc gaa ttc gac ggg atc ctg ggg atg gcc tac ccc    2139
Val Phe Thr Tyr Ala Glu Phe Asp Gly Ile Leu Gly Met Ala Tyr Pro
335                 340                 345                 350 tcg ctc gcc tca gag tac tcg ata ccc gtg ttt gac aac atg atg aac    2187
Ser Leu Ala Ser Glu Tyr Ser Ile Pro Val Phe Asp Asn Met Met Asn
                355                 360                 365
```

-continued

| | | |
|---|---|---|
| agg cac ctg gtg gcc caa gac ctg ttc tcg gtt tac atg gac agg aat<br>Arg His Leu Val Ala Gln Asp Leu Phe Ser Val Tyr Met Asp Arg Asn<br>370                                375                       380 | 2235 |
| ggc cag gag agc atg ctc acg ctg ggg gcc atc gac ccg tcc tac tac<br>Gly Gln Glu Ser Met Leu Thr Leu Gly Ala Ile Asp Pro Ser Tyr Tyr<br>385                                390                       395 | 2283 |
| aca ggg tcc ctg cac tgg gtg ccc gtg aca gtg cag cag tac tgg cag<br>Thr Gly Ser Leu His Trp Val Pro Val Thr Val Gln Gln Tyr Trp Gln<br>400                                405                       410 | 2331 |
| ttc act gtg gac agt gtc acc atc agc ggt gtg gtt gtg gcc tgt gag<br>Phe Thr Val Asp Ser Val Thr Ile Ser Gly Val Val Val Ala Cys Glu<br>415                                420                       425               430 | 2379 |
| ggt ggc tgt cag gcc atc ttg gac acg ggc acc tcc aag ctg gtc ggg<br>Gly Gly Cys Gln Ala Ile Leu Asp Thr Gly Thr Ser Lys Leu Val Gly<br>                                    435                       440                       445 | 2427 |
| ccc agc agc gac atc ctc aac atc cag cag gcc att gga gcc aca cag<br>Pro Ser Ser Asp Ile Leu Asn Ile Gln Gln Ala Ile Gly Ala Thr Gln<br>                                    450                       455                       460 | 2475 |
| aac cag tac ggt gag ttt gac atc gac tgc gac aac ctg agc tac atg<br>Asn Gln Tyr Gly Glu Phe Asp Ile Asp Cys Asp Asn Leu Ser Tyr Met<br>                                    465                       470                       475 | 2523 |
| ccc act gtg gtc ttt gag atc aat ggc aaa atg tac cca ctg acc ccc<br>Pro Thr Val Val Phe Glu Ile Asn Gly Lys Met Tyr Pro Leu Thr Pro<br>480                                485                       490 | 2571 |
| tcc gcc tat acc agc caa gac cag ggc ttc tgt acc agt ggc ttc cag<br>Ser Ala Tyr Thr Ser Gln Asp Gln Gly Phe Cys Thr Ser Gly Phe Gln<br>495                                500                       505                       510 | 2619 |
| agt gaa aat cat tcc cag aaa tgg atc ctg ggg gat gtt ttc atc cga<br>Ser Glu Asn His Ser Gln Lys Trp Ile Leu Gly Asp Val Phe Ile Arg<br>                                    515                       520                       525 | 2667 |
| gag tat tac agc gtc ttt gac agg gcc aac aac ctc gtg ggg ctg gcc<br>Glu Tyr Tyr Ser Val Phe Asp Arg Ala Asn Asn Leu Val Gly Leu Ala<br>                                    530                       535                       540 | 2715 |
| aaa gcc atc tga aagctt<br>Lys Ala Ile<br>545 | 2733 |

<210> SEQ ID NO 7
<211> LENGTH: 118
<212> TYPE: PRT
<213> ORGANISM: Artificial Sequence
<220> FEATURE:
<223> OTHER INFORMATION: Oleosin-Chymosin Fusion

<400> SEQUENCE: 7

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
               20                   25                   30

Arg Gly Ser Asp Tyr Ser Lys Ser Arg Gln Ile Ala Lys Ala Ala Thr
        35                   40                   45

Ala Val Thr Ala Gly Gly Ser Leu Leu Val Leu Ser Ser Leu Thr Leu
50                       55                   60

Val Gly Thr Val Ile Ala Leu Thr Val Ala Thr Pro Leu Leu Val Ile
65               70                   75                   80

Phe Ser Pro Ile Leu Val Pro Ala Leu Ile Thr Val Ala Leu Leu Ile
               85                   90                   95

Thr Gly Phe Leu Ser Ser Gly Gly Phe Gly Ile Ala Ala Ile Thr Val
                  100                 105               110

Phe Ser Trp Ile Tyr Lys
        115

<210> SEQ ID NO 8
<211> LENGTH: 427
<212> TYPE: PRT
<213> ORGANISM: Artificial Sequence
<220> FEATURE:
<223> OTHER INFORMATION: Oleosin-Chymosin Fusion

<400> SEQUENCE: 8

Tyr Ala Thr Gly Glu His Pro Gln Gly Ser Asp Lys Leu Asp Ser Ala
1               5                   10                  15

Arg Met Lys Leu Gly Ser Lys Ala Gln Asp Leu Lys Asp Arg Ala Gln
            20                  25                  30

Tyr Tyr Gly Gln Gln His Thr Gly Glu His Asp Arg Asp Arg Thr
        35                  40                  45

Arg Gly Gly Gln His Thr Thr Leu Val Pro Arg Gly Ser Met Ala Glu
    50                  55                  60

Ile Thr Arg Ile Pro Leu Tyr Lys Gly Lys Ser Leu Arg Lys Ala Leu
65                  70                  75                  80

Lys Glu His Gly Leu Leu Glu Asp Phe Leu Gln Lys Gln Gln Tyr Gly
                85                  90                  95

Ile Ser Ser Lys Tyr Ser Gly Phe Gly Glu Val Ala Ser Val Pro Leu
            100                 105                 110

Thr Asn Tyr Leu Asp Ser Gln Tyr Phe Gly Lys Ile Tyr Leu Gly Thr
        115                 120                 125

Pro Pro Gln Glu Phe Thr Val Leu Phe Asp Thr Gly Ser Ser Asp Phe
    130                 135                 140

Trp Val Pro Ser Ile Tyr Cys Lys Ser Asn Ala Cys Lys Asn His Gln
145                 150                 155                 160

Arg Phe Asp Pro Arg Lys Ser Ser Thr Phe Gln Asn Leu Gly Lys Pro
                165                 170                 175

Leu Ser Ile His Tyr Gly Thr Gly Ser Met Gln Gly Ile Leu Gly Tyr
            180                 185                 190

Asp Thr Val Thr Val Ser Asn Ile Val Asp Ile Gln Gln Thr Val Gly
        195                 200                 205

Leu Ser Thr Gln Glu Pro Gly Asp Val Phe Thr Tyr Ala Glu Phe Asp
    210                 215                 220

Gly Ile Leu Gly Met Ala Tyr Pro Ser Leu Ala Ser Glu Tyr Ser Ile
225                 230                 235                 240

Pro Val Phe Asp Asn Met Met Asn Arg His Leu Val Ala Gln Asp Leu
                245                 250                 255

Phe Ser Val Tyr Met Asp Arg Asn Gly Gln Glu Ser Met Leu Thr Leu
            260                 265                 270

Gly Ala Ile Asp Pro Ser Tyr Tyr Thr Gly Ser Leu His Trp Val Pro
        275                 280                 285

Val Thr Val Gln Gln Tyr Trp Gln Phe Thr Val Asp Ser Val Thr Ile
    290                 295                 300

Ser Gly Val Val Val Ala Cys Glu Gly Gly Cys Gln Ala Ile Leu Asp
305                 310                 315                 320

Thr Gly Thr Ser Lys Leu Val Gly Pro Ser Ser Asp Ile Leu Asn Ile
                325                 330                 335

Gln Gln Ala Ile Gly Ala Thr Gln Asn Gln Tyr Gly Glu Phe Asp Ile
            340                 345                 350

```
Asp Cys Asp Asn Leu Ser Tyr Met Pro Thr Val Val Phe Glu Ile Asn
            355                 360                 365
Gly Lys Met Tyr Pro Leu Thr Pro Ser Ala Tyr Thr Ser Gln Asp Gln
        370                 375                 380
Gly Phe Cys Thr Ser Gly Phe Gln Ser Glu Asn His Ser Gln Lys Trp
385                 390                 395                 400
Ile Leu Gly Asp Val Phe Ile Arg Glu Tyr Tyr Ser Val Phe Asp Arg
                405                 410                 415
Ala Asn Asn Leu Val Gly Leu Ala Lys Ala Ile
            420                 425

<210> SEQ ID NO 9
<211> LENGTH: 5
<212> TYPE: PRT
<213> ORGANISM: Artificial Sequence
<220> FEATURE:
<223> OTHER INFORMATION: Thrombin Cleavage Site

<400> SEQUENCE: 9

Leu Val Pro Arg Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Factor Xa Cleavage Site

<400> SEQUENCE: 10

Phe Glu Gly Arg
1

<210> SEQ ID NO 11
<211> LENGTH: 4
<212> TYPE: PRT
<213> ORGANISM: Artificial Sequence
<220> FEATURE:
<223> OTHER INFORMATION: Collagenase Cleavage Site

<400> SEQUENCE: 11

Pro Leu Gly Pro
1

<210> SEQ ID NO 12
<211> LENGTH: 7
<212> TYPE: PRT
<213> ORGANISM: Artificial Sequence
<220> FEATURE:
<223> OTHER INFORMATION: TEV Protease

<400> SEQUENCE: 12

Glu Asn Leu Tyr Phe Gln Gly
1               5

<210> SEQ ID NO 13
<211> LENGTH: 14
<212> TYPE: DNA
<213> ORGANISM: Artificial Sequence
<220> FEATURE:
<223> OTHER INFORMATION: Carrot

<400> SEQUENCE: 13
tctcaacaat ggca                                                       14
```

<210> SEQ ID NO 14
<211> LENGTH: 14
<212> TYPE: DNA
<213> ORGANISM: Artificial Sequence
<220> FEATURE:
<223> OTHER INFORMATION: Maize

<400> SEQUENCE: 14
cggcagcaat ggcg                                                        14

<210> SEQ ID NO 15
<211> LENGTH: 22
<212> TYPE: DNA
<213> ORGANISM: Artificial Sequence
<220> FEATURE:
<223> OTHER INFORMATION: GVR10 5' Primer

<400> SEQUENCE: 15
cactgcagga actctctggt aa                                               22

<210> SEQ ID NO 16
<211> LENGTH: 31
<212> TYPE: DNA
<213> ORGANISM: Artificial Sequence
<220> FEATURE:
<223> OTHER INFORMATION: ALP1 Primer

<400> SEQUENCE: 16
ctacccggga tcctgtttac tagagagaat g                                     31

<210> SEQ ID NO 17
<211> LENGTH: 62
<212> TYPE: DNA
<213> ORGANISM: Artificial Sequence
<220> FEATURE:
<223> OTHER INFORMATION: GVR01 Primer

<400> SEQUENCE: 17
aatcccatgg atcctcgtgg aacgagagta gtgtgctggc caccacgagt acggtcacgg      60
tc                                                                     62

<210> SEQ ID NO 18
<211> LENGTH: 24
<212> TYPE: DNA
<213> ORGANISM: Artificial Sequence
<220> FEATURE:
<223> OTHER INFORMATION: GVR10 3' Primer

<400> SEQUENCE: 18
cactgcagga actctctggt aagc                                             24

<210> SEQ ID NO 19
<211> LENGTH: 29
<212> TYPE: DNA
<213> ORGANISM: Artificial Sequence
<220> FEATURE:
<223> OTHER INFORMATION: GVR20 Primer

<400> SEQUENCE: 19
gaggatccat ggtacgtcct gtagaaacc                                        29

<210> SEQ ID NO 20
<211> LENGTH: 17
<212> TYPE: DNA
<213> ORGANISM: Artificial Sequence

```
<220> FEATURE:
<223> OTHER INFORMATION: Primer GVR20

<400> SEQUENCE: 20
gtaaaacgac ggccagt                                                17

<210> SEQ ID NO 21
<211> LENGTH: 6
<212> TYPE: PRT
<213> ORGANISM: Artificial Sequence
<220> FEATURE:
<223> OTHER INFORMATION: Peptide

<400> SEQUENCE: 21

Leu Val Pro Arg Gly Ser
1               5

<210> SEQ ID NO 22
<211> LENGTH: 9
<212> TYPE: PRT
<213> ORGANISM: Artificial Sequence
<220> FEATURE:
<223> OTHER INFORMATION: IL-1-B Peptide

<400> SEQUENCE: 22

Val Gln Gly Glu Glu Ser Asn Asp Lys
1               5

<210> SEQ ID NO 23
<211> LENGTH: 28
<212> TYPE: DNA
<213> ORGANISM: Artificial Sequence
<220> FEATURE:
<223> OTHER INFORMATION: OleoPromK Primer

<400> SEQUENCE: 23
cgcggtacca tggctatacc caacctcg                                    28

<210> SEQ ID NO 24
<211> LENGTH: 28
<212> TYPE: DNA
<213> ORGANISM: Artificial Sequence
<220> FEATURE:
<223> OTHER INFORMATION: 3' Primer

<400> SEQUENCE: 24
cgcatcgatg ttcttgttta ctagagag                                    28

<210> SEQ ID NO 25
<211> LENGTH: 36
<212> TYPE: DNA
<213> ORGANISM: Artificial Sequence
<220> FEATURE:
<223> OTHER INFORMATION: 5'-GUS-Cla Primer

<400> SEQUENCE: 25
gccatcgatc atatgttacg tcctgtagaa acccca                           36

<210> SEQ ID NO 26
<211> LENGTH: 37
<212> TYPE: DNA
<213> ORGANISM: Artificial Sequence
<220> FEATURE:
<223> OTHER INFORMATION: 3'-GUS-FX-Bam Primer

<400> SEQUENCE: 26
```
cgcggatcct cttccttcga tttgtttgcc tccctgc                                37

<210> SEQ ID NO 27
<211> LENGTH: 27
<212> TYPE: DNA
<213> ORGANISM: Artificial Sequence
<220> FEATURE:
<223> OTHER INFORMATION: 5'-Bam-Oleo

<400> SEQUENCE: 27
cgcggatcca tggcggatac agctaga                                           27

<210> SEQ ID NO 28
<211> LENGTH: 36
<212> TYPE: DNA
<213> ORGANISM: Artificial Sequence
<220> FEATURE:
<223> OTHER INFORMATION: 3'-Oleo-Xba

<400> SEQUENCE: 28
tgctctagac gatgacatca gtggggtaac ttaagt                                 36

<210> SEQ ID NO 29
<211> LENGTH: 6
<212> TYPE: PRT
<213> ORGANISM: Artificial Sequence
<220> FEATURE:
<223> OTHER INFORMATION: Spacer

<400> SEQUENCE: 29

Leu Val Pro Arg Gly Ser
1               5

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
atctctagaa ttcaactact cttgctcaaa g                                      31

<210> SEQ ID NO 31
<211> LENGTH: 29
<212> TYPE: DNA
<213> ORGANISM: Artificial Sequence
<220> FEATURE:
<223> OTHER INFORMATION: Primer

<400> SEQUENCE: 31
gggttgctcg agatttctaa tcaatttat                                         29

<210> SEQ ID NO 32
<211> LENGTH: 22
<212> TYPE: DNA
<213> ORGANISM: Artificial Sequence
<220> FEATURE:
<223> OTHER INFORMATION: GVR979 Primer

<400> SEQUENCE: 32
taccatgggg tcaaagacgg ag                                                22

<210> SEQ ID NO 33
<211> LENGTH: 28
<212> TYPE: DNA

<213> ORGANISM: Artificial Sequence
<220> FEATURE:
<223> OTHER INFORMATION: GVR980 Primer

<400> SEQUENCE: 33
atccatggcg tagtatgctg tcttgtct                                              28

<210> SEQ ID NO 34
<211> LENGTH: 748
<212> TYPE: DNA
<213> ORGANISM: Arabidopsis caleosin

<400> SEQUENCE: 34

| | | | | | |
|---|---|---|---|---|---|
| taccatgggg | tcaaagacgg | agatgatgga | gagagacgca | atggctacgg | tggctcccta | 60 |
| tgcgccggtc | acttaccatc | gccgtgctcg | tgttgacttg | gatgatagac | ttcctaaacc | 120 |
| ttatatgcca | agagcattgc | aagcaccaga | cagagaacac | ccgtacggaa | ctccaggcca | 180 |
| taagaattac | ggactagtg | ttcttcaaca | gcatgtctcc | ttcttcgata | tcgatgataa | 240 |
| tggcatcatt | tacccttggg | agacctactc | tggactgcga | atgcttggtt | caatatcat | 300 |
| tgggtcgctt | ataatagccg | ctgttatcaa | cctgacccttt | agctatgcca | ctcttccggg | 360 |
| gtggttaccct | tcacctttct | tccctatata | catacacaac | atacacaagt | caaagcatgg | 420 |
| aagtgattca | aaaacatatg | acaatgaagg | aaggtttatg | ccggtgaatc | ttgagttgat | 480 |
| atttagcaaa | tatgcgaaaa | ccttgccaga | caagttgagt | cttggagaac | tatgggagat | 540 |
| gacagaagga | aaccgtgacg | cttgggacat | ttttggatgg | atcgcaggca | aaatagagtg | 600 |
| gggactgttg | tacttgctag | caagggatga | agaagggttt | ttgtcaaaag | aagctattag | 660 |
| gcggtgtttc | gatggaagct | tgttcgagta | ctgtgccaaa | atctacgctg | gtatcagtga | 720 |
| agacaagaca | gcatactacg | ccatggat | | | | 748 |

<210> SEQ ID NO 35
<211> LENGTH: 738
<212> TYPE: DNA
<213> ORGANISM: Arabidopsis caleosin

<400> SEQUENCE: 35

| | | | | | |
|---|---|---|---|---|---|
| atggggtcaa | agacggagat | gatggagaga | gacgcaatgg | ctacggtggc | tccctatgcg | 60 |
| ccggtcactt | accaccgccg | tgctcgtgtt | gacttggatg | atagacttcc | taaaccttat | 120 |
| atgccaagag | cattgcaagc | accagacaga | gaacacccgt | acggaactcc | aggccataag | 180 |
| aattacggac | ttagtgttct | tcaacagcat | gtctccttct | tcgatatcga | tgataatggc | 240 |
| atcatttacc | cttgggagac | ctactctgga | ctgcgaatgc | ttggtttcaa | tatcattggg | 300 |
| tcgcttataa | tagccgctgt | tatcaacctg | acccttagct | atgccactct | tccggggtgg | 360 |
| ttaccttcac | ctttcttccc | tatatacata | cacaacatac | acaagtcaaa | gcatggaagt | 420 |
| gattcaaaaa | catatgacaa | tgaaggaagg | tttatgccgg | tgaatcttga | gttgatattt | 480 |
| agcaaatatg | cgaaaaccttt | gccagacaag | ttgagtcttg | agaactatg | ggagatgaca | 540 |
| gaaggaaaacc | gtgacgcttg | gacattttt | ggatggatcg | caggcaaaat | agagtgggga | 600 |
| ctgttgtact | tgctagcaag | ggatgaagaa | gggttttttgt | caaaagaagc | tattaggcgg | 660 |
| tgtttcgatg | gaagcttgtt | cgagtactgt | gccaaaatct | acgctggtat | cagtgaagac | 720 |
| aagacagcat | actactaa | | | | | 738 |

<210> SEQ ID NO 36

-continued

```
<211> LENGTH: 4652
<212> TYPE: DNA
<213> ORGANISM: Artificial Sequence
<220> FEATURE:
<223> OTHER INFORMATION: Phas-GUS-phas
<221> NAME/KEY: CDS
<222> LOCATION: (1548)..(3359)
<223> OTHER INFORMATION:

<400> SEQUENCE: 36
```

| | |
|---|---|
| gaattcattg tactcccagt atcattatag tgaaagtttt ggctctctcg ccggtggttt | 60 |
| tttacctcta tttaaagggg ttttccacct aaaaattctg gtatcattct cactttactt | 120 |
| gttactttaa tttctcataa tctttggttg aaattatcac gcttccgcac acgatatccc | 180 |
| tacaaattta ttatttgtta aacattttca aaccgcataa aatttttatga agtcccgtct | 240 |
| atctttaatg tagtctaaca ttttcatatt gaaatatata atttacttaa ttttagcgtt | 300 |
| ggtagaaagc ataagagattt attcttattc ttcttcatat aaatgtttaa tatacaatat | 360 |
| aaacaaattc tttaccttaa gaaggatttc ccatttttata ttttaaaaat atatttatca | 420 |
| aatatttttc aaccacgtaa atctcataat aataagttgt ttcaaaagta ataaaattta | 480 |
| actccataat ttttttattc gactgatctt aaagcaacac ccagtgacac aactagccat | 540 |
| ttttttcttt gaataaaaaa atccaattat cattgtattt tttttataca atgaaaattt | 600 |
| caccaaacaa tcatttgtgg tatttctgaa gcaagtcatg ttatgcaaaa ttctataatt | 660 |
| cccatttgac actacggaag taactgaaga tctgctttta catgcgagac acatcttcta | 720 |
| aagtaatttt aataatagtt actatattca agatttcata tatcaaatac tcaatattac | 780 |
| ttctaaaaaa ttaattagat ataattaaaa tattactttt ttaattttaa gtttaattgt | 840 |
| tgaatttgtg actattgatt tattattcta ctatgtttaa attgttttat agatagttta | 900 |
| aagtaaatat aagtaatgta gtagagtgtt agagtgttac cctaaaccat aaactataac | 960 |
| atttatggtg gactaatttt catatatttc ttattgcttt tacctttttct tggtatgtaa | 1020 |
| gtccgtaact agaattacag tgggttgcca tgacactctg tggtcttttg gttcatgcat | 1080 |
| gggtcttgcg caagaaaaag acaaagaaca agaaaaaaag acaaaacaga gagacaaaac | 1140 |
| gcaatcacac aaccaactca aattagtcac tggctgatca agatcgccgc gtccatgtat | 1200 |
| gtctaaatgc catgcaaagc aacacgtgct aacatgcac tttaaatggc tcacccatct | 1260 |
| caacccacac acaaacacat tgccttttttc ttcatcatca ccacaaccac ctgtatatat | 1320 |
| tcattctctt ccgccacctc aatttcttca cttcaacaca cgtcaacctg catatgcgtg | 1380 |
| tcatcccatg cccaaatctc catgcatgtt ccaaccacct tctctcttat ataataccta | 1440 |
| taaataccctc taatatcact cacttctttc atcatccatc catccagagt actactactc | 1500 |

| | | |
|---|---|---|
| tactactata ataccccaac ccaactcata ttcaatacta ctctacc atg gtc tta | | 1556 |
| | Met Val Leu | |
| | 1 | |
| cgt cct gta gaa acc cca acc cgt gaa atc aaa aaa ctc gac ggc ctg | | 1604 |
| Arg Pro Val Glu Thr Pro Thr Arg Glu Ile Lys Lys Leu Asp Gly Leu | | |
| 5             10                  15 | | |
| tgg gca ttc agt ctg gat cgc gaa aac tgt gga att gat cag cgt tgg | | 1652 |
| Trp Ala Phe Ser Leu Asp Arg Glu Asn Cys Gly Ile Asp Gln Arg Trp | | |
| 20             25              30               35 | | |
| tgg gaa agc gcg tta caa gaa agc cgg gca att gct gtg cca ggc agt | | 1700 |
| Trp Glu Ser Ala Leu Gln Glu Ser Arg Ala Ile Ala Val Pro Gly Ser | | |
|         40               45                 50 | | |
| ttt aac gat cag ttc gcc gat gca gat att cgt aat tat gcg ggc aac | | 1748 |
| Phe Asn Asp Gln Phe Ala Asp Ala Asp Ile Arg Asn Tyr Ala Gly Asn | | |

-continued

|  |  |  |  |  |  |  |  |  |  |  |  |  |  |  |  |
|---|---|---|---|---|---|---|---|---|---|---|---|---|---|---|---|
|  |  | 55 |  |  |  |  | 60 |  |  |  |  | 65 |  |  |  |

```
gtc tgg tat cag cgc gaa gtc ttt ata ccg aaa ggt tgg gca ggc cag      1796
Val Trp Tyr Gln Arg Glu Val Phe Ile Pro Lys Gly Trp Ala Gly Gln
         70                  75                  80 cgt atc gtg ctg cgt ttc gat gcg gtc act cat tac ggc aaa gtg tgg      1844
Arg Ile Val Leu Arg Phe Asp Ala Val Thr His Tyr Gly Lys Val Trp
 85                  90                  95 gtc aat aat cag gaa gtg atg gag cat cag ggc ggc tat acg cca ttt      1892
Val Asn Asn Gln Glu Val Met Glu His Gln Gly Gly Tyr Thr Pro Phe
100                 105                 110                 115 gaa gcc gat gtc acg ccg tat gtt att gcc ggg aaa agt gta cgt atc      1940
Glu Ala Asp Val Thr Pro Tyr Val Ile Ala Gly Lys Ser Val Arg Ile
                120                 125                 130 acc gtt tgt gtg aac aac gaa ctg aac tgg cag act atc ccg ccg gga      1988
Thr Val Cys Val Asn Asn Glu Leu Asn Trp Gln Thr Ile Pro Pro Gly
            135                 140                 145 atg gtg att acc gac gaa aac ggc aag aaa aag cag tct tac ttc cat      2036
Met Val Ile Thr Asp Glu Asn Gly Lys Lys Lys Gln Ser Tyr Phe His
        150                 155                 160 gat ttc ttt aac tat gcc gga atc cat cgc agc gta atg ctc tac acc      2084
Asp Phe Phe Asn Tyr Ala Gly Ile His Arg Ser Val Met Leu Tyr Thr
    165                 170                 175 acg ccg aac acc tgg gtg gac gat atc acc gtg gtg acg cat gtc gcg      2132
Thr Pro Asn Thr Trp Val Asp Asp Ile Thr Val Val Thr His Val Ala
180                 185                 190                 195 caa gac tgt aac cac gcg tct gtt gac tgg cag gtg gtg gcc aat ggt      2180
Gln Asp Cys Asn His Ala Ser Val Asp Trp Gln Val Val Ala Asn Gly
                200                 205                 210 gat gtc agc gtt gaa ctg cgt gat gcg gat caa cag gtg gtt gca act      2228
Asp Val Ser Val Glu Leu Arg Asp Ala Asp Gln Gln Val Val Ala Thr
            215                 220                 225 gga caa ggc act agc ggg act ttg caa gtg gtg aat ccg cac ctc tgg      2276
Gly Gln Gly Thr Ser Gly Thr Leu Gln Val Val Asn Pro His Leu Trp
        230                 235                 240 caa ccg ggt gaa ggt tat ctc tat gaa ctg tgc gtc aca gcc aaa agc      2324
Gln Pro Gly Glu Gly Tyr Leu Tyr Glu Leu Cys Val Thr Ala Lys Ser
    245                 250                 255 cag aca gag tgt gat atc tac ccg ctt cgc gtc ggc atc cgg tca gtg      2372
Gln Thr Glu Cys Asp Ile Tyr Pro Leu Arg Val Gly Ile Arg Ser Val
260                 265                 270                 275 gca gtg aag ggc caa cag ttc ctg att aac cac aaa ccg ttc tac ttt      2420
Ala Val Lys Gly Gln Gln Phe Leu Ile Asn His Lys Pro Phe Tyr Phe
                280                 285                 290 act ggc ttt ggt cgt cat gaa gat gcg gac tta cgt ggc aaa gga ttc      2468
Thr Gly Phe Gly Arg His Glu Asp Ala Asp Leu Arg Gly Lys Gly Phe
            295                 300                 305 gat aac gtg ctg atg gtg cac gac cac gca tta atg gac tgg att ggg      2516
Asp Asn Val Leu Met Val His Asp His Ala Leu Met Asp Trp Ile Gly
        310                 315                 320 gcc aac tcc tac cgt acc tcg cat tac cct tac gct gaa gag atg ctc      2564
Ala Asn Ser Tyr Arg Thr Ser His Tyr Pro Tyr Ala Glu Glu Met Leu
    325                 330                 335 gac tgg gca gat gaa cat ggc atc gtg gtg att gat gaa act gct gct      2612
Asp Trp Ala Asp Glu His Gly Ile Val Val Ile Asp Glu Thr Ala Ala
340                 345                 350                 355 gtc ggc ttt tcg ctc tct tta ggc att ggt ttc gaa gcg ggc aac aag      2660
Val Gly Phe Ser Leu Ser Leu Gly Ile Gly Phe Glu Ala Gly Asn Lys
                360                 365                 370 ccg aaa gaa ctg tac agc gaa gag gca gtc aac ggg gaa act cag caa      2708
```

```
                Pro Lys Glu Leu Tyr Ser Glu Ala Val Asn Gly Glu Thr Gln Gln
                            375                 380                 385 gcg cac tta cag gcg att aaa gag ctg ata gcg cgt gac aaa aac cac        2756
Ala His Leu Gln Ala Ile Lys Glu Leu Ile Ala Arg Asp Lys Asn His
        390                 395                 400 cca agc gtg gtg atg tgg agt att gcc aac gaa ccg gat acc cgt ccg        2804
Pro Ser Val Val Met Trp Ser Ile Ala Asn Glu Pro Asp Thr Arg Pro
405                 410                 415 caa ggt gca cgg gaa tat ttc gcg cca ctg gcg gaa gca acg cgt aaa        2852
Gln Gly Ala Arg Glu Tyr Phe Ala Pro Leu Ala Glu Ala Thr Arg Lys
420                 425                 430                 435 ctc gac ccg acg cgt ccg atc acc tgc gtc aat gta atg ttc tgc gac        2900
Leu Asp Pro Thr Arg Pro Ile Thr Cys Val Asn Val Met Phe Cys Asp
                440                 445                 450 gct cac acc gat acc atc agc gat ctc ttt gat gtg ctg tgc ctg aac        2948
Ala His Thr Asp Thr Ile Ser Asp Leu Phe Asp Val Leu Cys Leu Asn
            455                 460                 465 cgt tat tac gga tgg tat gtc caa agc ggc gat ttg gaa acg gca gag        2996
Arg Tyr Tyr Gly Trp Tyr Val Gln Ser Gly Asp Leu Glu Thr Ala Glu
        470                 475                 480 aag gta ctg gaa aaa gaa ctt ctg gcc tgg cag gag aaa ctg cat cag        3044
Lys Val Leu Glu Lys Glu Leu Leu Ala Trp Gln Glu Lys Leu His Gln
485                 490                 495 ccg att atc atc acc gaa tac ggc gtg gat acg tta gcc ggg ctg cac        3092
Pro Ile Ile Ile Thr Glu Tyr Gly Val Asp Thr Leu Ala Gly Leu His
500                 505                 510                 515 tca atg tac acc gac atg tgg agt gaa gag tat cag tgt gca tgg ctg        3140
Ser Met Tyr Thr Asp Met Trp Ser Glu Glu Tyr Gln Cys Ala Trp Leu
                520                 525                 530 gat atg tat cac cgc gtc ttt gat cgc gtc agc gcc gtc gtc ggt gaa        3188
Asp Met Tyr His Arg Val Phe Asp Arg Val Ser Ala Val Val Gly Glu
            535                 540                 545 cag gta tgg aat ttc gcc gat ttt gcg acc tcg caa ggc ata ttg cgc        3236
Gln Val Trp Asn Phe Ala Asp Phe Ala Thr Ser Gln Gly Ile Leu Arg
        550                 555                 560 gtt ggc ggt aac aag aaa ggg atc ttc act cgc gac cgc aaa ccg aag        3284
Val Gly Gly Asn Lys Lys Gly Ile Phe Thr Arg Asp Arg Lys Pro Lys
565                 570                 575 tcg gcg gct ttt ctg ctg caa aaa cgc tgg act ggc atg aac ttc ggt        3332
Ser Ala Ala Phe Leu Leu Gln Lys Arg Trp Thr Gly Met Asn Phe Gly
580                 585                 590                 595 gaa aaa ccg cag cag gga ggc aaa caa tgaatcaaca actctcctgg              3379
Glu Lys Pro Gln Gln Gly Gly Lys Gln
                600 cgcaccatcg tcggctacag cctcggtgga attcgatatc aagcttaaat aagtatgaac      3439 taaaatgcat gtaggtgtaa gagctcatgg agagcatgga atattgtatc cgaccatgta      3499 acagtataat aactgagctc catctcactt cttctatgaa taaacaaagg atgttatgat      3559 atattaacac tctatctatg caccttattg ttctatgata aatttcctct tattattata      3619 aatcatctga atcgtgacgg cttatggaat gcttcaaata gtacaaaaac aaatgtgtac      3679 tataagactt tctaaacaat tctaacttta gcattgtgaa cgagacataa gtgttaagaa      3739 gacataacaa ttataatgga agaagtttgt ctccatttat atattatata ttacccactt      3799 atgtattata ttaggatgtt aaggagacat aacaattata aagagagaag tttgtatcca      3859 tttatatatt atatactacc catttatata ttatacttat ccacttattt aatgtctttt      3919 taaggtttga tccatgatat ttctaatatt ttagttgata tgtatatgaa aggtactat       3979
```

```
ttgaactctc ttactctgta taaaggttgg atcatcctta aagtgggtct atttaatttt    4039
attgcttctt acagataaaa aaaaaattat gagttggttt gataaaatat tgaaggattt    4099
aaaataataa taaataataa ataacatata atatatgtat ataaatttat tataatataa    4159
catttatcta taaaaaagta atattgtca taaatctata caatcgttta gccttgctgg     4219
acgactctca attatttaaa cgagagtaaa catatttgac tttttggtta tttaacaaat    4279
tattatttaa cactatatga aatttttttt ttttatcggc aaggaaataa aattaaatta    4339
ggagggacaa tggtgtgtcc caatccttat acaaccaact tccacaggaa ggtcaggtcg    4399
gggacaacaa aaaacaggc aagggaaatt ttttaatttg ggttgtcttg tttgctgcat     4459
aatttatgca gtaaaacact acacataacc cttttagcag tagagcaatg gttgaccgtg    4519
tgcttagctt ctttttatttt attttttttat cagcaaagaa taaataaaat aaaatgagac  4579
acttcaggga tgtttcaacc cttatacaaa accccaaaaa caagtttcct agcaccctac    4639
caactaaggt acc                                                       4652
```

<210> SEQ ID NO 37
<211> LENGTH: 604
<212> TYPE: PRT
<213> ORGANISM: Artificial Sequence
<220> FEATURE:
<223> OTHER INFORMATION: Phas-GUS-phas

<400> SEQUENCE: 37

```
Met Val Leu Arg Pro Val Glu Thr Pro Thr Arg Glu Ile Lys Lys Leu
1               5                   10                  15

Asp Gly Leu Trp Ala Phe Ser Leu Asp Arg Glu Asn Cys Gly Ile Asp
            20                  25                  30

Gln Arg Trp Trp Glu Ser Ala Leu Gln Glu Ser Arg Ala Ile Ala Val
        35                  40                  45

Pro Gly Ser Phe Asn Asp Gln Phe Ala Asp Ala Asp Ile Arg Asn Tyr
    50                  55                  60

Ala Gly Asn Val Trp Tyr Gln Arg Glu Val Phe Ile Pro Lys Gly Trp
65                  70                  75                  80

Ala Gly Gln Arg Ile Val Leu Arg Phe Asp Ala Val Thr His Tyr Gly
                85                  90                  95

Lys Val Trp Val Asn Asn Gln Glu Val Met Glu His Gln Gly Gly Tyr
            100                 105                 110

Thr Pro Phe Glu Ala Asp Val Thr Pro Tyr Val Ile Ala Gly Lys Ser
        115                 120                 125

Val Arg Ile Thr Val Cys Val Asn Asn Glu Leu Asn Trp Gln Thr Ile
    130                 135                 140

Pro Pro Gly Met Val Ile Thr Asp Glu Asn Gly Lys Lys Lys Gln Ser
145                 150                 155                 160

Tyr Phe His Asp Phe Phe Asn Tyr Ala Gly Ile His Arg Ser Val Met
                165                 170                 175

Leu Tyr Thr Thr Pro Asn Thr Trp Val Asp Asp Ile Thr Val Val Thr
            180                 185                 190

His Val Ala Gln Asp Cys Asn His Ala Ser Val Asp Trp Gln Val Val
        195                 200                 205

Ala Asn Gly Asp Val Ser Val Glu Leu Arg Asp Ala Asp Gln Gln Val
    210                 215                 220

Val Ala Thr Gly Gln Gly Thr Ser Gly Thr Leu Gln Val Val Asn Pro
225                 230                 235                 240
```

-continued

His Leu Trp Gln Pro Gly Glu Gly Tyr Leu Tyr Glu Leu Cys Val Thr
              245                 250                 255

Ala Lys Ser Gln Thr Glu Cys Asp Ile Tyr Pro Leu Arg Val Gly Ile
          260                 265                 270

Arg Ser Val Ala Val Lys Gly Gln Gln Phe Leu Ile Asn His Lys Pro
      275                 280                 285

Phe Tyr Phe Thr Gly Phe Gly Arg His Glu Asp Ala Asp Leu Arg Gly
  290                 295                 300

Lys Gly Phe Asp Asn Val Leu Met Val His Asp His Ala Leu Met Asp
305                 310                 315                 320

Trp Ile Gly Ala Asn Ser Tyr Arg Thr Ser His Tyr Pro Tyr Ala Glu
              325                 330                 335

Glu Met Leu Asp Trp Ala Asp Glu His Gly Ile Val Val Ile Asp Glu
          340                 345                 350

Thr Ala Ala Val Gly Phe Ser Leu Ser Leu Gly Ile Gly Phe Glu Ala
      355                 360                 365

Gly Asn Lys Pro Lys Glu Leu Tyr Ser Glu Glu Ala Val Asn Gly Glu
  370                 375                 380

Thr Gln Gln Ala His Leu Gln Ala Ile Lys Glu Leu Ile Ala Arg Asp
385                 390                 395                 400

Lys Asn His Pro Ser Val Val Met Trp Ser Ile Ala Asn Glu Pro Asp
              405                 410                 415

Thr Arg Pro Gln Gly Ala Arg Glu Tyr Phe Ala Pro Leu Ala Glu Ala
          420                 425                 430

Thr Arg Lys Leu Asp Pro Thr Arg Pro Ile Thr Cys Val Asn Val Met
      435                 440                 445

Phe Cys Asp Ala His Thr Asp Thr Ile Ser Asp Leu Phe Asp Val Leu
  450                 455                 460

Cys Leu Asn Arg Tyr Tyr Gly Trp Tyr Val Gln Ser Gly Asp Leu Glu
465                 470                 475                 480

Thr Ala Glu Lys Val Leu Glu Lys Glu Leu Leu Ala Trp Gln Glu Lys
              485                 490                 495

Leu His Gln Pro Ile Ile Ile Thr Glu Tyr Gly Val Asp Thr Leu Ala
          500                 505                 510

Gly Leu His Ser Met Tyr Thr Asp Met Trp Ser Glu Glu Tyr Gln Cys
      515                 520                 525

Ala Trp Leu Asp Met Tyr His Arg Val Phe Asp Arg Val Ser Ala Val
  530                 535                 540

Val Gly Glu Gln Val Trp Asn Phe Ala Asp Phe Ala Thr Ser Gln Gly
545                 550                 555                 560

Ile Leu Arg Val Gly Gly Asn Lys Lys Gly Ile Phe Thr Arg Asp Arg
              565                 570                 575

Lys Pro Lys Ser Ala Ala Phe Leu Leu Gln Lys Arg Trp Thr Gly Met
          580                 585                 590

Asn Phe Gly Glu Lys Pro Gln Gln Gly Gly Lys Gln
  595                 600

<210> SEQ ID NO 38
<211> LENGTH: 5418
<212> TYPE: DNA
<213> ORGANISM: Artificial Sequence
<220> FEATURE:
<223> OTHER INFORMATION: phas-oleo GUS-phas
<221> NAME/KEY: CDS
<222> LOCATION: (1555)..(1908)
<223> OTHER INFORMATION:

-continued

```
<221> NAME/KEY: CDS
<222> LOCATION: (2149)..(4125)
<223> OTHER INFORMATION:

<400> SEQUENCE: 38
```

| | | |
|---|---|---|
| ctgcaggaat tcattgtact cccagtatca ttatagtgaa agttttggct ctctcgccgg | 60 |
| tggtttttta cctctattta aagggttttt ccacctaaaa attctggtat cattctcact | 120 |
| ttacttgtta ctttaatttc tcataatctt tggttgaaat tatcacgctt ccgcacacga | 180 |
| tatccctaca aatttattat ttgttaaaca ttttcaaacc gcataaaatt ttatgaagtc | 240 |
| ccgtctatct ttaatgtagt ctaacatttt catattgaaa tatataattt acttaatttt | 300 |
| agcgttggta gaaagcataa tgatttattc ttattcttct tcatataaat gtttaatata | 360 |
| caatataaac aaattcttta ccttaagaag gatttcccat tttatatttt aaaaatatat | 420 |
| ttatcaaata tttttcaacc acgtaaatct cataataata agttgtttca aaagtaataa | 480 |
| aatttaactc cataattttt ttattcgact gatcttaaag caacacccag tgacacaact | 540 |
| agccattttt ttctttgaat aaaaaaatcc aattatcatt gtattttttt tatacaatga | 600 |
| aaatttcacc aaacaatcat ttgtggtatt tctgaagcaa gtcatgttat gcaaaattct | 660 |
| ataattccca tttgacacta cggaagtaac tgaagatctg cttttacatg cgagacacat | 720 |
| cttctaaagt aattttaata atagttacta tattcaagat ttcatatatc aaatactcaa | 780 |
| tattacttct aaaaaattaa ttagatataa ttaaaatatt acttttttaa ttttaagttt | 840 |
| aattgttgaa tttgtgacta ttgatttatt attctactat gtttaaattg ttttatagat | 900 |
| agtttaaagt aaatataagt aatgtagtag agtgttagag tgttacccta aaccataaac | 960 |
| tataagattt atggtggact aattttcata tatttcttat tgcttttacc ttttcttggt | 1020 |
| atgtaagtcc gtaactggaa ttactgtggg ttgccatggc actctgtggt cttttggttc | 1080 |
| atgcatggat gcttgcgcaa gaaaagaca agaacaaag aaaaagaca aaacagagag | 1140 |
| acaaaacgca atcacacaac caactcaaat tagtcactgg ctgatcaaga tcgccgcgtc | 1200 |
| catgtatgtc taaatgccat gcaaagcaac acgtgcttaa catgcacttt aaatggctca | 1260 |
| cccatctcaa cccacacaca aacacattgc cttttcttc atcatcacca caaccacctg | 1320 |
| tatatattca ttctcttccg ccacctcaat ttcttcactt caacacacgt caacctgcat | 1380 |
| atgcgtgtca tcccatgccc aaatctccat gcatgttcca accaccttct ctcttatata | 1440 |
| atacctataa atacctctaa tatcactcac ttctttcatc atccatccat ccagagtact | 1500 |
| actactctac tactataata ccccaaccca actcatattc aatactactc tact atg | 1557 |
| | Met |
| | 1 |
| gcg gat aca gct aga gga acc cat cac gat atc atc ggc aga gac cag | 1605 |
| Ala Asp Thr Ala Arg Gly Thr His His Asp Ile Ile Gly Arg Asp Gln | |
|         5                  10                 15 | |
| tac ccg atg atg ggc cga gac cga gac cag tac cag atg tcc gga cga | 1653 |
| Tyr Pro Met Met Gly Arg Asp Arg Asp Gln Tyr Gln Met Ser Gly Arg | |
|             20                  25               30 | |
| gga tct gac tac tcc aag tct agg cag att gct aaa gct gca act gct | 1701 |
| Gly Ser Asp Tyr Ser Lys Ser Arg Gln Ile Ala Lys Ala Ala Thr Ala | |
| 35                  40                  45 | |
| gtc aca gct ggt ggt tcc ctc ctt gtt ctc tcc agc ctt acc ctt gtt | 1749 |
| Val Thr Ala Gly Gly Ser Leu Leu Val Leu Ser Ser Leu Thr Leu Val | |
| 50                  55                  60               65 | |
| gga act gtc ata gct ttg act gtt gca aca cct ctg ctc gtt atc ttc | 1797 |
| Gly Thr Val Ile Ala Leu Thr Val Ala Thr Pro Leu Leu Val Ile Phe | |
|                   70                  75               80 | |

```
agc cca atc ctt gtc ccg gct ctc atc aca gtt gca ctc ctc atc acc      1845
Ser Pro Ile Leu Val Pro Ala Leu Ile Thr Val Ala Leu Leu Ile Thr
        85                  90                  95 ggt ttt ctt tcc tct gga ggg ttt ggc att gcc gct ata acc gtt ttc      1893
Gly Phe Leu Ser Ser Gly Gly Phe Gly Ile Ala Ala Ile Thr Val Phe
    100                 105                 110 tct tgg att tac aag taagcacaca tttatcatct tacttcataa ttttgtgcaa      1948
Ser Trp Ile Tyr Lys
        115 tatgtgcatg catgtgttga gccagtagct ttggatcaat ttttttggtc gaataacaaa    2008 tgtaacaata agaaattgca aattctaggg aacatttggt taactaaata cgaaatttga    2068 cctagctagc ttgaatgtgt ctgtgtatat catctatata ggtaaaatgc ttggtatgat    2128 acctattgat tgtgaatagg tac gca acg gga gag cac cca cag gga tca gac    2181
                      Tyr Ala Thr Gly Glu His Pro Gln Gly Ser Asp
                                  120                 125 aag ttg gac agt gca agg atg aag ttg gga agc aaa gct cag gat ctg      2229
Lys Leu Asp Ser Ala Arg Met Lys Leu Gly Ser Lys Ala Gln Asp Leu
130                 135                 140                 145 aaa gac aga gct cag tac tac gga cag caa cat act ggt ggg gaa cat      2277
Lys Asp Arg Ala Gln Tyr Tyr Gly Gln Gln His Thr Gly Gly Glu His
                150                 155                 160 gac cgt gac cgt act cgt ggt ggc cag cac act acc atg gtc tta cgt      2325
Asp Arg Asp Arg Thr Arg Gly Gly Gln His Thr Thr Met Val Leu Arg
            165                 170                 175 cct gta gaa acc cca acc cgt gaa atc aaa aaa ctc gac ggc ctg tgg      2373
Pro Val Glu Thr Pro Thr Arg Glu Ile Lys Lys Leu Asp Gly Leu Trp
        180                 185                 190 gca ttc agt ctg gat cgc gaa aac tgt gga att gat cag cgt tgg tgg      2421
Ala Phe Ser Leu Asp Arg Glu Asn Cys Gly Ile Asp Gln Arg Trp Trp
    195                 200                 205 gaa agc gcg tta caa gaa agc cgg gca att gct gtg cca ggc agt ttt      2469
Glu Ser Ala Leu Gln Glu Ser Arg Ala Ile Ala Val Pro Gly Ser Phe
210                 215                 220                 225 aac gat cag ttc gcc gat gca gat att cgt aat tat gcg ggc aac gtc      2517
Asn Asp Gln Phe Ala Asp Ala Asp Ile Arg Asn Tyr Ala Gly Asn Val
                230                 235                 240 tgg tat cag cgc gaa gtc ttt ata ccg aaa ggt tgg gca ggc cag cgt      2565
Trp Tyr Gln Arg Glu Val Phe Ile Pro Lys Gly Trp Ala Gly Gln Arg
            245                 250                 255 atc gtg ctg cgt ttc gat gcg gtc act cat tac ggc aaa gtg tgg gtc      2613
Ile Val Leu Arg Phe Asp Ala Val Thr His Tyr Gly Lys Val Trp Val
        260                 265                 270 aat aat cag gaa gtg atg gag cat cag ggc ggc tat acg cca ttt gaa      2661
Asn Asn Gln Glu Val Met Glu His Gln Gly Gly Tyr Thr Pro Phe Glu
    275                 280                 285 gcc gat gtc acg ccg tat gtt att gcc ggg aaa agt gta cgt atc acc      2709
Ala Asp Val Thr Pro Tyr Val Ile Ala Gly Lys Ser Val Arg Ile Thr
290                 295                 300                 305 gtt tgt gtg aac aac gaa ctg aac tgg cag act atc ccg ccg gga atg      2757
Val Cys Val Asn Asn Glu Leu Asn Trp Gln Thr Ile Pro Pro Gly Met
                310                 315                 320 gtg att acc gac gaa aac ggc aag aaa aag cag tct tac ttc cat gat      2805
Val Ile Thr Asp Glu Asn Gly Lys Lys Lys Gln Ser Tyr Phe His Asp
            325                 330                 335 ttc ttt aac tat gcc gga atc cat cgc agc gta atg ctc tac acc acg      2853
Phe Phe Asn Tyr Ala Gly Ile His Arg Ser Val Met Leu Tyr Thr Thr
        340                 345                 350
```

```
                                          -continued ccg aac acc tgg gtg gac gat atc acc gtg gtg acg cat gtc gcg caa    2901
Pro Asn Thr Trp Val Asp Asp Ile Thr Val Val Thr His Val Ala Gln
    355                 360                 365 gac tgt aac cac gcg tct gtt gac tgg cag gtg gtg gcc aat ggt gat    2949
Asp Cys Asn His Ala Ser Val Asp Trp Gln Val Val Ala Asn Gly Asp
370                 375                 380                 385 gtc agc gtt gaa ctg cgt gat gcg gat caa cag gtg gtt gca act gga    2997
Val Ser Val Glu Leu Arg Asp Ala Asp Gln Gln Val Val Ala Thr Gly
                390                 395                 400 caa ggc act agc ggg act ttg caa gtg gtg aat ccg cac ctc tgg caa    3045
Gln Gly Thr Ser Gly Thr Leu Gln Val Val Asn Pro His Leu Trp Gln
            405                 410                 415 ccg ggt gaa ggt tat ctc tat gaa ctg tgc gtc aca gcc aaa agc cag    3093
Pro Gly Glu Gly Tyr Leu Tyr Glu Leu Cys Val Thr Ala Lys Ser Gln
        420                 425                 430 aca gag tgt gat atc tac ccg ctt cgc gtc ggc atc cgg tca gtg gca    3141
Thr Glu Cys Asp Ile Tyr Pro Leu Arg Val Gly Ile Arg Ser Val Ala
    435                 440                 445 gtg aag ggc caa cag ttc ctg att aac cac aaa ccg ttc tac ttt act    3189
Val Lys Gly Gln Gln Phe Leu Ile Asn His Lys Pro Phe Tyr Phe Thr
450                 455                 460                 465 ggc ttt ggt cgt cat gaa gat gcg gac tta cgt ggc aaa gga ttc gat    3237
Gly Phe Gly Arg His Glu Asp Ala Asp Leu Arg Gly Lys Gly Phe Asp
                470                 475                 480 aac gtg ctg atg gtg cac gac cac gca tta atg gac tgg att ggg gcc    3285
Asn Val Leu Met Val His Asp His Ala Leu Met Asp Trp Ile Gly Ala
            485                 490                 495 aac tcc tac cgt acc tcg cat tac cct tac gct gaa gag atg ctc gac    3333
Asn Ser Tyr Arg Thr Ser His Tyr Pro Tyr Ala Glu Glu Met Leu Asp
        500                 505                 510 tgg gca gat gaa cat ggc atc gtg gtg att gat gaa act gct gct gtc    3381
Trp Ala Asp Glu His Gly Ile Val Val Ile Asp Glu Thr Ala Ala Val
    515                 520                 525 ggc ttt tcg ctc tct tta ggc att ggt ttc gaa gcg ggc aac aag ccg    3429
Gly Phe Ser Leu Ser Leu Gly Ile Gly Phe Glu Ala Gly Asn Lys Pro
530                 535                 540                 545 aaa gaa ctg tac agc gaa gag gca gtc aac ggg gaa act cag caa gcg    3477
Lys Glu Leu Tyr Ser Glu Glu Ala Val Asn Gly Glu Thr Gln Gln Ala
                550                 555                 560 cac tta cag gcg att aaa gag ctg ata gcg cgt gac aaa aac cac cca    3525
His Leu Gln Ala Ile Lys Glu Leu Ile Ala Arg Asp Lys Asn His Pro
            565                 570                 575 agc gtg gtg atg tgg agt att gcc aac gaa ccg gat acc cgt ccg caa    3573
Ser Val Val Met Trp Ser Ile Ala Asn Glu Pro Asp Thr Arg Pro Gln
        580                 585                 590 ggt gca cgg gaa tat ttc gcg cca ctg gcg gaa gca acg cgt aaa ctc    3621
Gly Ala Arg Glu Tyr Phe Ala Pro Leu Ala Glu Ala Thr Arg Lys Leu
    595                 600                 605 gac ccg acg cgt ccg atc acc tgc gtc aat gta atg ttc tgc gac gct    3669
Asp Pro Thr Arg Pro Ile Thr Cys Val Asn Val Met Phe Cys Asp Ala
610                 615                 620                 625 cac acc gat acc atc agc gat ctc ttt gat gtg ctg tgc ctg aac cgt    3717
His Thr Asp Thr Ile Ser Asp Leu Phe Asp Val Leu Cys Leu Asn Arg
                630                 635                 640 tat tac gga tgg tat gtc caa agc ggc gat ttg gaa acg gca gag aag    3765
Tyr Tyr Gly Trp Tyr Val Gln Ser Gly Asp Leu Glu Thr Ala Glu Lys
            645                 650                 655 gta ctg gaa aaa gaa ctt ctg gcc tgg cag gag aaa ctg cat cag ccg    3813
Val Leu Glu Lys Glu Leu Leu Ala Trp Gln Glu Lys Leu His Gln Pro
        660                 665                 670
```

```
att atc atc acc gaa tac ggc gtg gat acg tta gcc ggg ctg cac tca      3861
Ile Ile Ile Thr Glu Tyr Gly Val Asp Thr Leu Ala Gly Leu His Ser
        675                 680                 685 atg tac acc gac atg tgg agt gaa gag tat cag tgt gca tgg ctg gat      3909
Met Tyr Thr Asp Met Trp Ser Glu Glu Tyr Gln Cys Ala Trp Leu Asp
690                 695                 700                 705 atg tat cac cgc gtc ttt gat cgc gtc agc gcc gtc gtc ggt gaa cag      3957
Met Tyr His Arg Val Phe Asp Arg Val Ser Ala Val Val Gly Glu Gln
                710                 715                 720 gta tgg aat ttc gcc gat ttt gcg acc tcg caa ggc ata ttg cgc gtt      4005
Val Trp Asn Phe Ala Asp Phe Ala Thr Ser Gln Gly Ile Leu Arg Val
            725                 730                 735 ggc ggt aac aag aaa ggg atc ttc act cgc gac cgc aaa ccg aag tcg      4053
Gly Gly Asn Lys Lys Gly Ile Phe Thr Arg Asp Arg Lys Pro Lys Ser
        740                 745                 750 gcg gct ttt ctg ctg caa aaa cgc tgg act ggc atg aac ttc ggt gaa      4101
Ala Ala Phe Leu Leu Gln Lys Arg Trp Thr Gly Met Asn Phe Gly Glu
    755                 760                 765 aaa ccg cag cag gga ggc aaa caa tgaatcaaca actctcctgg cgcaccatcg     4155
Lys Pro Gln Gln Gly Gly Lys Gln
770                 775 tcggctacag cctcggtgga attcgatatc aagcttaaat aagtatgaac taaaatgcat    4215
gtaggtgtaa gagctcatgg agagcatgga atattgtatc cgaccatgta acagtataat    4275
aactgagctc catctcactt cttctatgaa taaacaaagg atgttatgat atattaacac    4335
tctatctatg caccttattg ttctatgata aatttcctct tattattata aatcatctga    4395
atcgtgacgg cttatggaat gcttcaaata gtacaaaaac aaatgtgtac tataagactt    4455
tctaaacaat tctaacttta gcattgtgaa cgagacataa gtgttaagaa gacataacaa    4515
ttataatgga agaagtttgt ctccatttat atattatata ttacccactt atgtattata    4575
ttaggatgtt aaggagacat aacaattata agagagaag tttgtatcca tttatatatt    4635
atatactacc catttatata ttatacttat ccacttattt aatgtcttta taaggtttga    4695
tccatgatat ttctaatatt ttagttgata tgtatatgaa agggtactat ttgaactctc    4755
ttactctgta taaaggttgg atcatcctta aagtgggtct atttaatttt attgcttctt    4815
acagataaaa aaaaaattat gagttggttt gataaaaaat tgaaggattt aaaataataa    4875
taaataataa ataacatata atatatgtat ataaatttat tataatataa catttatcta    4935
taaaaaagta aatattgtca taaatctata caatcgttta gccttgctgg acgactctca    4995
attatttaaa cgagagtaaa catatttgac tttttggtta tttaacaaat tattatttaa    5055
cactatatga aattttttt ttttatcggc aaggaaataa aattaaatta ggagggacaa     5115
tggtgtgtcc caatccttat acaaccaact tccacaggaa ggtcaggtcg gggacaacaa    5175
aaaaacaggc aagggaaatt ttttaatttg ggttgtcttg tttgctgcat aattttatgca   5235 gtaaaacact acacataacc cttttagcag tagagcaatg gttgaccgtg tgcttagctt    5295
cttttatttt atttttttat cagcaaagaa taaataaaat aaaatgagac acttcaggga    5355
tgtttcaacc cttatacaaa accccaaaaa caagtttcct agcaccctac caactaaggt    5415
acc                                                                   5418
```

<210> SEQ ID NO 39
<211> LENGTH: 118
<212> TYPE: PRT
<213> ORGANISM: Artificial Sequence
<220> FEATURE:

<223> OTHER INFORMATION: phas-oleo GUS-phas

<400> SEQUENCE: 39

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
            115

<210> SEQ ID NO 40
<211> LENGTH: 659
<212> TYPE: PRT
<213> ORGANISM: Artificial Sequence
<220> FEATURE:
<223> OTHER INFORMATION: phas-oleo GUS-phas

<400> SEQUENCE: 40

Tyr Ala Thr Gly Glu His Pro Gln Gly Ser Asp Lys Leu Asp Ser Ala
1               5                   10                  15

Arg Met Lys Leu Gly Ser Lys Ala Gln Asp Leu Lys Asp Arg Ala Gln
            20                  25                  30

Tyr Tyr Gly Gln Gln His Thr Gly Glu His Asp Arg Asp Arg Thr
        35                  40                  45

Arg Gly Gly Gln His Thr Thr Met Val Leu Arg Pro Val Glu Thr Pro
    50                  55                  60

Thr Arg Glu Ile Lys Lys Leu Asp Gly Leu Trp Ala Phe Ser Leu Asp
65                  70                  75                  80

Arg Glu Asn Cys Gly Ile Asp Gln Arg Trp Trp Glu Ser Ala Leu Gln
                85                  90                  95

Glu Ser Arg Ala Ile Ala Val Pro Gly Ser Phe Asn Asp Gln Phe Ala
            100                 105                 110

Asp Ala Asp Ile Arg Asn Tyr Ala Gly Asn Val Trp Tyr Gln Arg Glu
        115                 120                 125

Val Phe Ile Pro Lys Gly Trp Ala Gly Gln Arg Ile Val Leu Arg Phe
    130                 135                 140

Asp Ala Val Thr His Tyr Gly Lys Val Trp Val Asn Asn Gln Glu Val
145                 150                 155                 160

Met Glu His Gln Gly Gly Tyr Thr Pro Phe Glu Ala Asp Val Thr Pro
                165                 170                 175

Tyr Val Ile Ala Gly Lys Ser Val Arg Ile Thr Val Cys Val Asn Asn
            180                 185                 190

Glu Leu Asn Trp Gln Thr Ile Pro Pro Gly Met Val Ile Thr Asp Glu
        195                 200                 205

Asn Gly Lys Lys Lys Gln Ser Tyr Phe His Asp Phe Asn Tyr Ala
    210                 215                 220

```
Gly Ile His Arg Ser Val Met Leu Tyr Thr Thr Pro Asn Thr Trp Val
225                 230                 235                 240

Asp Asp Ile Thr Val Val Thr His Val Ala Gln Asp Cys Asn His Ala
            245                 250                 255

Ser Val Asp Trp Gln Val Val Ala Asn Gly Asp Val Ser Val Glu Leu
                260                 265                 270

Arg Asp Ala Asp Gln Gln Val Val Ala Thr Gly Gln Gly Thr Ser Gly
            275                 280                 285

Thr Leu Gln Val Val Asn Pro His Leu Trp Gln Pro Gly Glu Gly Tyr
        290                 295                 300

Leu Tyr Glu Leu Cys Val Thr Ala Lys Ser Gln Thr Glu Cys Asp Ile
305                 310                 315                 320

Tyr Pro Leu Arg Val Gly Ile Arg Ser Val Ala Val Lys Gly Gln Gln
                325                 330                 335

Phe Leu Ile Asn His Lys Pro Phe Tyr Phe Thr Gly Phe Gly Arg His
            340                 345                 350

Glu Asp Ala Asp Leu Arg Gly Lys Gly Phe Asp Asn Val Leu Met Val
            355                 360                 365

His Asp His Ala Leu Met Asp Trp Ile Gly Ala Asn Ser Tyr Arg Thr
        370                 375                 380

Ser His Tyr Pro Tyr Ala Glu Glu Met Leu Asp Trp Ala Asp Glu His
385                 390                 395                 400

Gly Ile Val Val Ile Asp Glu Thr Ala Ala Val Gly Phe Ser Leu Ser
                405                 410                 415

Leu Gly Ile Gly Phe Glu Ala Gly Asn Lys Pro Lys Glu Leu Tyr Ser
            420                 425                 430

Glu Glu Ala Val Asn Gly Glu Thr Gln Gln Ala His Leu Gln Ala Ile
        435                 440                 445

Lys Glu Leu Ile Ala Arg Asp Lys Asn His Pro Ser Val Val Met Trp
450                 455                 460

Ser Ile Ala Asn Glu Pro Asp Thr Arg Pro Gln Gly Ala Arg Glu Tyr
465                 470                 475                 480

Phe Ala Pro Leu Ala Glu Ala Thr Arg Lys Leu Asp Pro Thr Arg Pro
                485                 490                 495

Ile Thr Cys Val Asn Val Met Phe Cys Asp Ala His Thr Asp Thr Ile
            500                 505                 510

Ser Asp Leu Phe Asp Val Leu Cys Leu Asn Arg Tyr Tyr Gly Trp Tyr
        515                 520                 525

Val Gln Ser Gly Asp Leu Glu Thr Ala Glu Lys Val Leu Glu Lys Glu
530                 535                 540

Leu Leu Ala Trp Gln Glu Lys Leu His Gln Pro Ile Ile Ile Thr Glu
545                 550                 555                 560

Tyr Gly Val Asp Thr Leu Ala Gly Leu His Ser Met Tyr Thr Asp Met
                565                 570                 575

Trp Ser Glu Glu Tyr Gln Cys Ala Trp Leu Asp Met Tyr His Arg Val
            580                 585                 590

Phe Asp Arg Val Ser Ala Val Val Gly Glu Gln Val Trp Asn Phe Ala
        595                 600                 605

Asp Phe Ala Thr Ser Gln Gly Ile Leu Arg Val Gly Gly Asn Lys Lys
    610                 615                 620

Gly Ile Phe Thr Arg Asp Arg Lys Pro Lys Ser Ala Ala Phe Leu Leu
625                 630                 635                 640
```

Gln Lys Arg Trp Thr Gly Met Asn Phe Gly Glu Lys Pro Gln Gln Gly
            645                 650                 655
Gly Lys Gln

<210> SEQ ID NO 41
<211> LENGTH: 5390
<212> TYPE: DNA
<213> ORGANISM: Artificial Sequence
<220> FEATURE:
<223> OTHER INFORMATION: phas-caleo-GUS-phas
<221> NAME/KEY: CDS
<222> LOCATION: (1548)..(4097)
<223> OTHER INFORMATION:

<400> SEQUENCE: 41

| | | | | | |
|---|---|---|---|---|---|
| gaattcattg | tactcccagt | atcattatag | tgaaagtttt | ggctctctcg | ccggtggttt | 60 |
| tttacctcta | tttaaagggg | ttttccacct | aaaaattctg | gtatcattct | cactttactt | 120 |
| gttactttaa | tttctcataa | tctttggttg | aaattatcac | gcttccgcac | acgatatccc | 180 |
| tacaaattta | ttatttgtta | aacattttca | aaccgcataa | aattttatga | agtcccgtct | 240 |
| atctttaatg | tagtctaaca | ttttcatatt | gaaatatata | atttacttaa | ttttagcgtt | 300 |
| ggtagaaagc | ataagatttt | attcttattc | ttcttcatat | aaatgtttaa | tatacaatat | 360 |
| aaacaaattc | tttaccttaa | gaaggatttc | ccattttata | ttttaaaaat | atatttatca | 420 |
| aatattttc | aaccacgtaa | atctcataat | aataagttgt | ttcaaaagta | ataaaattta | 480 |
| actccataat | ttttttattc | gactgatctt | aaagcaacac | ccagtgacac | aactagccat | 540 |
| tttttttcttt | gaataaaaaa | atccaattat | cattgtattt | ttttttataca | atgaaaattt | 600 |
| caccaaacaa | tcatttgtgg | tatttctgaa | gcaagtcatg | ttatgcaaaa | ttctataatt | 660 |
| cccatttgac | actacggaag | taactgaaga | tctgctttta | catgcgagac | acatcttcta | 720 |
| aagtaatttt | aataatagtt | actatattca | agatttcata | tatcaaatac | tcaatattac | 780 |
| ttctaaaaaa | ttaattagat | ataattaaaa | tattacttttt | ttaatttaaa | gtttaattgt | 840 |
| tgaatttgtg | actattgatt | tattattcta | ctatgtttaa | attgttttat | agatagttta | 900 |
| aagtaaatat | aagtaatgta | gtagagtgtt | agagtgttac | cctaaaccat | aaactataac | 960 |
| atttatggtg | gactaatttt | catatatttc | ttattgcttt | taccttttct | tggtatgtaa | 1020 |
| gtccgtaact | agaattacag | tgggttgcca | tgacactctg | tggtcttttg | gttcatgcat | 1080 |
| gggtcttgcg | caagaaaaag | acaaagaaca | aagaaaaaag | acaaaacaga | gagacaaaac | 1140 |
| gcaatcacac | aaccaactca | aattagtcac | tggctgatca | agatcgccgc | gtccatgtat | 1200 |
| gtctaaatgc | catgcaaagc | aacacgtgct | taacatgcac | tttaaatggc | tcacccatct | 1260 |
| caacccacac | acaaacacat | tgcctttttc | ttcatcatca | ccacaaccac | ctgtatatat | 1320 |
| tcattctctt | ccgccacctc | aatttcttca | cttcaacaca | cgtcaacctg | catatgcgtg | 1380 |
| tcatcccatg | cccaaatctc | catgcatgtt | ccaaccacct | tctctcttat | ataataccta | 1440 |
| taaatacctc | taatatcact | cacttctttc | atcatccatc | catccagagt | actactactc | 1500 | tactactata atccccaac ccaactcata ttcaatacta ctctacc atg ggg tca   1556
                                                 Met Gly Ser
                                                  1 aag acg gag atg atg gag aga gac gca atg gct acg gtg gct ccc tat   1604
Lys Thr Glu Met Met Glu Arg Asp Ala Met Ala Thr Val Ala Pro Tyr
  5                  10                  15 gcg ccg gtc act tac cac cgc cgt gct cgt gtt gac ttg gat gat aga   1652
Ala Pro Val Thr Tyr His Arg Arg Ala Arg Val Asp Leu Asp Asp Arg
 20                  25                  30                  35

-continued

| | |
|---|---|
| ctt cct aaa cct tat atg cca aga gca ttg caa gca cca gac aga gaa<br>Leu Pro Lys Pro Tyr Met Pro Arg Ala Leu Gln Ala Pro Asp Arg Glu<br>            40                    45                    50 | 1700 |
| cac ccg tac gga act cca ggc cat aag aat tac gga ctt agt gtt ctt<br>His Pro Tyr Gly Thr Pro Gly His Lys Asn Tyr Gly Leu Ser Val Leu<br>            55                    60                    65 | 1748 |
| caa cag cat gtc tcc ttc ttc gat atc gat gat aat ggc atc att tac<br>Gln Gln His Val Ser Phe Phe Asp Ile Asp Asp Asn Gly Ile Ile Tyr<br>            70                    75                    80 | 1796 |
| cct tgg gag acc tac tct gga ctg cga atg ctt ggt ttc aat atc att<br>Pro Trp Glu Thr Tyr Ser Gly Leu Arg Met Leu Gly Phe Asn Ile Ile<br>85                    90                    95 | 1844 |
| ggg tcg ctt ata ata gcc gct gtt atc aac ctg acc ctt agc tat gcc<br>Gly Ser Leu Ile Ile Ala Ala Val Ile Asn Leu Thr Leu Ser Tyr Ala<br>100                  105                110           115 | 1892 |
| act ctt ccg ggg tgg tta cct tca cct ttc ttc cct ata tac ata cac<br>Thr Leu Pro Gly Trp Leu Pro Ser Pro Phe Phe Pro Ile Tyr Ile His<br>                    120                    125                130 | 1940 |
| aac ata cac aag tca aag cat gga agt gat tca aaa aca tat gac aat<br>Asn Ile His Lys Ser Lys His Gly Ser Asp Ser Lys Thr Tyr Asp Asn<br>            135                    140                    145 | 1988 |
| gaa gga agg ttt atg ccg gtg aat ctt gag ttg ata ttt agc aaa tat<br>Glu Gly Arg Phe Met Pro Val Asn Leu Glu Leu Ile Phe Ser Lys Tyr<br>                150                  155                    160 | 2036 |
| gcg aaa acc ttg cca gac aag ttg agt ctt gga gaa cta tgg gag atg<br>Ala Lys Thr Leu Pro Asp Lys Leu Ser Leu Gly Glu Leu Trp Glu Met<br>165                    170                175 | 2084 |
| aca gaa gga aac cgt gac gct tgg gac att ttt gga tgg atc gca ggc<br>Thr Glu Gly Asn Arg Asp Ala Trp Asp Ile Phe Gly Trp Ile Ala Gly<br>180                  185                190           195 | 2132 |
| aaa ata gag tgg gga ctg ttg tac ttg cta gca agg gat gaa gaa ggg<br>Lys Ile Glu Trp Gly Leu Leu Tyr Leu Leu Ala Arg Asp Glu Glu Gly<br>                    200                    205                210 | 2180 |
| ttt ttg tca aaa gaa gct att agg cgg tgt ttc gat gga agc ttg ttc<br>Phe Leu Ser Lys Glu Ala Ile Arg Arg Cys Phe Asp Gly Ser Leu Phe<br>            215                    220                    225 | 2228 |
| gag tac tgt gcc aaa atc tac gct ggt atc agt gaa gac aag aca gca<br>Glu Tyr Cys Ala Lys Ile Tyr Ala Gly Ile Ser Glu Asp Lys Thr Ala<br>              230                  235                    240 | 2276 |
| tac tac gcc atg gtc tta cgt cct gta gaa acc cca acc cgt gaa atc<br>Tyr Tyr Ala Met Val Leu Arg Pro Val Glu Thr Pro Thr Arg Glu Ile<br>245                    250                255 | 2324 |
| aaa aaa ctc gac ggc ctg tgg gca ttc agt ctg gat cgc gaa aac tgt<br>Lys Lys Leu Asp Gly Leu Trp Ala Phe Ser Leu Asp Arg Glu Asn Cys<br>260                  265                270           275 | 2372 |
| gga att gat cag cgt tgg tgg gaa agc gcg tta caa gaa agc cgg gca<br>Gly Ile Asp Gln Arg Trp Trp Glu Ser Ala Leu Gln Glu Ser Arg Ala<br>                280                  285                    290 | 2420 |
| att gct gtg cca ggc agt ttt aac gat cag ttc gcc gat gca gat att<br>Ile Ala Val Pro Gly Ser Phe Asn Asp Gln Phe Ala Asp Ala Asp Ile<br>                295                  300                  305 | 2468 |
| cgt aat tat gcg ggc aac gtc tgg tat cag cgc gaa gtc ttt ata ccg<br>Arg Asn Tyr Ala Gly Asn Val Trp Tyr Gln Arg Glu Val Phe Ile Pro<br>          310                    315                    320 | 2516 |
| aaa ggt tgg gca ggc cag cgt atc gtg ctg cgt ttc gat gcg gtc act<br>Lys Gly Trp Ala Gly Gln Arg Ile Val Leu Arg Phe Asp Ala Val Thr<br>325                    330                335 | 2564 |
| cat tac ggc aaa gtg tgg gtc aat aat cag gaa gtg atg gag cat cag<br>His Tyr Gly Lys Val Trp Val Asn Asn Gln Glu Val Met Glu His Gln | 2612 |

```
                340             345             350             355
ggc ggc tat acg cca ttt gaa gcc gat gtc acg ccg tat gtt att gcc    2660
Gly Gly Tyr Thr Pro Phe Glu Ala Asp Val Thr Pro Tyr Val Ile Ala
                360                 365                 370 ggg aaa agt gta cgt atc acc gtt tgt gtg aac aac gaa ctg aac tgg    2708
Gly Lys Ser Val Arg Ile Thr Val Cys Val Asn Asn Glu Leu Asn Trp
            375                 380                 385 cag act atc ccg ccg gga atg gtg att acc gac gaa aac ggc aag aaa    2756
Gln Thr Ile Pro Pro Gly Met Val Ile Thr Asp Glu Asn Gly Lys Lys
            390                 395                 400 aag cag tct tac ttc cat gat ttc ttt aac tat gcc gga atc cat cgc    2804
Lys Gln Ser Tyr Phe His Asp Phe Phe Asn Tyr Ala Gly Ile His Arg
        405                 410                 415 agc gta atg ctc tac acc acg ccg aac acc tgg gtg gac gat atc acc    2852
Ser Val Met Leu Tyr Thr Thr Pro Asn Thr Trp Val Asp Asp Ile Thr
420                 425                 430                 435 gtg gtg acg cat gtc gcg caa gac tgt aac cac gcg tct gtt gac tgg    2900
Val Val Thr His Val Ala Gln Asp Cys Asn His Ala Ser Val Asp Trp
                440                 445                 450 cag gtg gtg gcc aat ggt gat gtc agc gtt gaa ctg cgt gat gcg gat    2948
Gln Val Val Ala Asn Gly Asp Val Ser Val Glu Leu Arg Asp Ala Asp
                455                 460                 465 caa cag gtg gtt gca act gga caa ggc act agc ggg act ttg caa gtg    2996
Gln Gln Val Val Ala Thr Gly Gln Gly Thr Ser Gly Thr Leu Gln Val
            470                 475                 480 gtg aat ccg cac ctc tgg caa ccg ggt gaa ggt tat ctc tat gaa ctg    3044
Val Asn Pro His Leu Trp Gln Pro Gly Glu Gly Tyr Leu Tyr Glu Leu
        485                 490                 495 tgc gtc aca gcc aaa agc cag aca gag tgt gat atc tac ccg ctt cgc    3092
Cys Val Thr Ala Lys Ser Gln Thr Glu Cys Asp Ile Tyr Pro Leu Arg
500                 505                 510                 515 gtc ggc atc cgg tca gtg gca gtg aag ggc caa cag ttc ctg att aac    3140
Val Gly Ile Arg Ser Val Ala Val Lys Gly Gln Gln Phe Leu Ile Asn
                520                 525                 530 cac aaa ccg ttc tac ttt act ggc ttt ggt cgt cat gaa gat gcg gac    3188
His Lys Pro Phe Tyr Phe Thr Gly Phe Gly Arg His Glu Asp Ala Asp
            535                 540                 545 tta cgt ggc aaa gga ttc gat aac gtg ctg atg gtg cac gac cac gca    3236
Leu Arg Gly Lys Gly Phe Asp Asn Val Leu Met Val His Asp His Ala
        550                 555                 560 tta atg gac tgg att ggg gcc aac tcc tac cgt acc tcg cat tac cct    3284
Leu Met Asp Trp Ile Gly Ala Asn Ser Tyr Arg Thr Ser His Tyr Pro
565                 570                 575 tac gct gaa gag atg ctc gac tgg gca gat gaa cat ggc atc gtg gtg    3332
Tyr Ala Glu Glu Met Leu Asp Trp Ala Asp Glu His Gly Ile Val Val
580                 585                 590                 595 att gat gaa act gct gct gtc ggc ttt tcg ctc tct tta ggc att ggt    3380
Ile Asp Glu Thr Ala Ala Val Gly Phe Ser Leu Ser Leu Gly Ile Gly
                600                 605                 610 ttc gaa gcg ggc aac aag ccg aaa gaa ctg tac agc gaa gag gca gtc    3428
Phe Glu Ala Gly Asn Lys Pro Lys Glu Leu Tyr Ser Glu Glu Ala Val
            615                 620                 625 aac ggg gaa act cag caa gcg cac tta cag gcg att aaa gag ctg ata    3476
Asn Gly Glu Thr Gln Gln Ala His Leu Gln Ala Ile Lys Glu Leu Ile
            630                 635                 640 gcg cgt gac aaa aac cac cca agc gtg gtg atg tgg agt att gcc aac    3524
Ala Arg Asp Lys Asn His Pro Ser Val Val Met Trp Ser Ile Ala Asn
        645                 650                 655 gaa ccg gat acc cgt ccg caa ggt gca cgg gaa tat ttc gcg cca ctg    3572
```

```
Glu Pro Asp Thr Arg Pro Gln Gly Ala Arg Glu Tyr Phe Ala Pro Leu
660             665                 670                 675 gcg gaa gca acg cgt aaa ctc gac ccg acg cgt ccg atc acc tgc gtc        3620
Ala Glu Ala Thr Arg Lys Leu Asp Pro Thr Arg Pro Ile Thr Cys Val
                    680                 685                 690 aat gta atg ttc tgc gac gct cac acc gat acc atc agc gat ctc ttt        3668
Asn Val Met Phe Cys Asp Ala His Thr Asp Thr Ile Ser Asp Leu Phe
                695                 700                 705 gat gtg ctg tgc ctg aac cgt tat tac gga tgg tat gtc caa agc ggc        3716
Asp Val Leu Cys Leu Asn Arg Tyr Tyr Gly Trp Tyr Val Gln Ser Gly
            710                 715                 720 gat ttg gaa acg gca gag aag gta ctg gaa aaa gaa ctt ctg gcc tgg        3764
Asp Leu Glu Thr Ala Glu Lys Val Leu Glu Lys Glu Leu Leu Ala Trp
        725                 730                 735 cag gag aaa ctg cat cag ccg att atc atc acc gaa tac ggc gtg gat        3812
Gln Glu Lys Leu His Gln Pro Ile Ile Ile Thr Glu Tyr Gly Val Asp
740             745                 750                 755 acg tta gcc ggg ctg cac tca atg tac acc gac atg tgg agt gaa gag        3860
Thr Leu Ala Gly Leu His Ser Met Tyr Thr Asp Met Trp Ser Glu Glu
                760                 765                 770 tat cag tgt gca tgg ctg gat atg tat cac cgc gtc ttt gat cgc gtc        3908
Tyr Gln Cys Ala Trp Leu Asp Met Tyr His Arg Val Phe Asp Arg Val
                775                 780                 785 agc gcc gtc gtc ggt gaa cag gta tgg aat ttc gcc gat ttt gcg acc        3956
Ser Ala Val Val Gly Glu Gln Val Trp Asn Phe Ala Asp Phe Ala Thr
            790                 795                 800 tcg caa ggc ata ttg cgc gtt ggc ggt aac aag aaa ggg atc ttc act        4004
Ser Gln Gly Ile Leu Arg Val Gly Gly Asn Lys Lys Gly Ile Phe Thr
        805                 810                 815 cgc gac cgc aaa ccg aag tcg gcg gct ttt ctg ctg caa aaa cgc tgg        4052
Arg Asp Arg Lys Pro Lys Ser Ala Ala Phe Leu Leu Gln Lys Arg Trp
820             825                 830                 835 act ggc atg aac ttc ggt gaa aaa ccg cag cag gga ggc aaa caa            4097
Thr Gly Met Asn Phe Gly Glu Lys Pro Gln Gln Gly Gly Lys Gln
                840                 845                 850
```
tgaatcaaca actctcctgg cgcaccatcg tcggctacag cctcggtgga attcgatatc        4157
aagcttaaat aagtatgaac taaaatgcat gtaggtgtaa gagctcatgg agagcatgga        4217
atattgtatc cgaccatgta acagtataat aactgagctc catctcactt cttctatgaa        4277
taaacaaagg atgttatgat atattaacac tctatctatg caccttattg ttctatgata        4337
aatttcctct tattattata aatcatctga atcgtgacgg cttatggaat gcttcaaata        4397
gtacaaaaac aaatgtgtac tataagactt tctaaacaat tctaacttta gcattgtgaa        4457
cgagacataa gtgttaagaa gacataacaa ttataatgga agaagtttgt ctccatttat        4517
atattatata ttacccactt atgtattata ttaggatgtt aaggagacat aacaattata        4577
aagagagaag tttgtatcca tttatatatt atatactacc catttatata ttatacttat        4637
ccacttattt aatgtcttta taaggtttga tccatgatat ttctaatatt ttagttgata        4697
tgtatatgaa agggtactat ttgaactctc ttactctgta taaaggttgg atcatcctta        4757
aagtgggtct atttaatttt attgcttctt acagataaaa aaaaaattat gagttggttt        4817 gataaaaatat tgaaggattt aaaataataa taaataataa ataacatata atatatgtat        4877
ataaatttat tataatataa catttatcta taaaaaagta aatattgtca taaatctata        4937
caatcgttta gccttgctgg acgactctca attatttaaa cgagagtaaa catatttgac        4997
tttttggtta tttaacaaat tattatttaa cactatatga aatttttttt ttttatcggc        5057

-continued

```
aaggaaataa aattaaatta ggagggacaa tggtgtgtcc caatccttat acaaccaact      5117
tccacaggaa ggtcaggtcg gggacaacaa aaaaacaggc aagggaaatt ttttaatttg      5177
ggttgtcttg tttgctgcat aatttatgca gtaaaacact acacataacc cttttagcag      5237
tagagcaatg gttgaccgtg tgcttagctt cttttatttt attttttat cagcaaagaa       5297 taaataaaat aaaatgagac acttcaggga tgtttcaacc cttatacaaa accccaaaaa      5357
caagtttcct agcaccctac caactaaggt acc                                    5390
```

<210> SEQ ID NO 42
<211> LENGTH: 850
<212> TYPE: PRT
<213> ORGANISM: Artificial Sequence
<220> FEATURE:
<223> OTHER INFORMATION: phas-caleo-GUS-phas

<400> SEQUENCE: 42

```
Met Gly Ser Lys Thr Glu Met Met Glu Arg Asp Ala Met Ala Thr Val
  1               5                  10                  15

Ala Pro Tyr Ala Pro Val Thr Tyr His Arg Arg Ala Arg Val Asp Leu
             20                  25                  30

Asp Asp Arg Leu Pro Lys Pro Tyr Met Pro Arg Ala Leu Gln Ala Pro
         35                  40                  45

Asp Arg Glu His Pro Tyr Gly Thr Pro His Lys Asn Tyr Gly Leu
     50                  55                  60

Ser Val Leu Gln Gln His Val Ser Phe Phe Asp Ile Asp Asp Asn Gly
 65                  70                  75                  80

Ile Ile Tyr Pro Trp Glu Thr Tyr Ser Gly Leu Arg Met Leu Gly Phe
                 85                  90                  95

Asn Ile Ile Gly Ser Leu Ile Ile Ala Ala Val Ile Asn Leu Thr Leu
            100                 105                 110

Ser Tyr Ala Thr Leu Pro Gly Trp Leu Pro Ser Pro Phe Phe Pro Ile
        115                 120                 125

Tyr Ile His Asn Ile His Lys Ser Lys His Gly Ser Asp Ser Lys Thr
    130                 135                 140

Tyr Asp Asn Glu Gly Arg Phe Met Pro Val Asn Leu Glu Leu Ile Phe
145                 150                 155                 160

Ser Lys Tyr Ala Lys Thr Leu Pro Asp Lys Leu Ser Leu Gly Glu Leu
                165                 170                 175

Trp Glu Met Thr Glu Gly Asn Arg Asp Ala Trp Asp Ile Phe Gly Trp
            180                 185                 190

Ile Ala Gly Lys Ile Glu Trp Gly Leu Leu Tyr Leu Leu Ala Arg Asp
        195                 200                 205

Glu Glu Gly Phe Leu Ser Lys Glu Ala Ile Arg Arg Cys Phe Asp Gly
    210                 215                 220

Ser Leu Phe Glu Tyr Cys Ala Lys Ile Tyr Ala Gly Ile Ser Glu Asp
225                 230                 235                 240

Lys Thr Ala Tyr Tyr Ala Met Val Leu Arg Pro Val Glu Thr Pro Thr
                245                 250                 255

Arg Glu Ile Lys Lys Leu Asp Gly Leu Trp Ala Phe Ser Leu Asp Arg
            260                 265                 270

Glu Asn Cys Gly Ile Asp Gln Arg Trp Trp Ser Ala Leu Gln Glu
        275                 280                 285

Ser Arg Ala Ile Ala Val Pro Gly Ser Phe Asn Asp Gln Phe Ala Asp
    290                 295                 300
```

-continued

```
Ala Asp Ile Arg Asn Tyr Ala Gly Asn Val Trp Tyr Gln Arg Glu Val
305                 310                 315                 320

Phe Ile Pro Lys Gly Trp Ala Gly Gln Arg Ile Val Leu Arg Phe Asp
                325                 330                 335

Ala Val Thr His Tyr Gly Lys Val Trp Val Asn Asn Gln Glu Val Met
            340                 345                 350

Glu His Gln Gly Gly Tyr Thr Pro Phe Glu Ala Asp Val Thr Pro Tyr
        355                 360                 365

Val Ile Ala Gly Lys Ser Val Arg Ile Thr Val Cys Val Asn Asn Glu
    370                 375                 380

Leu Asn Trp Gln Thr Ile Pro Pro Gly Met Val Ile Thr Asp Glu Asn
385                 390                 395                 400

Gly Lys Lys Lys Gln Ser Tyr Phe His Asp Phe Phe Asn Tyr Ala Gly
                405                 410                 415

Ile His Arg Ser Val Met Leu Tyr Thr Thr Pro Asn Thr Trp Val Asp
            420                 425                 430

Asp Ile Thr Val Val Thr His Val Ala Gln Asp Cys Asn His Ala Ser
        435                 440                 445

Val Asp Trp Gln Val Val Ala Asn Gly Asp Val Ser Val Glu Leu Arg
    450                 455                 460

Asp Ala Asp Gln Gln Val Val Ala Thr Gly Gln Gly Thr Ser Gly Thr
465                 470                 475                 480

Leu Gln Val Val Asn Pro His Leu Trp Gln Pro Gly Glu Gly Tyr Leu
                485                 490                 495

Tyr Glu Leu Cys Val Thr Ala Lys Ser Gln Thr Glu Cys Asp Ile Tyr
            500                 505                 510

Pro Leu Arg Val Gly Ile Arg Ser Val Ala Val Lys Gly Gln Gln Phe
        515                 520                 525

Leu Ile Asn His Lys Pro Phe Tyr Phe Thr Gly Phe Gly Arg His Glu
    530                 535                 540

Asp Ala Asp Leu Arg Gly Lys Gly Phe Asp Asn Val Leu Met Val His
545                 550                 555                 560

Asp His Ala Leu Met Asp Trp Ile Gly Ala Asn Ser Tyr Arg Thr Ser
                565                 570                 575

His Tyr Pro Tyr Ala Glu Glu Met Leu Asp Trp Ala Asp Glu His Gly
            580                 585                 590

Ile Val Val Ile Asp Glu Thr Ala Ala Val Gly Phe Ser Leu Ser Leu
        595                 600                 605

Gly Ile Gly Phe Glu Ala Gly Asn Lys Pro Lys Glu Leu Tyr Ser Glu
    610                 615                 620

Glu Ala Val Asn Gly Glu Thr Gln Gln Ala His Leu Gln Ala Ile Lys
625                 630                 635                 640

Glu Leu Ile Ala Arg Asp Lys Asn His Pro Ser Val Val Met Trp Ser
                645                 650                 655

Ile Ala Asn Glu Pro Asp Thr Arg Pro Gln Gly Ala Arg Glu Tyr Phe
            660                 665                 670

Ala Pro Leu Ala Glu Ala Thr Arg Lys Leu Asp Pro Thr Arg Pro Ile
        675                 680                 685

Thr Cys Val Asn Val Met Phe Cys Asp Ala His Thr Asp Thr Ile Ser
    690                 695                 700

Asp Leu Phe Asp Val Leu Cys Leu Asn Arg Tyr Tyr Gly Trp Tyr Val
705                 710                 715                 720

Gln Ser Gly Asp Leu Glu Thr Ala Glu Lys Val Leu Glu Lys Glu Leu
```

-continued

```
                725                 730                 735
Leu Ala Trp Gln Glu Lys Leu His Gln Pro Ile Ile Ile Thr Glu Tyr
            740                 745                 750

Gly Val Asp Thr Leu Ala Gly Leu His Ser Met Tyr Thr Asp Met Trp
            755                 760                 765

Ser Glu Glu Tyr Gln Cys Ala Trp Leu Asp Met Tyr His Arg Val Phe
            770                 775                 780

Asp Arg Val Ser Ala Val Val Gly Glu Gln Val Trp Asn Phe Ala Asp
785                         790                 795                 800

Phe Ala Thr Ser Gln Gly Ile Leu Arg Val Gly Gly Asn Lys Lys Gly
                805                 810                 815

Ile Phe Thr Arg Asp Arg Lys Pro Lys Ser Ala Ala Phe Leu Leu Gln
            820                 825                 830

Lys Arg Trp Thr Gly Met Asn Phe Gly Glu Lys Pro Gln Gln Gly Gly
            835                 840                 845

Lys Gln
    850
```

PREPARATION OF HETEROLOGOUS PROTEINS ON OIL BODIES

CROSS-REFERENCE TO RELATED APPLICATIONS

The present application is a continuation-in-part of U.S. Ser. No. 09/210,843 that was filed Dec. 18, 1998, now U.S. Pat. No. 6,288,304, issued on Sep. 11, 2001, which is a continuation-in-part of U.S. Ser. No. 08/846,021 that was filed Apr. 25, 1997 (now U.S. Pat. No. 5,948,682), which is a continuation-in-part of U.S. Ser. No. 08/366,783 that was filed on Dec. 30, 1994 (now U.S. Pat. No. 5,650,554), which is a continuation-in-part of U.S. Ser. No. 08/142,418 that was filed Nov. 16, 1993 (now abandoned), which is a continuation-in-part of U.S. Ser. No. 07/659,835 that was filed on Feb. 22, 1991 (now abandoned), all of which are incorporated by reference in their entirety.

FIELD OF THE INVENTION

The present invention relates to novel methods for the preparation of heterologous proteins.

BACKGROUND OF THE INVENTION

Many very diverse methods have been tested for the production of recombinant molecules of interest and commercial value. Different organisms that have been considered as hosts for foreign protein expression include single celled organisms such as bacteria and yeasts, cells and cell cultures of animals, fungi and plants and whole organisms such as plants, insects and transgenic animals.

The use of fermentation techniques for large scale production of bacteria, yeasts and higher organism cell cultures is well established. The capital costs associated with establishment of the facility and the costs of maintenance are negative economic factors. Although the expression levels of proteins that can be achieved are high, energy inputs and protein purification costs can greatly increase the cost of recombinant protein production.

The production of a variety of proteins of therapeutic interest has been described in transgenic animals, however the cost of establishing substantial manufacturing is prohibitive for all but high value proteins. Numerous foreign proteins have been expressed in whole plants and selected plant organs. Methods of stably inserting recombinant DNA into plants have become routine and the number of species that are now accessible to these methods has increased greatly.

Plants represent a highly effective and economical means to produce recombinant proteins as they can be grown on a large scale with modest cost inputs and most commercially important species can now be transformed. Although the expression of foreign proteins has been clearly demonstrated, the development of systems with commercially viable levels of expression coupled with cost effective separation techniques has been limited.

The production of recombinant proteins and peptides in plants has been investigated using a variety of approaches including transcriptional fusions using a strong constitutive plant promoter (e.g., from cauliflower mosaic virus (Sijmons et al., 1990, Bio/Technology, 8:217–221); transcriptional fusions with organ specific promoter sequences (Radke et al., 1988, Theoret. Appl. Genet., 75:685–694); and translational fusions which require subsequent cleavage of a recombinant protein (Vanderkerckove et al., 1989, Bio/Technology, 7:929–932).

Foreign proteins that have been successfully expressed in plant cells include proteins from bacteria (Fraley et al., 1983, Proc. Natl. Acad. Sci. USA, 80:4803–4807), animals (Misra and Gedamu, 1989, Theor. Appl. Genet., 78:161–168), fungi and other plant species (Fraley et al., 1983, Proc. Natl. Acad. Sci. USA, 80:4803–4807). Some proteins, predominantly markers of DNA integration, have been expressed in specific cells and tissues including seeds (Sen Gupta-Gopalan et al., 1985, Proc. Natl. Acad. Sci. USA, 82:3320–3324); Radke et al., 1988, Theor. Appl. Genet., 75:685–694). Seed specific research has been focused on the use of seed-storage protein promoters as a means of deriving seed-specific expression. Using such a system, Vanderkerckove et al., (1989, Bio/Technol., 7:929–932) expressed the peptide leu-enkephalin in seeds of *Arabidopsis thaliana* and *Brassica napus*. The level of expression of this peptide was quite low and it appeared that expression of this peptide was limited to endosperm tissue.

It has been generally shown that the construction of chimeric genes which contain the promoter from a given regulated gene and a coding sequence of a reporter protein not normally associated with that promoter gives rise to regulated expression of the reporter. The use of promoters from seed-specific genes for the expression of recombinant sequences in seed that are not normally expressed in a seed-specific manner have been described.

Sengupta-Gopalan et al., (1985, Proc. Natl. Acad. Sci. USA, 82:3320–3324) reported expression of a major storage protein of french bean, called β-phaseolin, in tobacco plants. The gene expressed correctly in the seeds and only at very low levels elsewhere in the plant. However, the constructs used by Sengupta-Gopalan were not chimeric. The entire β-phaseolin gene including the native 5'-flanking sequences were used. Subsequent experiments with other species (Radke et al., 1988, Theor. App. Genet. 75:685–694) or other genes (Perez-Grau, L., Goldberg, R. B., 1989, Plant Cell, 1:1095–1109) showed the fidelity of expression in a seed-specific manner in both Arabidopsis and Brassica. Radke et al., (1988, vide supra), used a "tagged" gene i.e., one containing the entire napin gene plus a non-translated "tag".

The role of the storage proteins is to serve as a reserve of nitrogen during seed germination and growth. Although storage protein genes can be expressed at high levels, they represent a class of protein whose complete three-dimensional structure appears important for proper packaging and storage. The storage proteins generally assemble into multimeric units which are arranged in specific bodies in endosperm tissue. Perturbation of the structure by the addition of foreign peptide sequences leads to storage proteins unable to be packaged properly in the seed.

In addition to nitrogen, the seed also stores lipids. The storage of lipids occurs in oil or lipid bodies. Analysis of the contents of lipid bodies has demonstrated that in addition to triglyceride and membrane lipids, there are also several polypeptides/proteins associated with the surface or lumen of the oil body (Bowman-Vance and Huang, 1987, J. Biol. Chem., 262:11275–11279, Murphy et al., 1989, Biochem. J., 258:285–293, Taylor et al., 1990, Planta, 181:18–26). Oil-body proteins have been identified in a wide range of taxonomically diverse species (Moreau et al., 1980, Plant Physiol., 65:1176–1180; Qu et al., 1986, Biochem. J., 235:57–65) and have been shown to be uniquely localized in oil-bodies and not found in organelles of vegetative tissues. In *Brassica napus* (rapeseed, canola) there are at least three polypeptides associated with the oil-bodies of developing seeds (Taylor et al., 1990, Planta, 181:18–26).

The oil bodies that are produced in seeds are of a similar size (Huang A. H. C., 1985, in Modern Meths. Plant Analysis, Vol. 1:145–151 Springer-Verlag, Berlin). Electron microscopic observations have shown that the oil-bodies are surrounded by a membrane and are not freely suspended in the cytoplasm. These oil-bodies have been variously named by electron microscopists as oleosomes, lipid bodies and spherosomes (Gurr M I., 1980, in The Biochemistry of Plants, 4:205–248, Acad. Press, Orlando, Fla). The oil-bodies of the species that have been studied are encapsulated by an unusual "half-unit" membrane comprising, not a classical lipid bilayer, but rather a single amphophilic layer with hydrophobic groups on the inside and hydrophillic groups on the outside (Huang A. H. C., 1985, in Modern Meths. Plant Analysis, Vol. 1:145–151 Springer-Verlag, Berlin).

The numbers and sizes of oil-body associated proteins may vary from species to species. In corn, for example, there are two immunologically distinct polypeptide classes found in oil-bodies (Bowman-Vance and Huang, 1988, J. Biol. Chem., 263:1476–1481). Oleosins have been shown to comprise alternate hydrophillic and hydrophobic regions (Bowman-Vance and Huang, 1987, J. Biol. Chem., 262:11275–11279). The amino acid sequences of oleosins from corn, rapeseed, and carrot have been obtained. See Qu and Huang, 1990, J. Biol. Chem., 265:2238–2243, Hatzopoulos et al., 1990, Plant Cell, 2:457–467, respectively. In an oilseed such as rapeseed, oleosin may comprise between 8% (Taylor et al., 1990, Planta, 181:18–26) and 20% (Murphy et al., 1989, Biochem.J., 258:285–293) of total seed protein. Such a level is comparable to that found for many seed storage proteins.

Genomic clones encoding oil-body proteins with their associated upstream regions have been reported for several species, including maize (*Zea mays*, Bowman-Vance and Huang, 1987, J. Biol. Chem., 262:11275–11279; and Qu Huang, 1990, J. Biol. Chem., 265:2238–2243) and carrot (Hatzopoulos et al., 1990, Plant Cell, 2:457–467). cDNAs and genomic clones have also been reported for cultivated oilseeds, *Brassica napus* (Murphy, et al., 1991, Biochem. Biophys. Acta, 1088:86–94; and Lee and Huang, 1991, Plant Physiol 96:1395–1397), sunflower (Cummins and Murphy, 1992, Plant Molec. Biol. 19:873–878) soybean (Kalinski et al., 1991, Plant Molec. Biol. 17: 1095–1098), and cotton (Hughes et al., 1993, Plant Physiol 101:697–698). Reports on the expression of these oil-body protein genes in developing seeds have varied. In the case of *Zea mays*, transcription of genes encoding oil-body protein isoforms began quite early in seed development and were easily detected 18 days after pollination. In non-endospermic seeds such as the dicotyledonous plant *Brassica napus* (canola, rapeseed), expression of oil-body protein genes seems to occur later in seed development (Murphy, et al., 1989, Biochem. J., 258:285–293) compared to corn.

A maize oleosin has been expressed in seed oil bodies in *Brassica napus* transformed with a *Zea mays* oleosin gene. The gene was expressed under the control of regulatory elements from a Brassica gene encoding napin, a major seed storage protein. The temporal regulation and tissue specificity of expression was reported to be correct for a napin gene promoter/terminator (Lee et al., 1991, Proc. Natl. Acad. Sci. USA, 88:6181–6185).

Thus the above demonstrates that oil body proteins (or oleosins) from various plant sources share a number of similarities in both structure and expression. However, at the time of the above references it was generally believed that modifications to oleosins or oil body proteins would likely lead to abherant targeting and instability of the protein product. (Vande Kerckhove et al., 1989. Bio/Technology, 7:929–932; Radke et al., 1988. Theor. and Applied Genetics, 75:685–694; and Hoffman et al., 1988. Plant Mol. Biol. 11:717–729).

SUMMARY OF THE INVENTION

The present invention describes the use of an oil body protein gene to target the expression of a heterologous polypeptide, to an oil body in a host cell. The unique features of both the oil body protein and the expression patterns are used in this invention to provide a means of synthesizing commercially important proteins on a scale that is difficult if not impossible to achieve using conventional systems of protein production.

In particular, the present invention provides a method for the expression of a heterologous polypeptide by a host cell said method comprising: a) introducing into a host cell a chimeric nucleic acid sequence comprising: 1) a first nucleic acid sequence capable of regulating the transcription in said host cell of 2) a second nucleic acid sequence, wherein said second sequence encodes a fusion polypeptide and comprises (i) a nucleic acid sequence encoding a sufficient portion of an oil body protein gene to provide targeting of the fusion polypeptide to a lipid phase linked in reading frame to (ii) a nucleic acid sequence encoding the heterologous polypeptide; and 3) a third nucleic acid sequence encoding a termination region functional in the host cell; and b) growing said host cell to produce the fusion polypeptide.

The present invention also provides a method for the production and release of a heterologous polypeptide from a fusion polypeptide associated with a plant oil body fraction during seed germination and plant seedling growth, said method comprising: a) introducing into a plant cell a first chimeric nucleic acid sequence comprising: 1) a first nucleic acid sequence capable of regulating the transcription in said plant cell of 2) a second nucleic acid sequence wherein said nucleic acid second sequence encodes a fusion polypeptide and comprises (i) a nucleic acid sequence encoding a sufficient portion of an oil body protein gene to provide targeting of the fusion polypeptide to an oil body, linked in reading frame to (ii) a nucleic acid sequence encoding the heterologous polypeptide and (iii) a linker nucleic acid sequence encoding an amino acid sequence that is specifically cleavable by enzymatic means wherein said linker nucleic acid sequence (iii) is located between said nucleic acid sequence (i) encoding the oil body protein and said nucleic acid sequence (ii) encoding the heterologous polypeptide; and 3) a third nucleic acid sequence encoding a termination region; b) sequentially or concomitantly introducing into the genome of said plant a second chimeric nucleic acid sequence comprising: 1) a first nucleic acid sequence capable of regulating the transcription specifically during seed germination and seed growth of 2) a second nucleic acid sequence encoding a specific enzyme that is capable of cleaving the linker nucleic acid sequence of said first chimeric nucleic acid sequence; and 3) a third nucleic acid sequence encoding a termination region; c) regenerating a plant from said plant cell and growing said plant to produce seed whereby said fusion polypeptide is expressed and associated with oil bodies and d) allowing said seed to germinate wherein said enzyme in said second chimeric nucleic acid sequence is expressed and cleaves the heterologous polypeptide from the fusion polypeptide associated with the oil bodies during seed germination and early seedling growth.

The present invention further provides a method for producing an altered seed meal by producing a heterologous polypeptide in association with a plant seed oil body fraction, said method comprising: a) introducing into a plant cell a chimeric nucleic acid sequence comprising: 1) a first nucleic acid sequence capable of regulating the transcription in said plant cell of 2) a second nucleic acid sequence wherein said second sequence encodes a fusion polypeptide and comprises (i) a nucleic acid sequence encoding a sufficient portion of an oil body protein gene to provide targeting of the fusion polypeptide to an oil body, linked in reading frame to (ii) a nucleic acid sequence encoding the heterologous polypeptide and 3) a third nucleic acid sequence encoding a termination region; b) regenerating a plant from said plant cell and growing said plant to produce seed whereby said heterologous polypeptide is expressed and associated with oil bodies; and c) crushing said seed and preparing an altered seed meal.

The present invention yet also provides a method of preparing an enzyme in a host cell in association with an oil body and releasing said enzyme from the oil body, said method comprising: a) transforming a host cell with a chimeric nucleic acid sequence comprising: 1) a first nucleic acid sequence capable of regulating the transcription of 2) a second nucleic acid sequence, wherein said second sequence encodes a fusion polypeptide and comprises (i) a nucleic acid sequence encoding a sufficient portion of an oil body protein gene to provide targeting of the fusion polypeptide to an oil body; (ii) a nucleic acid sequence encoding an enzyme and (iii) a linker nucleic acid sequence located between said nucleic acid sequence (i) encoding the oil body and said nucleic acid sequence (ii) encoding the enzyme and encoding an amino acid sequence that is cleavable by the enzyme encoded by the nucleic acid sequence (ii); and 3) a third nucleic acid sequence encoding a termination region functional in said host cell b) growing the host cell to produce the fusion polypeptide under conditions such that enzyme is not active; c) recovering the oil bodies containing the fusion polypeptide; and d) altering the environment of the oil bodies such that the enzyme is activated and cleaves itself from the fusion polypeptide.

The present invention further provides a method for the expression of a heterologous polypeptide by a host cell in association with an oil body and separating said heterologous polypeptide from the oil body, said method comprising: a) transforming a first host cell with a first chimeric nucleic acid sequence comprising: 1) a first nucleic aic acid sequence capable of regulating the transcription in said host cell of 2) a second nucleic acid sequence, wherein said second sequence encodes a first fusion polypeptide and comprises (i) a nucleic acid sequence encoding a sufficient portion of an oil body protein gene to provide targeting of the first fusion polypeptide to a lipid phase linked in reading frame to (ii) a nucleic acid sequence encoding the heterologous polypeptide; and (iii) a linker nucleic acid sequence encoding an amino acid sequence that is specifically cleavable by enzymatic means wherein said linker nucleic acid sequence (iii) is located between said (i) nucleic acid sequence encoding the oil body protein and said (ii) nucleic acid sequence encoding the heterologous polypeptide; and 3) a third nucleic acid sequence encoding a termination region functional in the host cell; and b) transforming a second host cell with a second chimeric nucleic acid sequence comprising: 1) a first nucleic acid sequence capable of regulating the transcription specifically during seed germination and seed growth of 2) a second nucleic acid sequence wherein said second sequence encodes a second fusion polypeptide and comprises (i) a nucleic acid sequence encoding a sufficient portion of an oil body protein gene to provide targeting of the second fusion polypeptide to a lipid phase linked in reading frame to a nucleic acid sequence, encoding a specific enzyme that is capable of cleaving the linker nucleic acid sequence of said first chimeric nucleic acid sequence; and 3) a third nucleic acid sequence encoding a termination region; c) growing said first host cell under conditions such that the first fusion polypeptide is expressed and associated with the oil bodies to produce a first oil body fraction containing the first recombinant fusion polypeptide; d) growing said second host cell under conditions such that the second fusion polypeptide is expressed and associated with the oil bodies to product a second oil body fraction containing the second recombinant fusion polypeptide; e) contacting the first oil body fraction of step (c) with the second oil body fraction of step (d) under conditions such that the enzyme portion of the second fusion polypeptide cleaves the heterologous polypeptide from the first fusion polypeptide.

The present invention also provides a chimeric nucleic acid sequence encoding a fusion polypeptide, capable of being expressed in association with an oil body of a host cell comprising: 1) a first nucleic acid sequence capable of regulating the transcription in said host cell of 2) a second nucleic acid sequence, wherein said second sequence encodes a fusion polypeptide and comprises (i) a nucleic acid sequence encoding a sufficient portion of an oil body protein gene to provide targeting of the fusion polypeptide to a lipid phase linked in reading frame to (ii) a nucleic acid sequence encoding a heterologous polypeptide; and 3) a third nucleic acid sequence encoding a termination region functional in the host cell.

The present invention also includes a fusion polypeptides encoded for by a chimeric nucleic acid sequence comprising (i) a nucleic acid sequence encoding a sufficient portion of an oil body protein to provide targeting of the fusion polypeptide to an oil body linked in reading frame to (ii) a nucleic acid sequence encoding a heterologous polypeptide.

The invention further provides methods for the separation of heterologous proteins from host cell components by partitioning of the oil body fraction and subsequent release of the heterologous protein via specific cleavage of the heterologous protein—oil body protein fusion. Optionally a cleavage site may be located prior to the N-terminus and after the C-terminus of the heterologous polypeptide allowing the fusion polypeptide to be cleaved and separated by phase separation into its component peptides. This production system finds utility in the production of many proteins and peptides such as those with pharmaceutical, enzymic, rheological and adhesive properties.

The processing of a wide variety of materials using enzymes has enormous commercial potential. The present invention provides for methods to produce recombinant enzymes in mass quantities which can be separated from cellular components by partitioning of the oil-body fraction. The enzyme of interest may be cleaved from the oil body protein or may be used in association with the oil-body fraction. Enzymes fused to an oil body protein in an oil-body fraction represent a type of immobilized and reusable enzyme system. Immobilized enzyme systems have been developed in association with various inert support matrices for many industrial purposes including cellulose beads, plastic matrixes and other types of inert materials. Enzymes attached to oil-bodies can be mixed with solutions containing enzyme substrates and subsequently recovered by floatation and partitioning of the oil-body fraction and reused.

In addition to the production and isolation of recombinant proteins from plants, the present invention also contemplates methods for crop improvement and protection. The nutritional quality of seeds has been improved by the addition of proteins with high levels of essential amino acids (DeClercq et al., 1990, Plant Physiol. 94:970–979) and enzymes such as lauroyl-ACP thioesterase from *Umbellularia californica* that affect lipid composition (U.S. Pat. No. 5,298,421). To date these seed modifications have only been conducted using seed storage gene promoters that may have inherent limitations. Use of oil body protein regulatory sequences provides an additional means by which to accomplish such modifications.

Insect predation and fungal diseases of crop plants represent two of the largest causes of yield losses. A number of strategies dependent on transformation and expression of recombinant proteins in plants have been advanced for the protection of plants from insects and fungi (Lamb et al., 1992, Bio/Technology 11:1436–1445). These strategies are exemplified by the expression of peptide inhibitors of insect digestive enzymes such as cowpea trypsin inhibitor (Hoffman et al., 1992, J. Economic Entomol. 85: 2516–1522) bacterial or arachnid protein toxins (Gordon and Zlotkin, 1993, FEBS Lett., 315:125–128) and the expression of chitinase enzymes for the digestion of fungal cell walls (Broglie et al., 1991, Science 254: 5035, 1194–1197; Benhamou et al., 1993, Plant Journal 2:295–305; Dunsmuir et al., 1993, In Advances in molecular genetics of plant-microbe interactions, Vol2. pp 567–571, Nester, E. W. and Verma, D. P. S. eds.). The use of oil body proteins to localize specific polypeptides that afford crop protection allows one to develop novel strategies to protect vulnerable germinating seeds.

The use of oil body whose expression is limited to pollen allows one to alter the function of pollen to specifically control male fertility. One may use promoter sequences from such oil body to specifically express recombinant proteins that will alter the function of pollen. One such example is the use of such promoters to control the expression of novel recognition proteins such as the self-incompatibility proteins. Additional uses are contemplated including expression of oil body fusion proteins in pollen that are toxic to pollen. Seed specific oil body may be used to alter female fertility.

The methods described above are not limited to heterologous proteins produced in plant seeds as oil body proteins may also be found in association with oil bodies in other cells and tissues. Additionally the methods are not limited to the recovery of heterologous proteins produced in plants because the extraction and release methods can be adapted to accommodate oil body protein-heterologous protein fusions produced in any cell type or organism. An extract containing the fusion protein is mixed with additional oleosins and appropriate tri-glycerides and physical conditions are manipulated to reconstitute the oil-bodies. The reconstituted oil-bodies are separated by floatation and the recombinant proteins released by the cleavage of the junction with oleosin.

BRIEF DESCRIPTION OF THE DRAWINGS

FIG. 2 shows the nucleotide sequence (SEQ ID NO.1) and deduced amino acid sequence (SEQ ID NO.2 and NO. 3) of an oil-body protein gene that codes for a 18 KDa oleosin from *Arabidopsis thaliana*. The intron sequence is printed in lower case. The predicted amino acid sequence is shown in single letter code.

FIG. 4 shows the nucleotide sequence (SEQ ID NO.4) of a *B. napus* oleosin cDNA clone and the predicted amino acid sequence (SEQ ID NO.5).

FIGS. 6A–B shows the nucleotide sequence (SEQ.ID.NO.6) and deduced amino acid (SEQ.ID.NO.7 and NO.8) sequence of the 2.7 kbp HindIII fragment of pSBSOTPTNT containing the oleosin-chymosin fusion gene. Indicated in bold (nt 1625–1631) is the NcoI site containing the methionine start codon of the prochymosin sequence. The preceding spacer sequence (nt 1608–1630), replacing the oleosin stopcodon is underlined.

FIG. 9. Sequence alignment of the isolated caleosin (SEQ ID NO.34) (this application) with the coding sequence of the reported caleosin gene (accession number AF067857) (SEQ ID NO.35). Indicated are the primers GVR979 and GVR980 used for the polymerase Chain Reaction and the one nucleotide change (position 69).

FIGS. 10A–C. Nucleotide sequence of insert of pSBS2098 containing the phaseolin promoter-β Glucuronidase (GUS)-phaseolin terminator sequence (SEQ ID NO.36). The GUS sequence and its deduced amino acid sequence (SEQ ID NO.37) is indicated in uppercase. The phaseolin promoter corresponds to nucleotide 1–1547, and the phaseolin terminator corresponds to nucleotide sequence 3426–4646. The terminator was furnished with a a KpnI site (nt 4647–4652) to facilitate cloning.

FIGS. 11A–C. Nucleotide sequence of the phaseolin promoter-oleosinGUS-phaseolin terminator sequence (SEQ ID NO.38). The oleosinGUS coding sequence and its deduced aminoacid sequence is indicated (SEQ ID NOs.39 and 40). The phaseolin promoter corresponds to nucleotide 6–1554. The sequence encoding oleosin corresponds to nt 1555–2313, the intron in this sequence (nt 1908–2147) is indicated in italics. The GUS sequence corresponds to nt 2314–4191. The phaseolin terminator corresponds to nucleotide sequence 4192–5412.

FIGS. 12A–C. Nucleotide sequence of the phaseolin promoter-caleosinGUS-phaseolin terminator sequence (SEQ ID NO.41). The caleosinGUS coding sequence and its deduced aminoacid sequence is indicated (SEQ ID NO.42). The phaseolin promoter corresponds to nucleotide 1–1545. The sequence encoding caleosin corresponds to nt 1548–2282, the NcoI restriction, which was used for the in-frame cloning and which separates the caleosin and GUS sequence (nt 2284–2289) is underlined. The GUS sequence corresponds to nt 2286–4163. The phaseolin terminator corresponds to nucleotide sequence 4164–5384.

DETAILED DESCRIPTION OF THE INVENTION

Figure 1A:
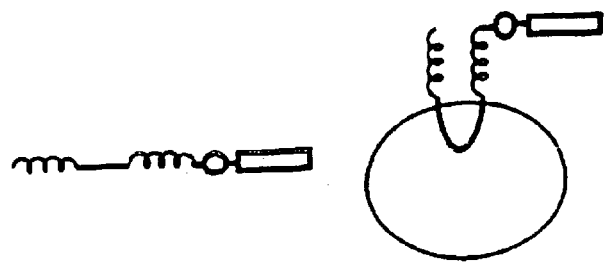
FIGS. 1A–1D show a schematic representation of the types of oil body protein fusions that are contemplated as methods of the invention for the fusion of oil-body protein genes with genes encoding foreign polypeptides. IA is a C-terminal fusion of a desired polypeptide to a oil body protein; IB is an N-terminal fusion of a desired polypeptide to oil body protein; IC is an internal fusion of a desired polypeptide within oil body protein; and ID is an inter-dimer translational fusion of desired polypeptide enclosed between two substantially complete oil body protein targeting sequences. Each fusion is shown in a linear diagrammatic form and in the configuration predicted when specifically associated with the oil body. In both the linear and oil body associated form, the oil body coding sequence that specifically targets the protein to the oil body is shown as a single thin line, a solid circle represents a protease recognition motif; a corkscrew line represents a native C- or N-terminal of a oil body protein and a inserted coding region is represented by an open box. The oil body is represented as a simple circle.
Figure 1B:
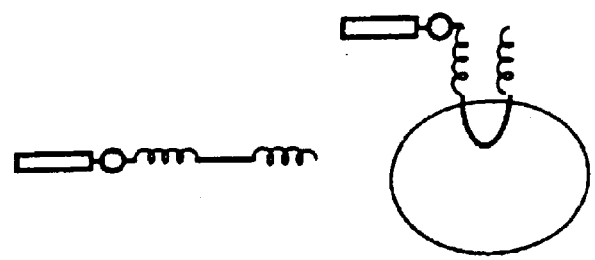
Figure 1C:
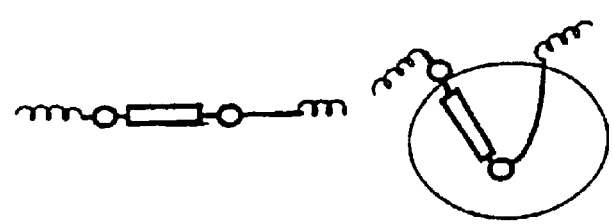
Figure 1D:
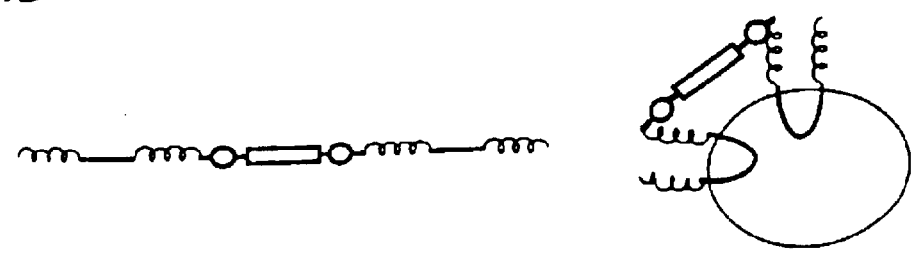

In accordance with the subject invention, methods and compositions are provided for a novel means of production of heterologous proteins and peptides that can be easily separated from host cell components. In accordance with further embodiments of the invention methods and compositions are provided for novel uses of recombinant proteins produced by said methods.

In accordance with one aspect of the subject invention, methods and compositions are provided for a novel means of production of heterologous proteins and peptides in host cells that are easily separated from other host cell components. Purification of the protein, if required, is greatly simplified. The nucleic acid encoding the heterologous peptide may be part or all of a naturally occurring gene from any source, it may be a synthetic nucleic acid sequence or it may be a combination of naturally occurring and synthetic sequences. The subject method includes the steps of preparing an expression cassette comprising a first nucleic acid sequence capable of regulating the transcription of a second nucleic acid sequence encoding a sufficient portion of an oil body protein gene to provide targeting to an oil body and fused to this second nucleic acid sequence a third nucleic acid sequence encoding the polypeptide of interest; delivery and incorporation of the expression cassette into a host cell; production of a transformed organism or cell population in which the chimeric gene product is expressed and recovery of a chimeric gene protein product through specific association with an oil body. The heterologous peptide is generally a foreign polypeptide normally not expressed in the host cell or found in association with the oil-body.

The term "oil body protein" as used herein means a protein that can naturally associate with oil bodies or can be isolated using a standard oil body preparation protocol. An oil body preparation protocol is described in van Rooijen and Moloney, 1995, Bio/Technology, 13:72–77. The oil body protein may share sequence homology with other oil body proteins which may be oleosins or caleosins known in the art.

In one embodiment the oil body protein is a plant oleosin and shares sequence homology with other plant oleosins such as the oleosin isolated from *Arabidopsis thaliana* (FIG. 2 and SEQ.ID.NO:2) or *Brassica napus* (FIG. 4 and SEQ.ID.NO:5). In another embodiment, the oil body protein is a plant caleosin and shares sequence homology with other plant caleosins such as the caleosin isolated from *Arabidopsis thaliana* shown in FIG. 9 (SEQ.ID.NOs.34 and 35)

The term "heterologous polypeptide" as used herein means a polypeptide, peptide or protein that is not normally linked or fused to an oil body protein and is not normally expressed in association with oil bodies.

The term "nucleic acid sequence" refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

The host cell may be selected from a wide range of host cells including plants, bacteria, yeasts, insects and mammals. In one embodiment the host cell is a plant cell. The use of plants to produce proteins of interest allows exploitation of the ability of plants to capture energy and limited nutrient input to make proteins. The scale and yield of material afforded by production in plants allows adaptation of the technology for use in the production of a variety of polypeptides of commercial interest. The plant may be selected from various plant families including Brassicaceae, Compositae, Euphorbiaceae, Leguminosae, Linaceae, Malvaceae, Umbilliferae and Graminae.

In another embodiment the host cell is a bacterial cell. Bacterial host cells suitable for carrying out the present invention include *E. coli, B. subtilis, Salmonella typhimurium* and Staphylococcus, as well as many other bacterial species well known to one of ordinary skill in the art. Representative examples of bacterial host cells include JM109 ATCC No. 53323 and DH5 (Stratagene, LaJolla, Calif.). Suitable bacterial expression vectors preferably comprise a promoter which functions in the host cell, one or more selectable phenotypic markers, and a bacterial origin of replication. Representative promoters include the LacZ, the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20:231, 1982).

In another embodiment, the host cell is a yeast cell. Yeast and fungi host cells suitable for carrying out the present invention include, among others *Saccharomyces cerevisae*, the genera Pichia or Kluyveromyces and various species of the genus Aspergillus. Suitable expression vectors for yeast and fungi include, among others, $YC_p50$ (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

The host cell may also be a mammalian cell. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells.b Suitable expression vectors for directing expression in mammalian cells generally include a promoter, as well as other transcriptional and translational control sequences. Suitable promoters include PMSG, pSVL, SV40, pCH 110, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., Molecular Cloning a Laboratory Manual, 2nd Edition, Cold Spring Harbour Laboratory Press, 1989).

The host cell may also be an insect cell. Insect cells suitable for carrying out the present invention include cells and cell lines from Bombyx or Spodotera species. Suitable expression vectors for directing expression in insect cells include Baculoviruses such as the *Autographa california* nuclear polyhedrosis, virus (Miller et al. 1987, in *Genetic Engineering*, Vol. 8 ed. Setler, J. K. et al., Plenum Press, New York) and the *Bombyx mori* nuclear polyhedrosis virus (Maeda et al., 1985, Nature 315:592).

In one embodiment the host cell is a plant and the chimeric product is expressed and translocated to the oil bodies of the seed.

The use of an oil body protein as a carrier or targeting means provides a simple mechanism to recover proteins. The chimeric protein associated with the oil body or reconstituted oil body fraction is separated away from the bulk of cellular components in a single step (such as centrifugation size exclusion or floatation); the protein is also protected from degradation during extraction as the separation also reduces contact of the proteins with non-specific proteases.

The invention contemplates the use of heterologous proteins, specifically enzymes, fused to oleosins and associated with oil bodies, or reconstituted oil bodies for conversion of substrates in aqueous solutions following mixing of oil body fractions and substrate solutions. Association of the enzyme with the oil body allows subsequent recovery of the enzyme by simple means (centrifugation and floatation) and repeated use thereafter.

In accordance with further embodiments of the invention methods and compositions are provided for the release of heterologous proteins and peptides fused to oleosin proteins specifically associated with isolated oil body or reconstituted oil body fractions. The subject method includes the steps of preparing an expression cassette comprising a first nucleic acid sequence capable of regulating the transcription of a second nucleic acid sequence encoding a sufficient portion of an oil body protein gene such as oleosin to provide targeting to an oil body and fused to this second nucleic acid sequence via a linker nucleic acid sequence encoding a amino acid sequence cleavable by a specific protease or chemical treatment a third nucleic acid sequence encoding the polypeptide of interest; such that the protein of interest can be cleaved from the isolated oil body fraction by the action of said specific chemical or protease.

For embodiments of the invention wherein the cleavage of heterologous proteins fused to oleosins associated with seed oil bodies is contemplated in germinating seed the expression cassette containing the heterologous protein gene so described above is modified to contain an additional second recombinant nucleic acid molecule comprising a first nucleic acid sequence capable of regulating expression in plants, particularly in germinating seed, more specifically seed embryo or other seed tissue containing oil bodies and under the control of this regulatory sequence a nucleic acid sequence encoding a protease enzyme, specifically a particular protease enzyme capable of cleavage of the fusion protein associated with said oil bodies to release a heterologous protein or peptide from the oil body, and a transcriptional and translational termination region functional in plants. It is desirable that the second recombinant nucleic acid molecule be so constructed such that the first and second recombinant nucleic acid sequences are linked by a multiple cloning site to allow for the convenient substitution of any one of a variety of proteolytic enzymes that may be used to cleave fusion proteins associated with oil bodies.

It is obvious to a person skilled in the art of plant molecular biology, genetics or plant breeding that the equivalent to the above modification to the expression cassette to allow release of proteins and peptides of interest in germinating seeds can be accomplished by other similar means. For example it is possible that the first recombinant nucleic acid molecule and the second recombinant nucleic acid molecule described above may be contained within two independent expression cassettes introduced into the genome of a plant independently. Additionally it is possible to sexually cross a first recombinant plant containing the first recombinant nucleic acid molecule integrated into its genome with a second recombinant plant with the second recombinant nucleic acid integrated into its genome to produce seed comprising both the first and second nucleic acid molecules.

For embodiments of the invention wherein the heterologous protein is to be produced in and potentially recovered from plant seeds the expression cassette will generally include, in the 5'-3' direction of transcription, a first recombinant nucleic acid sequence comprising a transcriptional and translational regulatory region capable of expression in plants, particularly in developing seed, more specifically seed embryo or other seed tissue that has oil body or triglyceride storage such as pericarp or cuticle, and a second recombinant nucleic acid sequence encoding a fusion peptide or protein comprising a sufficient portion of an oil body specific protein to provide targeting to an oil body, a heterologous protein of interest, and a transcriptional and translational termination region functional in plants. One or more introns may also be present within the oil body specific protein coding sequence or within the coding sequence of the heterologous protein of interest. The fusion peptide or protein may also comprise a peptide sequence linking the oil body specific portion and the peptide or protein of interest that can be specifically cleaved by chemical or enzymatic means. It is desirable that the nucleic acid expression cassette is constructed in such a fashion that the first and second recombinant nucleic acid sequences are linked by a multiple cloning site to allow for the convenient substitution of alternative second recombinant nucleic acid sequences comprising the oil body targeting sequence and any one of a variety of proteins or peptides of interest to be expressed and targeted to oil bodies in seeds.

According to one embodiment of the invention the expression cassette is introduced into a host cell in a form where the expression cassette is stably incorporated into the genome of the host cell. Accordingly it is apparent that one may also introduce the expression cassette as part of a recombinant nucleic acid sequence capable of replication and or expression in the host cell without the need to become integrated into the host chromosome. Examples of this are found in a variety of vectors such as viral or plasmid vectors capable of replication and expression of proteins in the host cell. One specific example are plasmids that carry an origin of replication that permit high copy number such as the pUC series of *E. Coli* plasmids additionally said plasmids modified to contain an inducible promoter such as the LacZ promoter inducible by galactose or IPTG.

In an alternative embodiment of the invention nucleic acid is stably incorporated into the genome of the host cell by homologous recombination. Examples of gene targeting by homologous recombination have been described for various cell types including mammalian cells (Mansour et al., 1988, Nature, 336, 348–352) and plant cells (Miao and Lam, 1995, Plant Journal, 7: 359–365). Introduction into the host cell genome of the protein of interest may be accomplished by homologous recombination of the protein of interest in such a fashion that upon recombination an expression cassette is generated which will generally include, in the 5'-3' direction of transcription, a first nucleic acid sequence comprising a transcriptional and translational regulatory region capable of expression in the host cell, a second nucleic acid sequence encoding a fusion protein comprising a sufficient portion of an oil body protein to provide targeting to an oil body and a heterologous protein, and a transcriptional and translational termination region functional in plants.

For embodiments of the invention wherein the production and recovery of the heterologous protein is contemplated from non-plant cells the expression cassette so described above is modified to comprise a first recombinant nucleic acid sequence comprising a transcriptional and translational regulatory sequence capable of expression in the intended host production cell or organism. Promoter regions highly active in cells of microorganisms, fungi, insects and animals are well described in the literature of any contemplated host species and may be commercially available or can be obtained by standard methods known to a person skilled in the art. It is apparent that one means to introduce the recombinant molecule to the host cell is through specific infectious entities such as viruses capable of infection of the host modified to contain the recombinant nucleic acid to be expressed.

In a further embodiment of the invention it is contemplated that proteins other than plant oleosins and proteins with homology to plant oleosins that may specifically associate with triglycerides, oils, lipids, fat bodies or any hydrophobic cellular inclusions in the host organism or with reconstituted plant oil bodies may be fused to a recombinant protein and used in the manner contemplated. A system functionally equivalent to plant oleosins and oil bodies has been described in bacteria (Pieper-Fürst et al., 1994, J. Bacteriol. 176:4328–4337). Other proteins from additional sources such as, but not limited to; fungi, insects or animals, with equivalent regulatory and targeting properties may be known or discovered by a person skilled in the art.

Of particular interest for transcriptional and translational regulation in plants of the first recombinant nucleic acid molecule is a regulatory sequence (promoter) from an oil body protein gene, preferably an oil body protein gene expressed in dicotyledonous oil seeds. The expression of these genes in dicotyledonous oilseeds was found to occur much earlier than had hitherto been believed as reported in the literature. Thus, the promoters and upstream elements of these genes are valuable for a variety of uses including the modification of metabolism during phases of embryogenesis which precede the accumulation of storage proteins. Alternatively said promoter may also comprise a promoter capable of expression constitutively throughout the plant or a promoter which has enhanced expression within tissues or organs associated with oil synthesis. Of more particular interest is a promoter that expresses an oil body protein to a high level. Many plant species are tetraploid or hexaploid and may contain numerous copies of functional oil body protein genes. As it is preferable to obtain a gene that is controlled by a promoter that expresses at high levels when compared to other oil body protein genes within the same species it may be advantageous to choose a diploid species as a source of oil body protein genes. An example is the diploid cruciferous plant *Arabidopsis thaliana*, wherein only two or three oil body protein genes are detected by southern blot analysis whereas the seeds contain oil body proteins as a high percentage of total protein.

The degree of evolutionary relationship between the plant species chosen for isolation of a promoter and the plant species selected to carry out the invention may not be critical. The universality of most plant genes and promoter function within dicotyledonous species has been amply demonstrated in the literature. Additionally to a certain extent the conservation of function between monocot and dicot genes has also been shown. This is apparent to a person skilled in the art that the function of any given promoter in any chosen species may be tested prior to practising the invention by simple means such as transient expression of marker gene promoter fusions in isolated cells or intact tissues. The promoter region typically comprises minimally from 100 bp 5' to the translational start of the structural gene coding sequence, up to 2.5 kb 5' from the same translational start.

Examples of nucleic acid encoding sequences capable of providing targeting to an oil body protein are oleosins genes obtainable from *Arabidopsis thaliana* or *Brassica napus* which provide for expression of the protein of interest in seed (See Taylor et al., 1990, Planta 181:18–26). The necessary regions and amino-acid sequences needed to provide targeting to the oil body reside in the highly hydrophobic central region of oil body proteins. The amino acid sequence necessary to provide targeting to the oil body for *Arabidopsis thaliana* oleosins contain amino acids 46–117 shown in SEQ.ID.NO.2. Similarily, the amino acid sequence necessary to provide targeting to the oil body for *Brassica napus* oleosins contains amino acids 60–132 shown in SEQ.ID.NO.5. In a preferred embodiment, the amino acid sequence necessary for targeting additionally contains the N-terminus of the oleosin which includes amino acids 1–45 (SEQ.ID.NO.2) and 1–60 (SEQ.ID.NO.5) for Arabidopis and Brassica, respectively.

To identify other oil body protein genes having the desired characteristics, where an oil body protein has been or is isolated, the protein may be partially sequenced, so that a probe may be designed for identifying mRNA. Such a probe is particularly valuable if it is designed to target the coding region of the central hydrophobic domain which is highly conserved among diverse species. In consequence, a DNA or RNA probe for this region may be particularly useful for identifying coding sequences of oil body proteins from other plant species. To further enhance the concentration of the mRNA, cDNA may be prepared and the cDNA subtracted with mRNA or cDNA from non-oil body producing cells. The residual cDNA may then be used for probing the genome for complementary sequences, using an appropriate library prepared from plant cells. Sequences which hybridize to the cDNA under stringent conditions may then be isolated.

In some instances, as described above, the use of an oil body protein gene probe (conserved region), may be employed directly for screening a genomic library and identifying sequences which hybridize to the probe. The isolation may also be performed by a standard immunological screening technique of a seed-specific cDNA expression library. Antibodies may be obtained readily for oil-body proteins using the purification procedure and antibody preparation protocol described by Taylor et al. (1990, Planta, 181:18–26). cDNA expression library screening using antibodies is performed essentially using the techniques of Huynh et al. (1985, in DNA Cloning, Vol. 1, a Practical Approach, ed. D. M. Glover, IRL Press, pp. 49–78). Confirmation of sequence is facilitated by the highly conserved central hydrophobic region (see FIG. 1). DNA sequencing by the method of Sanger et al. (1977, Proc. Natl. Acad. Sci. USA, 74:5463–5467) or Maxam and Gilbert (1980, Meth. Enzymol., 65:497–560) may be performed on all putative clones and searches for homology performed. Homology of sequences encoding the central hydrophobic domain is typically 70%, both at the amino-acid and nucleotide level between diverse species. If an antibody is available, confirmation of sequence identity may also be performed by hybrid-select and translation experiments from seed mRNA preparations as described by Sambrook et al. (1990, Molecular Cloning, 2nd Ed., Cold Spring Harbour Press, pp. 8–49 to 8–51).

cDNA clones made from seed can be screened using cDNA probes made from the conserved coding regions of any available oil body protein gene (e.g., Bowman-Vance and Huang, 1987, J. Biol. Chem., 262:11275–11279). Clones are selected which have more intense hybridization with seed DNAs as compared to seedling cDNAs. The screening is repeated to identify a particular cDNA associated with oil bodies of developing seeds using direct antibody screening or hybrid-select and translation. The mRNA complementary to the specific cDNA is absent in other tissues which are tested. The cDNA is then used for screening a genomic library and a fragment selected which hybridizes to the subject cDNA. Of particular interest for transcriptional and translational regulation in plants of said second recombinant nucleic acid molecule is a regulatory sequence (promoter) from a gene expressed during the germination of seeds and the early stages of growth of a seedling, specifically a gene showing high levels of expression during the stage of mobilization of stored seed reserves, more specifically the promoter sequence from the glyoxisomal enzymes iso-citrate lyase or malate synthase. Information concerning genomic clones of iso-citrate lyase and malate synthase from *Brassica napus* and Arabidopsis that have been isolated and described has been published (Comai et al., 1989, Plant Cell 1: 293–300) and can be used by a person skilled in the art, by the methods described above, to isolate a functional promoter fragment. Other enzymes involved in the metabolism of lipids or other seed reserves during germination may also serve as a source of equivalent regulatory regions.

In order to identify oil body proteins, other than oleosins or caleosins, oil body preparations such as described in the art for the plants canola (Van Rooijen and Moloney, 1995, Bio/Technology 13: 72–77) and peanut (Jacks et al., J.A.O.C.S., 1990, 67: 353–361) and such as described for oil body-like granules in the bacterial species *Rhodococcus ruber* (Pieper-Fürst et al., 1994, J. Bacteriol. 176: 4328–4337) may be performed. From such preparations, individual proteins may be readily identified upon electrophoresis on a SDS polyacrylamide gel. Proteins may be extracted from the polyacrylamide gel following the protocol of Weber and Osborn (J. Biol. Chem., 1969, 244: 4406–4412) and polyclonal antibodies against oil body proteins may be obtained using the protocol described by Taylor (1990, Planta, 181: 18–26). In order to isolate the corresponding cDNA clone, a cDNA expression library may then be screened with the antibody using techniques familiar to a skilled artisan (see for example: Huynh et al., 1985, in DNA cloning, Vol. 1, a Practical Approach, ed. D. M. Glover, IRL Press, pp 49–78).

For production of recombinant protein oleosin fusions in heterologous systems such as animal, insect or microbial species, promoters would be chosen for maximal expression in said cells, tissues or organs to be used for recombinant protein production. The invention is contemplated for use in a variety of organisms which can be genetically altered to express foreign proteins including animals, especially those producing milk such as cattle and goats, invertebrates such as insects, specifically insects that can be reared on a large scale, more specifically those insects which can be infected by recombinant baculoviruses that have been engineered to express oleosin fusion proteins, fungal cells such as yeasts and bacterial cells. Promoter regions highly active in viruses, microorganisms, fungi, insects and animals are well described in the literature and may be commercially available or can be obtained by standard methods known to a person skilled in the art. It is preferred that all of the transcriptional and translational functional elements of the initiation control region are derived from or obtained from the same gene.

For those applications where expression of the recombinant protein is derived from extrachromosomal elements, one may chose a replicon capable of maintaining a high copy number to maximize expression. Alternatively or in addition to high copy number replicons, one may further modify the recombinant nucleic acid sequence to contain specific transcriptional or translation enhancement sequences to assure maximal expression of the foreign protein in host cells.

The level of transcription should be sufficient to provide an amount of RNA capable of resulting in a modified seed, cell, tissue, organ or organism. The term "modified" is meant a detectably different phenotype of a seed, cell, tissue, organ or organism in comparison to the equivalent non-transformed material, for example one not having the expression cassette in question in its genome. It is noted that the RNA may also be an "antisense RNA" capable of altering a phenotype by inhibition of the expression of a particular gene.

Ligation of the nucleic acid sequence encoding the targeting sequence to the gene encoding the polypeptide of interest may take place in various ways including terminal fusions, internal fusions, and polymeric fusions. In all cases, the fusions are made to avoid disruption of the correct reading frame of the oil-body protein and to avoid inclusion of any translational stop signals in or near the junctions. The different types of terminal an internal fusions are shown in FIG. 1 along with a representation of configurations in vivo.

In many of the cases described, the ligation of the gene encoding the peptide preferably would include a linker encoding a protease target motif. This would permit the release of the peptide once extracted as a fusion protein. Potential cleavage sites which could be employed are recognition motifs for thrombin (Leu-Val-Pro-Arg-Gly, SEQ. ID. NO.9) (Fujikawa et al., 1972, Biochemistry 11:4892–4899), of factor Xa (Phe-Glu-Gly-Arg-aa, SEQ. ID NO.10) (Nagai et al., 1985, Proc. Natl Acad. Sci. USA, 82:7252–7255) collagenase (Pro-Leu-Gly-Pro, SEQ. ID. NO.11) (Scholtissek and Grosse, 1988, Gene 62:55–64) or Tobacco Etch Virus (TEV) protease (Glu-Asn-Leu-Tyr-Phe-Gln-Gly SEQ. ID NO.12) (Dougherty et al., 1989, Virology, 172: 302). Additionally, for uses where the fusion protein contains a peptide hormone that is released upon ingestion, the protease recognition motifs may be chosen to reflect the specificity of gut proteases to simplify the release of the peptide.

For those uses where chemical cleavage of the polypeptide from the oil body protein fusion is to be employed, one may alter the amino acid sequence of the oil body protein to include or eliminate potential chemical cleavage sites. For example, one may eliminate the internal methionine residues in the Arabidopsis oleosin at positions 11 and 117 by site directed mutagenesis to construct a gene that encodes a oleosin that lacks internal methionine residues. By making a N-terminal fusion with the modified oleosin via the N-terminal methionine residue already present in the Arabidopsis oleosin, one may cleave the polypeptide of interest by the use of cyanogen bromide providing there are no internal methionines in said polypeptide. Similar strategies for other chemical cleavage agents may be employed. It should be noted that a variety of strategies for cleavage may be employed including a combination of chemical modification and enzymatic cleavage.

By appropriate manipulations, such as restriction, chewing back or filling in overhangs to provide blunt ends, ligation of linkers, or the like, complementary ends of the fragments can be provided for joining and ligation. In carrying out the various steps, cloning is employed, so as to amplify the amount of nucleic acid and to allow for analyzing the nucleic acid to ensure that the operations have occurred in proper manner. A wide variety of cloning vectors are available, where the cloning vector includes a replication system functional in *E. coli* and a marker which allows for selection of the transformed cells. Illustrative vectors include pBR332, pUC series, M13mp series, pACYC184, etc for manipulation of the primary nucleic acid constructs. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the nucleic acid sequence to be used in the final construct may be restricted and joined to the next sequence, where each of the partial constructs may be cloned in the same or different plasmids.

The mode by which the oil body protein and the protein to be expressed are fused can be either a N-terminal, C-terminal or internal fusion. The choice is dependant upon the application. For example, C-terminal fusions can be made as follows: A genomic clone of an oil body protein gene preferably containing at least 100 bp 5' to the translational start is cloned into a plasmid vehicle capable of replication in a suitable bacterial host (e.g., pUC or pBR322 in *E. coli*). A restriction site is located in the region encoding the hydrophilic C-terminal portion of gene. In a plant oil body protein of approximately 18 KDa, such as the Arabidopsis oleosin, this region stretches typically from codons 125 to the end of the clone. The ideal restriction site is unique, but this is not absolutely essential. If no convenient restriction site is located in this region, one may be introduced by sitedirected mutagenesis. The only major restriction on the introduction of this site is that it must be placed 5' to the translational stop signal of the OBP clone.

With this altered clone in place, a synthetic oligonucleotide adapter may be produced which contains coding sequence for a protease recognition site such as Pro-Leu-Gly-Pro (SEQ. ID. NO. 11) or a multimer thereof. This is the recognition site for the protease collagenase. The adaptor would be synthesized in such a way as to provide a 4-base overhang at the 5' end compatible with the restriction site at the 3' end of the oil body protein clone, a 4-base overhang at the 3' end of the adaptor to facilitate ligation to the foreign peptide coding sequence and additional bases, if needed, to ensure no frame shifts in the transition between the oil body protein coding sequence, the protease recognition site and the foreign peptide coding sequence. The final ligation product will contain an almost complete oil body protein gene, coding sequence for collagenase recognition motif and the desired polypeptide coding region all in a single reading frame.

A similar approach is used for N-terminal fusions. The hydrophilic N-terminal end of oil-body proteins permits the fusion of peptides to the N-terminal while still assuring that the foreign peptide would be retained on the outer surface of the oil body. This configuration can be constructed from similar starting materials as used for C-terminal fusions, but requires the identification of a convenient restriction site close to the translational start of the oil body protein gene. A convenient site may be created in many plant oil body protein genes without any alteration in coding sequence by the introduction of a single base change just 5' to the start codon (ATG). In plant oil body proteins thus far studied, the second amino acid is alanine whose codon begins with a "G". A–C transition at that particular "G" yields a Nco I site. As an illustration of such a modification, the context of the sequences is shown below:

3' . . . TC TCA ACA ATG GCA . . . Carrot Oil Body Protein (SEQ. ID. NO.13)

3' . . . CG GCA GCA ATG GCG . . . Maize 18 KDa Oil Body Protein (SEQ. ID. NO.14)

A single base change at the adenine prior to the 'ATG' would yield in both cases CCATGG which is an Nco I site. Thus, modification of this base using the site-directed mutagenesis will introduce a Nco I site which can be used directly for the insertion of a nucleic acid coding sequence assuming no other Nco I sites are present in the sequence. Alternatively other restriction sites may be used or introduced to obtain cassette vectors that provide a convenient means to introduce foreign nucleic acid.

The coding sequence for the foreign peptide may require preparation which will allow its ligation directly into the introduced restriction site. For example, introduction of a coding sequence into the Nco I site introduced into the oil body protein coding sequences described above may require the generation of compatible ends. This may typically require a single or two-base modification by site-directed mutagenesis to generate an Nco I site around the translational start of the foreign peptide. This peptide is then excised from its cloning vehicle using Nco I and a second enzyme which cuts close to the translational stop of the target. Again, using the methods described above, a second convenient site can be introduced by site-directed mutagenesis. It has been suggested by Qu and Huang (1990, supra) that the N-terminal methionine might be removed during processing of the plant oil body proteins protein in vivo and that the alanine immediately downstream of this might be acylated. To account for this possibility, it may be necessary to retain the Met-Ala sequence at the N-terminal end of the protein. This is easily accomplished using a variety of strategies which introduce a convenient restriction site into the coding sequence in or after the Ala codon.

The resultant constructs from these N-terminal fusions would contain an oil body protein promoter sequence, an in-frame fusion in the first few codons of the oil body protein gene of a high value peptide coding sequence with its own ATG as start signal if necessary and the remainder of the oil body protein gene and terminator.

A third type of fusion involves the placing of a high value peptide coding sequence internally to the coding sequence of the oil body protein. This type of fusion requires the same strategy as in N-terminal fusions, but may only be functional with modifications in regions of low conservation, as it is believed that regions of high conservation in these oil body proteins are essential for targeting of the mature protein. A primary difference in this kind of fusion is the necessity for flanking protease recognition sites for the release of the protein. This means that in place of the single protease recognition site thus far described, it is necessary to have the protein of interest flanked by one or more copies of the protease recognition site.

Various strategies are dependant on the particular use and nucleic acid sequence of the inserted coding region and would be apparent to those skilled in the art. The preferred method would be to use synthetic oligonucleotides as linkers to introduce the high value peptide coding sequence flanked by appropriate restriction sites or linkers. Orientation is checked by the use of an asymmetrically placed restriction site in the high-value peptide coding sequence.

The heterologous polypeptide of interest to be produced as an oleosin fusion by any of the specific methods described herein, may be any peptide or protein. For example, proteins that alter the amino acid content of seeds may be used. These include genes encoding proteins high in essential amino acids or amino acids that are limiting in diets, especially arginine, histidine, isoleucine, leucine, lysine, methionine, phenylalanine, threonine, tryptophan and valine. Storage proteins such as the high lysine 10 KDa zein from *Zea mays* or the 2S high methionine Brazil Nut storage protein may be used. Alternatively synthetic or modified storage proteins may be employed such as peptides encoding poly-lysine or poly-phenylalanine or fusions of one or more coding regions high in essential amino acids. Proteins may also encode useful additives for animal feeds. These proteins may be enzymes for modification of phytate content in meal such as phytase, more specifically phytase from novel sources and having novel activities. Proteins may also encode hormones useful for boosting productivity such as growth hormones or bovine somatotropin. Proteins may also encode peptides useful for aquaculture.

Proteins may also be those used for various industrial processes. Examples of such proteins include chitinase, glucose isomerase, collagenase, amylase, xylanase, cellulase, lipase, chymosin, renin or various proteases or protease inhibitors. One may also express proteins of interest to the cosmetic industry such as collagen, keratin or various other proteins for use in formulation of cosmetics. Proteins of use to the food industry may also be synthesized including sweetener proteins such as thaumatin, and other flavour enhancing proteins. Proteins that have adhesive properties may also be used.

Of particular interest are those proteins or peptides that may have a therapeutic or diagnostic value. These proteins include antigens, such as viral coat proteins or microbial cell wall or toxin proteins or various other antigenic peptides, peptides of direct therapeutic value such as interleukin-1-β, the anticoagulant hirudin, blood clotting factors and bactericidal peptides, antibodies, specifically a single-chain antibody comprising a translational fusion of the VH or VL chains of an immunoglobulin. Human growth hormone may also be produced. The invention is not limited by the source or the use of the heterologous polypeptide.

The nucleic acid sequence encoding the heterologous polypeptide of interest may be synthetic, naturally derived, or a combination thereof. Dependent upon the nature or source of the nucleic acid encoding the polypeptide of interest, it may be desirable to synthesize the nucleic acid sequence with codons that represent the preference of the organism in which expression takes place. For expression in plant species, one may employ plant preferred codons. The plant preferred codons may be determined from the codons of highest frequency in the proteins expressed in the largest amount in the particular plant species of interest as a host plant.

The termination region which is employed will be primarily one of convenience, since in many cases termination regions appear to be relatively interchangeable. The termination region may be native to the transcriptional initiation region, may be native to the nucleic acid sequence encoding the polypeptide of interest, or may be derived from another source. Convenient termination regions for plant cell expression are available from the Ti-plasmid of *A. tumefaciens*, such as the octopine synthase and nopaline synthase termination regions. Termination signals for expression in other organisms are well known in the literature.

A variety of techniques are available for the introduction of nucleic acid into host cells. For example, the chimeric nucleic acid constructs may be introduced into host cells obtained from dicotyledonous plants, such as tobacco, and oleaginous species, such as *Brassica napus* using standard Agrobacterium vectors by a transformation protocol such as that described by Moloney et al., 1989, Plant Cell Rep., 8:238–242 or Hinchee et al., 1988, Bio/Technol., 6:915–922; or other techniques known to those skilled in the art. For example, the use of T-DNA for transformation of plant cells has received extensive study and is amply described in EPA Ser. No. 120,516; Hoekema et al., 1985, Chapter V, In: The Binary Plant Vector System Offsetdrukkerij Kanters B. V., Alblasserdam; Knauf, et al., 1983, Genetic Analysis of Host Range Expression by Agrobacterium, p. 245, In: Molecular Genetics of the Bacteria-Plant Interaction, Puhler, A. ed., Springer-Verlag, N.Y.; and An et al., 1985, EMBO J., 4:277–284. Conveniently, explants may be cultivated with *A. tumefaciens* or *A. rhizogenes* to allow for transfer of the transcription construct to the plant cells. Following transformation using Agrobacterium the plant cells are dispersed in an appropriate medium for selection, subsequently callus, shoots and eventually plantlets are recovered. The Agrobacterium host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-Agrobacterium techniques permits the use of the constructs described herein to obtain transformation and expression in a wide variety of monocotyledonous and dicotyledonous plants and other organisms. These techniques are especially useful for species that are intractable in an Agrobacterium transformation system. Other techniques for gene transfer include biolistics (Sanford, 1988, Trends in Biotech., 6:299–302), electroporation (Fromm et al., 1985, Proc. Natl. Acad. Sci. USA, 82:5824–5828; Riggs and Bates, 1986, Proc. Natl. Acad. Sci. USA 83 5602–5606 or PEG-mediated DNA uptake (Potrykus et al., 1985, Mol. Gen. Genet., 199:169–177).

In a specific application, such as to *Brassica napus*, the host cells targeted to receive recombinant nucleic acid constructs typically will be derived from cotyledonary petioles as described by Moloney et al., 1989, Plant Cell Rep., 8:238–242). Other examples using commercial oil seeds include cotyledon transformation in soybean explants (Hinchee etal., 1988, Bio/technology, 6:915–922) and stem transformation of cotton (Umbeck etal., 1981, Bio/technology, 5:263–266).

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic nucleic acid using an appropriate probe, for example an *A. thaliana* oleosin gene, to show that integration of the desired sequences into the host cell genome has occurred.

The expression cassette will normally be joined to a marker for selection in plant cells. Conveniently, the marker may be resistance to a herbicide, e.g. phosphinthricin or glyphosate, or more particularly an antibiotic, such as kanamycin, G418, bleomycin, hygromycin, chloramphenicol, or the like. The particular marker employed will be one which will allow for selection of transformed cells compared with cells lacking the introduced recombinant nucleic acid.

The fusion peptide in the expression cassette constructed as described above, expresses at least preferentially in developing seeds. Accordingly, transformed plants grown in accordance with conventional ways, are allowed to set seed. See, for example, McCormick et al. (1986, Plant Cell Reports, 5:81–84). Northern blotting can be carried out using an appropriate gene probe with RNA isolated from tissue in which transcription is expected to occur such as a seed embryo. The size of the transcripts can then be compared with the predicted size for the fusion protein transcript.

Oil-body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (e.g. treatment with colchicine or other microtubule disrupting agents).

The desired protein can be extracted from seed that is preferably homozygous for the introduced trait by a variety of techniques, including use of an aqueous, buffered extraction medium and a means of grinding, breaking, pulverizing or otherwise disrupting the cells of the seeds. The extracted seeds can then be separated (for example, by centrifugation or sedimentation of the brei) into three fractions: a sediment or insoluble pellet, an aqueous supernatant, and a buoyant layer comprising seed storage lipid and oil bodies. These oil bodies contain both native oil body proteins and chimeric oil body proteins, the latter containing the foreign peptide. The oil bodies are separated from the water-soluble proteins and re-suspended in aqueous buffer.

If a linker comprising a protease recognition motif has been included in the expression cassette, a protease specific for the recognition motif is added to the resuspension buffer. This releases the required peptide into the aqueous phase. A second centrifugation step will now re-float the processed oil bodies with their attached proteins and leave an aqueous solution of the released peptide or protein. The foreign protein may also be released from the oil bodies by incubation of the oil body fraction with a different oil body fraction that contains the specific protease fused to oleosin. In this manner the protease cleavage enzyme is removed with the oil bodies that contained the fusion protein with the protease recognition site leaving a product uncontaminated by protease. The desired peptide may be precipitated, chemically modified or lyophilized according to its properties and desired applications.

In certain applications the protein may be capable of undergoing self-release. For example, the proteolytic enzyme chymosin undergoes self-activation from a precursor to an active protease by exposure of the precursor to low pH conditions. Expression of the chymosin precursor/oil body fusion protein to conditions of low pH will activate the chymosin. If a chymosin recognition site is incLuded between the oil body protein and the chymosin protein sequences, the activated chymosin can then cleave the fusion proteins. This is an example of self release that can be controlled by manipulation of the conditions required for enzyme activity. Additional examples may be dependant on the requirement for specific co-factors that can be added when self-cleavage is desired. These may include ions, specific chemical co-factors such as NADH or FADH, ATP or other energy sources, or peptides capable of activation of specific enzymes. In certain applications it may not be necessary to remove the fusion protein from the oil-body protein. Such an application would include cases where the fusion peptide includes an enzyme which is tolerant to N or C-terminal fusions and retains its activity; such enzymes could be used without further cleavage and purification. The enzyme/oil body protein fusion would be contacted with substrate. It is also possible to re-use said oil bodies to process additional substrate as a form of an immobilized enzyme. This specific method finds utility in the batch processing of various substances. The process is also useful for enzymatic detoxification of contaminated water or bodies of water where introduction of freely diffusible enzyme may be undesirable. Said process allows recovery of the enzyme with removal of the oil bodies. It is also possible, if desired, to purify the enzyme—oil body protein fusion protein using an immunoaffinity column comprising an immobilized high titre antibody against the oil body protein.

Other uses for the subject invention are as follows. Oil body proteins comprise a high percentage of total seed protein, thus it is possible to enrich the seed for certain desirable properties such as high-lysine, high methionine, and the like, simply by making the fusion protein rich in the amino-acid(s) of interest could find utility of particular interest is the modification of grains and cereals which are used either directly or indirectly as food sources for livestock, including cattle, poultry, and humans. It may be possible to include, as the fusion peptide, an enzyme which may assist in subsequent processing of the oil or meal in conventional oilseed crushing and extraction, for example inclusion of a thermostable lipid-modifying enzyme which would remain active at the elevated crushing temperatures used to process seed and thus add value to the extracted triglyceride or protein product. Other uses of the fusion protein include improvement of the agronomic health of the crop. For example, an insecticidal protein or a portion of an immunoglobulin specific for an agronomic pest such as a fungal cell wall or membrane, could be coupled to the oil body protein thus reducing attack of the seed by a particular plant pest.

It is possible that the polypeptide/protein will itself be valuable and could be extracted and, if desired, further purified. Alternatively the polypeptide/protein or even the mRNA itself may be used to confer a new biochemical phenotype upon the developing seed. New phenotypes could include such modifications as altered seed-protein or seed oil composition, enhanced production of pre-existing desirable products or properties and the reduction or even suppression of an undesirable gene product using antisense, ribozyme or co-suppression technologies (Izant and Weintraub, 1984, Cell 36: 1007–1015, Hazelhoff and Gerlach, 1988, Nature 334:585–591, Napoli, et al., 1990, Plant Cell, 2:279–289). While one embodiment of the invention contemplates the use of the regulatory sequence in cruciferous plants, it is possible to use the promoter in a wide variety of plant species given the wide conservation of oleosin genes. For example, the promoter could be used in various other dicotyledonous species as well as monocotyledonous plant. A number of studies have shown the spatial and temporal regulation of dicot genes can be conserved when expressed in a monocotyledonous host. The tomato rbcS gene (Kyozuka et al, 1993, Plant Physiol. 102:991–1000) and the Pin2 gene of potato (Xu et al, 1993 Plant Physiol. 101:683–687) have been shown to function in a monocotyledonous host consistent with their expression pattern observed in the host from which they were derived. Studies have also indicated expression from some dicotyledonous promoters in monocotyledonous hosts can be enhanced by inclusion of an intron derived from a monocotyledonous gene in the coding region of the introduced gene (Xu et al, 1994, Plant Physiol. 106:459–467). Alternatively, given the wide conservation of oleosin genes, it is possible for the skilled artisan to readily isolate oleosin genes from a variety of host plants according to the methodology described within this specification.

It is expected that the desired proteins would be expressed in all embryonic tissue, although different cellular expression can be detected in different tissues of the embryonic axis and cotyledons. This invention has a variety of uses which include improving the intrinsic value of plant seeds by their accumulation of altered polypeptides or novel recombinant peptides or by the incorporation or elimination of a metabolic step. In its simplest embodiment, use of this invention may result in improved protein quality (for example, increased concentrations of essential or rare amino acids), improved lipid quality by a modification of fatty add composition, or improved or elevated carbohydrate composition. The invention may also be used to control a seed phenotype such as seed coat color or even the development of seed. In some instances it may be advantageous to express a gene that arrests seed development at a particular stage, leading to the production of "seedless" fruit or seeds which contain large amounts of precursors of mature seed products. Extraction of these precursors may be simplified in this case.

Other uses include the inclusion of fusion proteins that contain antigens or vaccines against disease. This application may be particularly relevant to improvements in health care of fish or other wildlife that is not readily assessable by conventional means as the crushed seed can be converted directly into a convenient food source. Other uses include the addition of phytase to improve the nutritional properties of seed for monogastric animals through the release of phosphate from stored phytate, the addition of chlorophyllase to reduce undesirable chlorophyll contamination of seed oils, especially canoli oil and addition of enzymes to reduce anti-metabolites, pigments or toxins from seeds. Additionally the fusion protein may comprise, an insecticidal or fungicidal protein such as magainin or secropin or a portion of an immunoglobulin specific for an agronomic pest, such as a fungal cell wall or membrane, coupled to the oil body protein thus improving seed resistance to pre and post harvest spoilage.

Applications for the use of chimeric proteins associated with the oil body fraction include as above enzymes that are tolerant of N or C-terminal fusions and retain activity. Enzymes associated with oil body suspensions can be mixed with simple or complex solutions containing enzyme substrates. After conversion of substrates to products the enzyme oleosin fusion is readily recovered by centrifugation and floatation and can be reused an indefinite number of times.

EXAMPLES

The following examples are offered by way of illustration and not by limitation.

Example 1

Isolation of Plant Oleosin Gene

Oil body proteins can be isolated from a variety of sources. The isolation of an oil body protein gene termed oleosin from the plant species *Arabidopsis thaliana* is described herein. Similar methods may be used by a person skilled in the art to isolate oil body proteins from other sources. In this example, a *Brassica napus* oleosin gene (described by Murphy et al, 1991, Biochim Biophys Acta 1088:86–94) was used to screen a genomic library of *A. thaliana* (cv. Columbia) constructed in the Lamda cloning vector EMBL3A (Obtained from Stratagene Laboratories) using standard techniques. The screening resulted in the isolation of a EMBL 3A clone (referred to as clone 12.1) containing a 15 kb genomic fragment which contains a oleosin gene from *A. thaliana*. The oleosin gene coding region is contained within a 6.6 kb Kpn I restriction fragment of this 15 kb fragment. The 6.6 kb KpnI restriction fragment was further mapped and a 1.8 kb Nco I/Kpn I fragment containing the oleosin gene including approximately 850 nucleotides of 5' sequence, the complete coding sequence and the 3' region was isolated. This 1.8 kb fragment was end filled and subcloned in the Sma I site of RFM13mp19. The 1.8 kb insert was further digested with a number of standard restriction enzymes and subcloned in M13mp19 for sequencing. Standard cloning procedures were carried out according to Sambrook et al. (*Molecular Cloning: A Laboratory Manual* 2nd ed., 1989, Cold Spring Harbour Laboratory Press.) The nucleotide sequence was determined and the 1.8 kb sequence of the *A. thaliana* oleosin gene is presented in FIG. 2 and SEQ ID No.1. This particular DNA sequence codes for a 18 KDa *A. thaliana* oleosin gene. The coding region contains a single intron. This gene was used for the construction of recombinant protein expression vectors. The gene may also be used for screening of genornic libraries of other species.

Example 2

Modification of a Native Oleosin for Expression of Heterologous Proteins

The DNA fragment described in example 1 that contains the oleosin gene and regulatory elements was incorporated into an expression cassette for use with a variety of foreign/alternative genes. The following illustrates the modification made to the native *A. thaliana* oleosin gene, especially the promoter and coding region, in order to use this gene to illustrate the invention. It is contemplated that a variety of techniques can be used to obtain recombinant molecules, accordingly this example is offered by way of illustration and not limitation. The *A. thaliana* oleosin gene described in example 1 was cloned as a 1803 bp fragment flanked by Nco 1 and Kpn 1 sites in a vector called pPAW4. The plasmid pPAW4 is a cloning vehicle derived from the plasmid pPAW1 which is a Bluescript plasmid (Clonetech Laboratories) containing a *Brassica napus* Acetolactate synthase (ALS) gene (Wiersma et al., 1989, Mol Gen Genet. 219:413–420). To construct pPAW4, the plasmid pPAW1 was digested with Kpn I. The digested DNA was subjected to agarose gel electrophoresis and the fragment that contained the Bluescript plasmid vector backbone and a 677 base pair portion of the *B. napus* ALS gene was isolated and religated. This plasmid contains the following unique restriction sites within the insert: Pst I, Nco I, Hind III and Kpn I. This plasmid was called pPAW4. The 1803 bp Nco I-Kpn I Arabidopsis oleosin gene fragment was cloned between the Nco I and Kpn I sites in pPAW4. The resultant plasmid contained in addition to the Bluescript plasmid sequences, a 142 bp Pst I-Nco I fragment derived from the *B. napus* ALS gene and the entire 1803 bp Arabidopsis oleosin gene. The 142 bp Pst I-Nco I fragment is present only as a "stuffer" fragment as a result of the cloning approach and is not used in oleosin expression constructs.

Figure 3:
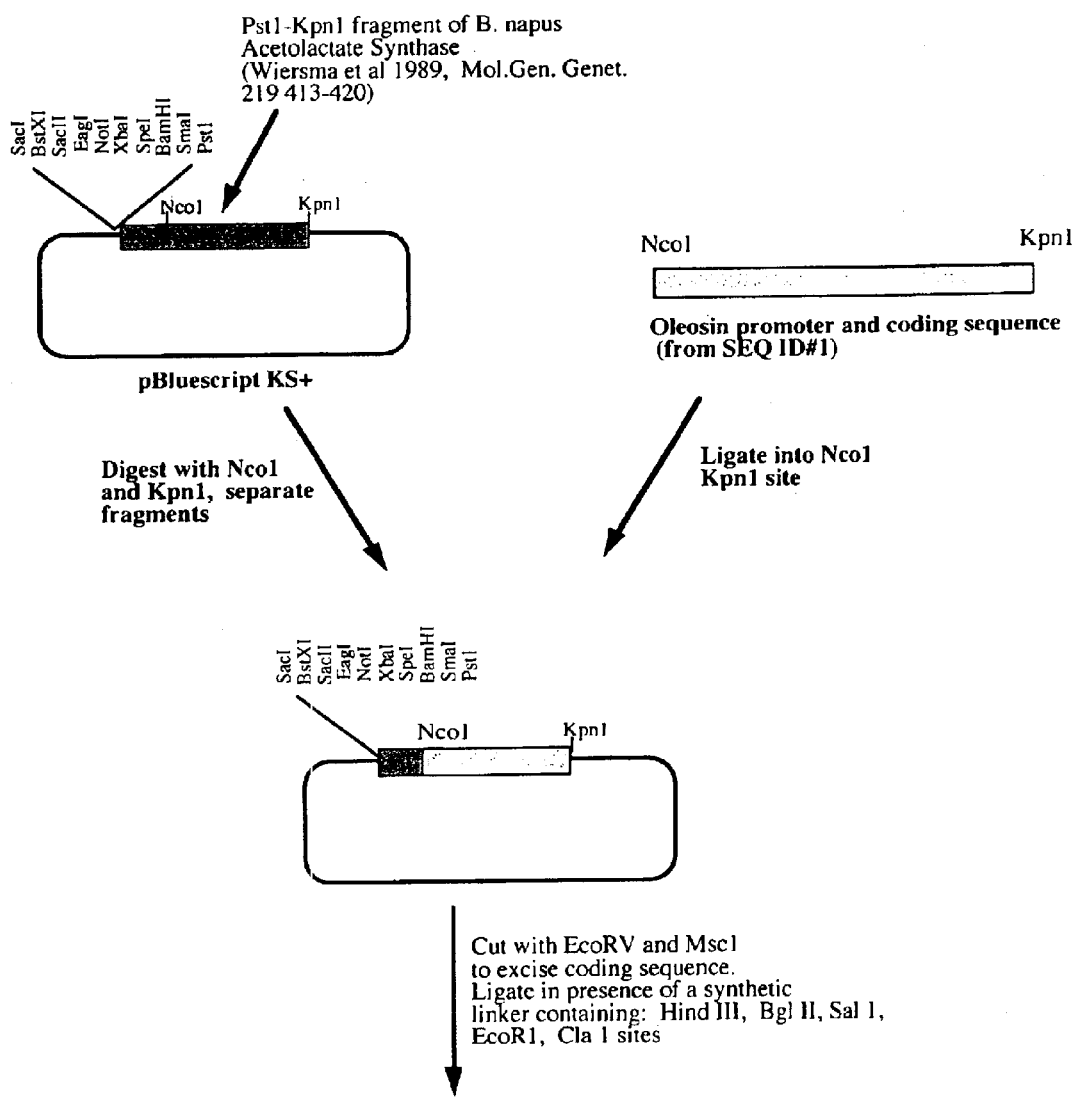
FIG. 3 shows a schematic representation of the construction of pOleoP1.

The resultant plasmid was used to further modify the Arabidopsis oleosin gene. Site-directed mutagenesis was used to introduce nucleotide changes at positions −2, −1 and +4 in the DNA sequence shown in FIG. 2. The changes made were: A to T (nucleotide position −2); A to C (nucleotide position −1) and G to A (nucleotide position +4). These nucleotide changes create a 6 nucleotide Bsp HI restriction endonuclease site at nucleotide positions −2 to +4. The Bsp HI site (T/CATGA) encompasses the ATG initiation codon and provides a recessed end compatible with Nco 1. A second modification was made by digestion with the enzymes Eco RV and Msc 1 which released a 658 bp fragment containing most of the coding sequence of the native oleosin. This digestion left blunt ends at both the Eco RV and Ms c1 sites. The cut vector was recircularized in the presence of an oligonucleotide linker containing the following unique restriction sites: Hind III, Bgl II, Sal I, Eco RI and Cla I. The recircularized plasmid containing all the 5' regulatory sequences of the oleosin gene, a transcriptional start site and an initiation codon embedded in a Bsp HI site. Thirty-one bases downstream of this is a short polylinker containing unique restriction sites. This plasmid was called pOleoP1. The restriction map of this construct is shown in FIG. 3.

Introduction of any DNA sequence into pOleoP1, this particular cassette requires that the foreign DNA sequence may have, or be modified to have, a Bsp HI or Nco I site at the initial ATG position. This will assure conservation of the distance between the "cap" site and the initiator codon. Alternatively restriction site linkers may be added to facilitate insertion into the cassette. The same restriction site can be chosen for the site of insertion of the 3' end of the gene or linkers may be added to introduce appropriate sites. The complete chimeric construct is then excised using the appropriate restriction enzyme(s) and introduced into an appropriate plant transformation vector.

Example 3

Using the Arabidopsis Oleosin Promoter For Controlling Expression in Heterologous Plant Species To demonstrate expression of the oleosin promoter and to determine the amount of 5' regulatory region required for expression in transgenic plants, a small number of DNA constructs were made that contain the 5' transcriptional initiation region of the Arabidopsis oleosin gene joined to the coding region for β-glucuronidase (GUS). These constructs were prepared using PCR. The constructs are designated according to the amount of the oleosin 5' region contained, for example, the 2500 construct has approximately 2500 base pairs of the oleosin 5' region. The constructs were introduced into *Brassica napus* and tobacco and the expression of the β-glucuronidase (GUS) gene was measured as described in detail below. The constructs were made using standard molecular biology techniques, including restriction enzyme digestion, ligation and polymerase chain reaction (PCR). As an illustration of the techniques employed, the construction of the 800 construct is described in detail.

In order to obtain a DNA fragment containing approximately 800 base pairs from the 5' transcriptional initiation region of the Arabidopsis oleosin gene in a configuration suitable for ligation to a GUS coding sequence, PCR was used. To perform the necessary PCR amplification, two oligonucleotide primers were synthesized (Milligen-Biosearch, Cyclone DNA synthesizer). The first primer, the 5' primer, was called GVR10 and had the following sequence (also shown in SEQ ID NO.15):

5'-CA<u>CTGCAG</u>GAACTCTCTGGTAA-3'    (GVR10)

The italicized bases correspond to nucleotide positions −833 to −817 in the sequence reported in FIG. 2. The Pst 1 site is underlined. The additional nucleotides 5' of this sequence in the primer are not identical to the oleosin gene, but were included in order to place a Pst I site at the 5' end of the amplification product.

The second primer, the 3' primer, is designated as ALP 1 and has the following sequence (also shown in SEQ ID NO.16):

5'-CTA<u>CCCGGGATCC</u>TGTTTACTAGAGAGAATG-3'    (ALP 1)

This primer contains the precise complement (shown in italics) to the sequence reported in FIG. 2 from base −13 to −30. In addition, it contains a further 13 bases at the 5' end added to provide two (overlapping) restriction sites, Sma 1 (recognition CCCGGG) and Bam H1 (recognition GGATCC), at the 3' end of the amplification product to facilitate cloning of the PCR fragment. Both the Sma 1 and Bam H1 sites are underlined, the Bam H1 site is delineated by a double underline.

These two primers were used in a PCR amplification reaction to produce DNA fragment containing the sequence between nucleotides −833 and −13 of the oleosin gene that now contains a Pst 1 site at the 5' end and Sma 1 and Bam H1 sites at the 3' end. The template was the oleosin genomic clone 12.1 described in example 1.

The amplification product was called OLEO p800 and was gel purified and digested with Pst 1. The digestion product was gel purified and end filled using DNA polymerase Klenow fragment then cut with Sma 1 to produce a blunt ended fragment. This fragment was cloned into the Sma 1 site of pUC19 to yield the plasmid pUC OLEOp800. This plasmid contained the insert oriented such that the end of the amplified fragment which contained the Pst 1 site is proximal to the unique Hind III site in the pUC19 cloning vector and the end of the amplified fragment that contains the Sma I and Bam HI site is proximal to the unique Eco RI site in the pUC19. This subclone now contains approximately 800 base pairs of 5' regulatory region from the Arabidopsis oleosin gene.

The promoter region contained within the plasmid pUC OLEOp800 was fused to the reporter gene GUS. This was accomplished by substituting the oleosin promoter region for a heat shock promoter fused to a GUS gene in the plasmid HspGUS1559. HspGUS1559 is a plasmid used as a binary vector in Agrobacterium, derived from the vector pCGN 1559 (MacBride and Summerfeldt, 1990, Plant Molecular Biology, 14, 269–276) with an insert containing heat shock promoter (flanked by Bam HI sites), the β-glucuronidase open reading frame and a nopaline synthase terminator (derived from pB1221, Jefferson R A in Cloning Vectors 1988, Eds. Pouwels P., Enger-Valk B E, Brammer W J., Elsevier Science Pub BV, Amsterdam section VII, Ai11). The binary plasmid HspGUS1559 was digested with BamH1 which resulted in the release of the heat shock promoter and permitted the insertion of a BamH1 fragment in its place. pUC OLEOp800 was then cut with Bam H1 to yield a promoter fragment flanked by Bam HI sites. This fragment was cloned into the Bam H1 sites of the plasmid HspGUS1559 to yield the Agrobacterium binary transformation vector pOLEOp800GUSL559. The other constructs were prepared by the same PCR method described above using the appropriate primers for amplifying the 2500 fragment, the −1200 fragment, the −600 fragment or the −200 fragment. These plasmids was used to transform *Brassica napus* and tobacco. GUS expression assays (Jefferson R. A., 1987, Plant Mol. Biol. Rep. 5 387–405) were performed on the developing seeds and on non-reproductive plant parts as controls. The results in *Brassica napus* expressed as specific activity of GUS enzyme are shown in Table I. The results in tobacco are shown in Table II. GUS expression reported is an average obtained from approximately five seeds from each of approximately five different transgenic plants.

These results demonstrate that the oleosin fragment from −833 to −13 used in the 800 construct contains sufficient information to direct specific expression of a reporter gene in transgenic *Brassica napus* embryos as early as heart stage and that the Arabidopsis oleosin promoter is capable of directing transcription in plants other than Arabidopsis.

It should be noted that the specific expression demonstrated here does not depend on interactions with the native terminator of an oleosin gene 3' end. In this example, the 3' oleosin terminator was replaced by a terminator derived from the nopaline synthase gene of Agrobacterium. Thus, the sequence in the 800 construct is sufficient to achieve the desired expression profile independent of ancillary sequences.

Example 4

Use of Oleosin Promoter and Coding Sequences to Direct Fusion Proteins to the Oil Body Fraction of Seeds In this example, we have prepared a transgenic plant which expresses, under the control of the oil body promoter, fusion proteins which associate with oilbodies. The enzymatic properties of the inserted coding sequences are preserved while fused to the oleosin. In this example we use the β-glucuronidase enzyme derived from the microorganism *E. coli*. was fused to the oleosin coding region (referred to as a oleosin/GUS fusion) under the control of the Arabidopsis oleosin promoter. In order to create an in-frame GUS fusion with the Arabidopsis oleosin, two intermediate plasmids were constructed referred to as pOThromb and pGUSNOS.

The plasmid pOThromb comprises the oleosin 5' regulatory region, the oleosin coding sequence wherein the carboxy terminus of the protein has been modified by addition of a thrombin cleavage site. The plasmid pGUSNOS contains the GUS enzyme coding region followed by the nos terminator polyadenylation signal. These two plasmids were joined to make a fusion protein consisting of the oleosin protein fused to the GUS enzyme by way of a linker peptide that is recognized by the endoprotease thrombin.

These plasmids were constructed using PCR and the specific primers shown below. For the construction of pOThromb, a linker oligonucleotide named GVR01 was synthesized having the DNA sequence (shown in SEQ ID NO.17) of:

```
       10         20         30         40
5'AATCCCATGG ATCCTCGTGG AACGAGAGTA GTGTGCTGGC

CACCACGAGT ACGGTCACGG TC 3'    (GVR01)
       50         60
```

This DNA sequence contains from nucleotides 27–62 sequences complementary to the 3' end of the Arabidopsis oleosin coding sequence, from nucleotides 12–26 sequences encoding amino acids that comprise the coding region for a thrombin cleavage site, LVPRGS, and from nucleotides 5–14, the sequence for the restriction sites Bam HI and Nco I. A second primer referred to as GVR10 was also synthesized and consisting of the following DNA sequence (also shown in SEQ ID NO.18):

```
           10         20
    5'-CACTGCAGGAACTCTCTGGTAAGC-3'    (GVR10)
```

This DNA sequence contains from nucleotides 5–24 sequences homologous to the oleosin 5' flanking sequence −834 and −814. These two primers were used to amplify the promoter region (0.8 kb) of the Arabidopsis oleosin gene contained in the clone 12.1 described in example 1. The resultant fragment was endfilled and cloned in the Sma I site of pUC19. This plasmid was called pOThrom which contained the oleosin promoter region, the oleosin coding sequence followed by a cleavage site for the enzyme thrombin and restriction sites for the insertion of the β-glucuronidase (hereinafter GUS).

In order to create an in frame GUS fusion with the Arabidopsis oleosin coding region now contained in pOThrom, a GUS gene with the appropriate restriction site was constructed by the use of PCR. An oligonucleotide referred to as GVR20 was synthesized and containing the following DNA sequence (also shown in SEQ ID NO.19):

```
            10        20
5'-GAGGATCCATGGTACGTCCTGTAGAAACC-3'   (GVR20)
```

This oligonucleotide contains from nucleotides 9–29, sequences complementary to the GUS gene and from nucleotides 3–12 the sequence for the restriction sites Bam HI and Nco I to facilitate cloning. In order to create these restriction sites the fourth nucleotide of the GUS sequence was changed from T to G changing the TTA codon (Leu) into GTA (Val). The second primer used was the universal sequencing primer comprising the DNA sequence (also shown in SEQ ID NO.20):

```
             10
5'-GTAAAACGACGGCCAGT-3'  (Universal Sequencing
                          Primer)
```

The GVR20 and the Universal Sequencing Primer were used to amplify the GUS-nopaline synthase terminator region from the plasmid pBI121 (Clontech Laboratories). This fragment was endfilled and cloned in the Sma I site of pUC19. This plasmid was called pGUSNOS.

The plasmid pOThromb was digested with Pst I and Nco I, pGUSNOS was digested with Nco 1 and Xba I. The inserts of both these plasmids were ligated simultaneously into pCGN1559 cut with Xba I and Pst I to generate plasmid pCGOBPGUS. The plasmid pCGOBPGUS contained in the following order, the Arabidopsis oleosin 5' regulatory region, the oleosin coding region, a short amino acid sequence at the carboxy end of the oleosin coding sequence comprising a thrombin protease recognition site, the coding region for the β-glucuronidase gene followed by the nos terminator polyadenylation signal. The fusion protein coded for by this particular DNA construct is designated as an oleosin/GUS fusion protein.

This plasmid pCGOBPGUS was digested with Pst I and Kpn I cloned into the PstI and Kpn I sites of pCGN1559 resulting in plasmid pCGOBPGUS which was used as a binary vector in Agrobacterium transformation experiments to produce transgenic *B. napus*. Seeds from transgenic *Brassica napus* were obtained and tested for GUS activity. The transformed seeds showed GUS activity specifically associated with the oil body fraction. The results of these experiments are shown in Table III. The data demonstrate specific fractionation of the GUS enzyme to the oil body fraction. This example illustrates the expression and targeting of a bacterial derived enzyme specifically to the oil body fraction of transgenic plants.

One skilled in the art would realize that various modifications can be made to the above method. For example, a constitutive promoter may be used to control the expression of a oleosin/GUS fusion protein. In particular, the 35S promoter may also be used to control the expression of the oleosin/GUS fusion described above by replacing the Arabidopsis oleosin promoter with the 35S promoter from CaMV (available from the vector pBI 221.1, Clonetech Laboratories) in the vector pCGOBPGUS. The resultant vector can contain in the following order, the CaMV 35S promoter, the oleosin coding region, a short amino acid sequence at the carboxy end of the oleosin coding sequence comprising a thrombin protease recognition site, the coding region for the β-glucuronidase gene followed by the nos terminator polyadenylation signal. This plasmid can be inserted into Bin 19 and the resultant plasmid may be introduced into Agrobacterium. The resulting strain can be used to transform *B. napus*. GUS activity can be measured in the oil body fraction.

Example 5

Cleavage of Oleosin-fusion Proteins

In example 4 it was demonstrated that the targeting information contained within the oleosin is sufficient to target the protein oleosin/GUS fusion to the oil body. The oleosin/GUS fusion protein contains an amino acid sequence (LVPRGS SEQ ID NO.21), which separates the oleosin from GUS. This sequence is recognized by the protease thrombin, which cleaves this peptide sequence after the arginine (R) amino acid residue. The transgenic seeds containing these oleosin/GUS fusions, were used to demonstrate the general utility of such a method of cleavage of a foreign peptide from intact oil bodies containing oleosin/foreign peptide-fusions. The oil body fraction that contained the oleosin/GUS fusion was resuspended in thrombin cleavage buffer which consisted of 50 mM Tris (pH 8.0), 150 mM NaCl, 2.5 mM $CaCl_2$, 2% Triton X-100 and 0.5% sarcosyl. Thrombin enzyme was added and the sample was placed for 30 minutes each at 45° C., 50° C. and 55° C. Following this incubation oil bodies were recovered and tested for GUS activity. GUS enzymatic activity was found in the aqueous phase following this cleavage and removal of the oil bodies. This is shown in table IV. Western blot analysis confirmed the cleavage of GUS enzyme from the oleosin/GUS fusion protein. This example illustrates the cleavage and recovery of a active enzyme from a oleosin/enzyme fusion following biosynthesis and recovery of the enzyme in the oil body fraction of transgenic seeds.

Example 6

Use of Fusion Proteins as Reusable Immobilized Enzymes

In this example, oleosin/GUS fusion proteins that were associated with oilbodies were used as immobilized enzymes for bioconversion of substrates. Advantage was taken of the fact that enzymatic properties are preserved while fused to the oleosin and the oleosin is very specifically and strongly associated with the oil bodies even when the oil bodies are extracted from seeds. In this example it is demonstrated that said fusion enzymes can be used repeatedly and recovered easily by their association with the oil bodies. In order to demonstrate the reusable and stable GUS activity of the transgenic seeds, transgenic oil bodies were isolated from mature dry seeds as follows. The *Brassica napus* transgenic seeds containing a oleosin/GUS fusion protein were ground in extraction buffer A which consists of 0.15 M Tricine-KOH pH 7.5, 10 mM KCl, 1 mM $MgCl_2$ and 1 mM EDTA, 4° C. to which sucrose to a final concentration of 0.6M was added just before use. The ground seeds in extraction buffer were filtered through four layers of cheesecloth before centrifugation for 10 minutes at 5000× g at 4° C. The oil bodies present as a surface layer were recovered and resuspended in buffer A containing 0.6M sucrose. This solution was overlaid with an equal volume of Buffer A containing 0.1M sucrose and centrifuged at 18,000× g for 20 minutes. This procedure was repeated twice with the purified oil body fraction (which contained the oilbodies and oleosin/ GUS fusion proteins) and was resuspended in buffer A containing 1 mM p-nitrophenyl β-D-glucuronide, a substrate for the GUS enzyme. After incubation, the conversion of the colorless substrate to the yellow p-nitrophenol was used as an indication of GUS activity in the suspensions of transgenic oil bodies. This illustrated the activity of the enzyme is maintained while fused to the oleosin protein and the enzyme is accessible to substrate while attached to the oil bodies. The oil bodies were recovered as described above. No GUS enzyme remained in the aqueous phase after removal of the oil bodies. The oil bodies were then added to fresh substrate. When the oil bodies were allowed to react with fresh substrate, conversion of substrate was demonstrated. This process was repeated four times with no loss of GUS activity. In parallel quantitative experiments, the amount of methyl umbelliferyl glucuronide (MUG) converted to methyl umbelliferone was determined by fluorimetry, and the oil bodies were recovered by flotation centrifugation and added to a new test tube containing MUG. The remaining buffer was tested for residual GUS activity. This procedure was repeated several times. The GUS enzyme showed 100% activity after using four uses and remained stably associated with the oil body fraction. These results are shown in table V. These experiments illustrate the immobilization and recovery of the active enzyme following substrate conversion. The stability of the GUS activity in partially purified oil bodies was established by measuring the GUS activity of the oil body suspension several weeks in a row. The half-life of the GUS activity when the oil-bodies are stored in extraction buffer at 4° C. is more than 3 weeks.

Expression of Oleosin Fusion Proteins

Example 7

Expression of an Oleosin/IL-1-β as a Fusion Protein

To further illustrate the utility of the invention, the human protein interleukin 1-β (IL-1-β) was chosen for biosynthesis according the method. IL-1-β consists of 9 amino acids (aa); Val-Gln-Gly-Glu-Glu-Ser-Asn-Asp-Lys (Antoni et al., 1986, J. Immunol. 137:3201–3204 SEQ. ID. NO.22). The strategy for biosynthesis was to place this nine amino acid protein at the carboxy terminus of the native oleosin protein. The strategy further employed the inclusion of a protease recognition site to permit the cleavage of the IL-1-β from the oleosin protein while fused to the oil bodies. In order to accomplish this, a recognition site for the endoprotease Factor Xa was incorporated into the construct. The protease Factor Xa can cleave a protein sequence which contains amino acid sequence ile-glu-gly-arg. Cleavage takes place after the arginine residue. Based on these sequences, an oligonucleotide was synthesized which contained 18 nucleotides of the 3' coding region of the A. thaliana oleosin (base position 742–759, coding for the last six amino acids of the native protein), an alanine residue (as a result of replacing the TAA stop codon of the native oleosin with a GCT codon for alanine), the coding sequence for the Factor Xa cleavage (four codons for the amino acids ile-glu-gly-arg) followed by the coding sequence for IL-1-β. The oligonucleotide further comprised a TAA stop coding after the carboxy terminus lysine residue of IL-1-β and adjacent to this stop codon, a Sal 1 restriction site was added. The IL-1-β coding sequence was designed using optimal codon usage for the B. napus and A. thaliana oleosin. It is apparent to those skilled in the art that maximal expression is expected when the codon usage of the recombinant protein matches that of other genes expressed in the same plant or plant tissue. This oligonucleotide was inserted into the Arabidopsis oleosin gene. The modified oleosin gene was cut with Pst 1 and Sal 1 and joined to the nos terminator to obtain the plasmid called pCGOBPILT. This plasmid contains, in the following order, the Arabidopsis oleosin promoter, the oleosin coding sequence, including the intron, and the IL-1-β coding region joined at the carboxy terminus of the oleosin protein through a Factor Xa protease recognition site and the nos terminator polyadenylation signal. This construct was inserted into the binary plasmid Bin 19 (Bevan, M., 1984, Nucl. Acids Res. 12:8711–8721) and the resultant plasmid was introduced into Agrobacterium. The resulting strain was used to transform B. napus and tobacco plants.

The Arabidopsis oleosin/IL-1-β fusion was stably integrated into the genomes of tobacco and B. napus. Northern analysis of embryo RNA isolated from different transformed tobacco plants showed the accumulation of Arabidopsis oleosin/IL-1-β mRNA.

Oil body proteins from transformed tobacco seeds were prepared, and western blotting was performed. An antibody raised against a 22 KDa oleosin of B. napus, was used to detect the Arabidopsis oleosin/IL-1-β fusion in the tobacco seeds. This antibody recognizes all the major oleosins in B. napus and A. thaliana. In addition, this antibody recognizes the tobacco oleosins. In oleosins extracted from transformed tobacco seeds the antibody recognized a 20 KDa-protein, which represents oleosin/IL-1-β fusion oleosin. This fusion protein was not present in the untransformed tobacco seed. These results demonstrate the accumulation of oleosin/IL-1-β fusion in tobacco. Similar expression and accumulation is seen in *Brassica napus* transformed with the oleosin/IL-1-β fusion gene. These results further exemplify the utility of the method for the expression of heterologous proteins in plants.

Example 8

Expression of Oleosin/Hirudin Gene Fusion in *B. napus*

As a further example of the invention, the protein hirudin, derived from the leech (a segmented worm) was synthesized and fused to oleosin. Hirudin is an anti-coagulant which is produced in the salivary glands of the leech *Hirudo medicinalis* (Dodt et al., 1984, FEBS Lett., 65:180–183). The protein is synthesized as a precursor protein (Harvey et al., 1986, Proc. Natl. Acad. Sci. USA 83: 1084–1088) and processed into a 65 amino acid mature protein. The hirudin gene was resynthesized to reflect the codon usage of Brassica and Arabidopsis oleosin genes and a gene fusion was made with the C-terminal end of the Arabidopsis oleosin gene. The gene sequences for oleosin and huridin were separated by codons for an amino acid sequence encoding a Factor Xa endoprotease cleavage site. The resulting plasmid was called pCGOBHIRT. This plasmid contains, in the following order, the promoter region of the Arabidopsis oleosin gene, the coding sequence of the oleosin protein including the intron, a factor Xa cleavage site and the resynthesized huridin gene followed by the nos terminator polyadenylation signal. This construct was inserted into the binary plasmid Bin 19 and the resultant plasmid was introduced into Agrobacterium. The resulting strain was used to transform *B. napus* and tobacco.

The Arabidopsis oleosin/hirudin fusion (OBPHIR) was stably integrated into the genomes of *N. tabacum* and *B.*

*napus* respectively. Northern analysis of embryo RNA isolated from different OBPHIR transformed plants showed the accumulation OBPHIR mRNA in *B. napus* seeds. Monoclonal antibodies raised against hirudin confirmed the stable accumulation of the oleosin/hirudin fusion in the seeds of transformed plants. Transgenic seeds containing an oleosin/hirudin were assayed after a year of storage at room temperature. No degradation of the oleosin/hirudin protein could be observed demonstrating the stability of the huridin in intact seeds.

The huridin can be cleaved from the oleosin by the use of the Factor Xa cleavage site built into the fusion protein. Upon treatment of the oilbody fraction of transgenic *Brassica napus* seeds, active huridin was released. These results are shown in Table VI. This example illustrates the utility of the invention for the production of heterologous proteins with therapeutic value from non-plant sources.

Example 9

Fusion of Foreign Proteins to the N-terminus of Oleosin

In this example, a foreign protein was joined to the oleosin coding region via fusion to the N-terminus of the oleosin. As an illustration of the method, the GUS enzyme was fused in-frame to the Arabidopsis oleosin coding region described in example 1. In order to accomplish this, four DNA components were ligated to yield a GUS-oleosin fusion under the control of the oleosin promoter. These were: The oleosin 5' regulatory region, the GUS coding region, the oleosin coding region, and the nos ter transcription termination region. These four DNA components were constructed as follows:

The first of these components comprised the oleosin promoter isolated by PCR using primers that introduced convenient restriction sites. The 5' primer was called OleoPromK and comprised the sequence (also shown as SEQ. ID. NO.23):

```
             Ncol
5'-CGC GGT ACC ATGG CTA TAC CCA ACC TCG-3'
        Kpn1
```

This primer creates a convenient Kpn 1 site in the 5' region of the promoter. The 3' primer comprised the sequence (also shown as SEQ. ID. NO.24):

```
5'-CGC ATCGATGTTCTTGTTTACTAGAGAG-3'
        Cla1
```

This primer creates a convenient Cla 1 site at the end of the untranslated leader sequence of the oleosin transcribed sequence just prior to the ATG initiation codon in the native oleosin sequence. These two primers were used to amplify a modified promoter region from the native Arabidopsis oleosin gene. Following the reaction, the amplification product was digested with Kpn 1 and Cla 1 to yield a 870 bp fragment containing the oleosin promoter and the 5' untranslated leader sequence. This promoter fragment is referred to as Kpn-OleoP-Cla and was ligated in the Kpn 2-Cla 1 sites of a standard subcloning vector referred to as pBS.

The second DNA component constructed was the GUS coding region modified to introduce the appropriate restriction sites and a Factor Xa cleavage site. In order to accomplish this, the GUS coding region in the vector PBI221 was used as a template in a PCR reaction using the following primers. The 5' primer was called 5'-GUS-Cla which comprised the following sequence (also shown as SEQ. ID. NO.25):

```
              Nde1
5'-GCC ATCGATCAT ATG TTA CGT CCT GTA GAA ACC
                                          CCA-3'
       Cla 1
```

The 3' primer was referred to as 3'-GUS-FX-Bam and comprised the following nucleotide sequence (also shown as SEQ. ID. NO.26):

```
5' CGC GGATCC TCT TCC TTC GAT TTG TTT GCC TCC CTG
                                              C-3'
       Bam H1     Factor Xa
``` encoding DNA sequence shown in boldface

This second oligonucleotide also encodes four amino acids specifying the amino acid sequence I-E-G-R, the recognition site for the endoprotease activity of factor Xa. The amplification product of approximately 1.8 kb comprises a GUS coding region flanked by a Cla 1 site at the 5' end and in place of the GUS termination codon, a short nucleotide sequence encoding the four amino acids that comprise the Factor Xa endoprotease activity cleavage site. Following these amino acid codons is a restriction site for BamH1.

The isolation of the oleosin coding region was also performed using PCR. To isolate this third DNA component, the Arabidopsis oleosin genomic clone was used as a template in a reaction that contained the following two primers. The first of these primers is referred to as 5'-Bam-Oleo and has the following sequence (also shown as SEQ. ID. NO.27):

```
5' CGC GGATCC ATG GCG GAT ACA GCT AGA 3'
       Bam H1
```

The second primer is referred to as 3'-Oleo-Xba and has the following sequence (also shown as SEQ. ID. NO.28):

```
5' TGC TCT AGA CGA TGA CAT CAG TGG GGT AAC TTA AGT 3'
       Xba 1
```

PCR amplification of the genomic clone yielded an oleosin coding region flanked by a Bam H1 site at the 5' end and a Xba 1 site at the 3' end. This coding sequence was subcloned into the Bam Hi and Xba 1 site of the subcloning vector pBS.

The fourth DNA component comprised the nopaline synthetase transcriptional termination region (nos ter) isolated from the vector pBI 221 as a blunt-ended Sst 1-EcoRI fragment cloned into the blunt-ended Hind III site of pUC 19. This subclone has a Xba 1 site at the 5' end and a Hind III site at the 3' end.

As a first step to assemble these four DNA components, the oleosin coding region and nos ter were first jointed by ligation of the Bam HI-Xba I fragment of the oleosin coding region with the Xba 1-Hind III fragment of the nos ter into Bam HI-Hind III digested pUC 19. This construct yielded a subclone that comprised the oleosin coding region joined to the nos ter. As a second step in the assembly of the DNA components, the oleosin promoter region was then joined to the modified GUS coding region by ligation of the Kpn 1-Cla 1 oleosin promoter fragment to the Cla 1-Bam H1 fragment of the GUS coding region modified to contain the Factor Xa recognition site and subcloning these ligated fragments into pUC 19 cut with Kpn 1 and Bam H1.

To assemble all four DNA components, the Kpn 1-Bam H1 oleosin promoter fused to the GUS coding region was ligated with the Bam HI-Hind III oleosin coding region-nos ter fragment in a tripartite ligation with Kpn1-Hind III digested Agrobacterium binary transformation vector PCGN1559. The resultant transformation vector was called pCGYGON1 and was mobilized into *Agrobacterium tumefaciens* EHA 101 and used to transform *B. napus*. Transformed plants were obtained, transferred to the greenhouses and allowed to set seed. Seeds were analyzed as described by Holbrook et al (1991, Plant Physiology 97:1051–1058) and oil bodies were obtained. Western blotting was used to demonstrate the insertion of the GUS oleosin fusion protein into the oil body membranes. In these experiments, more that 80% of the GUS oleosin fusion protein was associated with the oil body fraction. No degradation of the fusion protein was observed. This example illustrates the utility of the method for the expression and recovery of foreign proteins fused to the N-terminus of oleosin.

Example 10

Expression of an Oleosin/Chymosin Fusion Protein

As a further example of the invention, the bovine aspartic protease, chymosin—which is also frequently referred to in the art as rennin—was expressed as an oleosin fusion. Also exemplified here is the cleavage of an oleosin fusion protein by chemical means.

A complementary DNA clone containing a gene of interest may be obtained by any standard technique. For the purpose of this experiment, reverse transcription PCR was used to obtain a full length pre-prochymosin cDNA clone. RNA isolated from calf abomasum was used as the source material for the PCR and primers were designed in accordance with the sequence described by Harris et al. (1982, Nucl. Acids Res., 10: 2177–2187). Subsequently, prochymosin was furnished with an NcoI recognition sequence (CCATGG) in such a way that the initiating methionine codon was in frame with the prochymosin cDNA. The Met-prochymosin sequence was ligated in frame to the 3' coding sequence of an *A. thaliana* oleosin genomic sequence oleosin in which the TAA stopcodon had been replaced by a short spacer sequence (encoding LVPRGS SEQ ID NO.29) and an NcoI site. The complete sequence of a HindIII fragment containing the oleosin-spacer-Met-prochymosin sequence is shown in FIG. 6 and SEQ. ID. NO 6. This HindIII fragment was joined to a nopaline synthase terminator and cloned into the binary vector pCGN1559 (McBride and Summerfelt, 1990, Plant Mol. Biol. 14: 269–276). The resulting plasmid was called pSBSOTPTNT and introduced in *A. tumefaciens*. The resulting bacterial strain was used to transform *B. napus* plants.

Oil bodies from transformed *B. napus* plants were prepared and resuspended in 100 mM Tris-Cl, pH 8.0. In order to demonstrate chemical cleavage of chymosin from the oleosin-spacer-Met-prochymosin fusion, the pH of the oil body suspension was lowered into two steps to pH 5.5 and pH 3.0, respectively using HCl. Oil bodies were subjected to these acidic conditions for several hours prior to Western blotting. Western blotting was performed using polyclonal antibodies raised against bovine chymosin and using commercially available chymosin (Sigma) as a positive control. The oleosin-spacer-Met-prochymosin fusion protein (approximately 62 kDa) could only be detected in oil body protein extracts obtained from transgenic *B. napus* seeds incubated at pH 8.0 and pH 5.0. No mature chymosin (35 kDa) was detected in protein extracts incubated under these conditions. The mature chymosin polypeptide was detected as the predominant molecular species in oil body protein extracts incubated at pH 3.0. In addition, oil body protein extracts incubated at pH 3.0 were the only extracts exhibiting chymosin activity as measured by milk-clotting assay. In protein extracts isolated from untransformed control plants no specific cross-reactivity with anti-chymosin antibodies was detected.

Example 11

Expression of an Oleosin/Cystatin Fusion Protein

As a further example of the present invention, the expression of a protein that is toxic to insects is illustrated. The cysteine protease inhibitor, cystatin (OC-I), from *Oryza sativa* was expressed in a germination-specific manner in *Brassica napus* cv. Westar. The strategy for biosynthesis was to place the coding sequence for the complete 11.5 kDa OC-I protein downstream of the isocitrate lysase (ICL) promoter, isolated from *Brassica napus* (Comai et al., 1989, Plant Cell 1: 293–300). The ICL promoter has been shown to be functional for several days directly after germination of the seeds. Thus, this will allow for the pulse release of cystatin only for several days after germination when seedlings are most susceptible to the feeding of insects such as the flea beetle (*Phyllotreta cruciferae*) or the red turnip beetle (*Entomoscelis americana*).

The 313 bp sequence, encoding OC-I, from the cDNA clone OC 9b (Chen et al., 1992, Prot. Expr. and Purif., 3: 41–49) was amplified by PCR, using 5' and 3' specific primers, designed to introduce BspHI and BamHI sites for cloning purposes. The resulting fragment was cloned into pITG7, a vector containing the nos terminator of transcription. OC-I -nos was amplified from this plasmid by PCR, using the 5' primer specific to the OC-I coding sequence and the Universal primer (Stratagene). The resulting OC-I -nos fragment was cloned into the SmaI site of pBS(KS), excised with BspHI and KpnI and introduced into pUC18-ICL (plasmid containing the ICL promoter) at the NcoI and KpnI sites. The entire ICL-OC-I -nos cassette was removed by digestion with PstI, cloned into the plant binary vector pCGN 1547 (McBride and Summerfelt, 1990, Plant Mol. Biol. 14: 269–276) and designated pCGN-ICLOC. This plasmid was introduced into *Agrobacterium tumefaciens* EHA101 and the resulting strain was used to transform *Brassica napus* cv. Westar, using the cut petiole transformation method (Moloney et al., 1989, Plant Cell Reports 8: 238–242). Transformation resulted in the stable integration of the ICL-OC-I -nos construct into the genome of *Brassica napus*. Northern blot analysis of poly-A$^+$ mRNA isolated from seedlings showed the accumulation of OC-I mRNA transcripts between one (1) to four (4) days after germination.

Protein extracts from the cotyledons of transformed *Brassica napus* seedlings were prepared using standard techniques (Sambrook et al., 1989, Molecular Cloning: a laboratory manual 2nd ed, Cold Spring Harbor Laboratory Press) and Western blot analysis was performed in order to determine if OC-I protein was produced. A polyclonal antibody raised against the truncated 10 kDa recombinant form of OC-I (Chen et al., 1992) was produced and allowed the detection of the complete OC-I protein (11.5 kDa) in extracts prepared from transformed *Brassica napus* seedlings. The OC-I protein was not detected in ungerminated seeds or in untransformed seeds or seedlings. The expression of OC-I was also found to be tissue specific, with the protein being found in cotyledons and hypocotyls but absent from roots and the first true leaves.

In order to prove functionality of the OC-I protein produced in the *Brassica napus* seedlings, a proteinase inhibitor assay (Rymerson et al., manuscript in preparation) was performed, using the proteinase papain. OC-I produced in the seedlings was shown to significantly inhibit the activity of papain. The experiments described here, indicate that OC-I protein, cystatin, is produced in a germination and tissue specific manner and acts as a functional proteinase inhibitor in this system.

Example 12

Expression of an Oleosin/Xylanase Fusion Protein

As a further example of the present invention, the production of an industrial enzyme, xylanase, is illustrated. A variety of industrial applications have been reported for xylananes (Jeffries et al., 1994, TAPPI 77: 173–179; Biely, 1985, Trends Biotechnol. 3: 286–290), including the conversion of the pulp and paper industry waste product xylan to useful monosaccharides.

The xynC gene encoding a highly active xylanase from the rumen fungus *Neocallimastix patriciarum* (Selinger et al., 1995, Abstract, 23rd Biennial Conference on Rumen Function, Chicago, Ill.) was joined in-frame to oleosin via a fusion to the C-terminus of the Arabidopsis oleosin coding region described in example 1. The xynC gene consists of an N-terminal catalytic domain preceded by a signal peptide. The xylanase gene lacking the ATG startcodon and partial signal peptide coding sequence was first amplified by PCR using the following 2 primers (also shown in SEQ ID NO 30 and SEQ ID NO 31):

```
            10        20              30
5'-ATCTCTAGAATTCAACTACTCTTGCTCAAAG-3'
and
            10        20
5'-GGGTTGCTCGAGATTTCTAATCAATTTAT-3'
```

The PCR product was digested with EcoRI and XhoI and cloned into the *E. coli* expression vector pGEX4T-3 (Pharmacia) and designated pGEXxyn. Following expression and purification of the xylanase-glutathion-S-transferase fusion protein according to the protocol provided by the manufacturer, polyclonal antibodies against xylanase were obtained from rabbits immunized with thrombin-cleaved, purified recombinant xylanase.

In order to obtain the 1608 bp fragment containing the oleosin promoter and oleosin coding region, the construct pCGYOBPGUSA (van Rooijen and Moloney, 1995, Plant Physiol. 109: 1353–1361) was digested with PstI and BamHI. The xylanase coding region was obtained by digestion of pGEXxyn with EcoRI and XhoI. The oleosin fragment and xylanase fragment were cloned into pBluescript (pBS), previously digested with EcoRI and XhoI, resulting in pBSOleXyn. In order to isolate the nopaline synthase (NOS) terminator region containing XbaI and XhoI cloning sites, the BamHI-HindIII fragment from pCGYOBPGUSA containing the NOS terminator sequence was subcloned in pBS to yield the intermediate plasmid pBSNos. Digestion of pBSNos with XbaI and XhoI and digestion of pBSOleXyn with PstI and XhoI yielded fragments containing the NOS terminator and the oleosin-xylanase fusion respectively and were ligated into the binary vector pCGN1559 which was digested with PstI and XhoI. The resulting binary vector containing the recombinant oleosin-xylanase fusion was named pCGOleXyn. Following introduction of pCGO-LeXyn into *A. tumefaciens*, *B. napus* cv Westar plants were transformed using the method of Moloney et al. (1989, Plant Cell Rep. 8: 238–242).

Accumulation of oleosin-XynC fusion protein in oil-bodies of transgenic canola plants was assessed by Western analysis. Probing of total seed protein extracts and oil body protein extracts with anti-XynC antiserum revealed the presence of a predominant band of 70 kDa on Western blots in both extracts. The predicted molecular weight of the oleosin-XynC fusion protein (68.2 kDa) and hence is in good agreement with the observed band. The fusion protein was absent in extracts from untransformed plants.

In order to evaluate functional activity of the oleosin-xylanase fusion proteins, xylanase enzyme assays using remazol brilliant blue-xylan (RBB-xylan) as described by Biely et al. (1988, Methods Enzymol. 160: 536–542) were carried out using oilbody immobilized xylanase. Xylanase activity was found to be associated almost exclusively with the oil body fraction and kinetic parameters were comparable to those of microbially expressed xylanase.

Example 13

Expression of an Oleosin/Carp Growth Honnone Fusion Protein

As a further example of this invention, the production of carp growth hormone (cGH) as an oleosin fusion protein is described. A DNA fragment containing the cGH coding region lacking its 22 amino acid signal sequence was amplified from a plasmid containing on an insert a common carp (*Cyprinus carpio*) growth hormone cDNA (Koren et al., 1989, Gene 67: 309–315) using the PCR in combination with two cGH-specific primers. The amplified cGH fragment was fused in the correct reading frame and 3' to the *A. thaliana* oleosin using pOThromb (van Rooijen, 1993, PhD Thesis, University of Calgary) as a parent plasmid and employing cloning strategies similar to those outlined in the present application in e.g. examples 9 to 11 and well known to a person skilled in the art. In pOThromb a thrombin cleavage site was engineered 3' to the oleosin coding sequence. The oleosin-cGH fusion was introduced into the binary vector pCGN1559 (McBride and Summerfelt, 1990, Plant Mol. Biol. 14: 269–276) and the resulting construct was used to transform *A. tumefaciens*. The Agrobacterium strain was employed to transform *B. napus* cv Westar seedlings.

Seeds from transgenic *B. napus* plants were analysed for cGH expression by Western blotting using monoclonal antibodies against cGH. The expected 40 kDa oleosin-cGH fusion protein was specifically detected in oil body protein extracts containing the oleosin-cGH fusion protein. A 22 kDa polypeptide corresponding with cGH could be released from oil bodies upon treatment with thrombin, while no cGH was detected in oil body protein extracts from untransformed control plants.

Example 14

Expression of an Oleosin/Zein Fusion Protein

In order to demonstrate the utility of the instant invention for the production of improved meal, a gene specifying high levels of methionine residues, was expressed as an oleosin fusion in *B. napus* seeds. For the purpose of this experiment the gene encoding the corn seed storage protein zein (Kirihara et al., 1988, Gene 71: 359–370) was used. The zein gene was fused 3' of the oleosin coding sequence and introduced in the binary vector pCGN1559 (McBride and Summerfelt, 1990, Plant Mol. Biol. 14: 269–276) employing cloning strategies similar to those described in the present application in e.g. examples 9 to 11 and well known to the skilled artisan. The resulting recombinant plasmid was introduced in *A. tumefaciens* and used to transform *B. napus* cotyledonary explants. Amino acid analyses of canola meal of plants transformed with the oleosin-zein fusion construct indicated a significant increase in the levels of methionine in the meal when compared to untransformed plants.

Example 15

Construction of an Oleosin/Collagenase Protein Vector

As a further example of the invention, a vector containing an oleosin-collagenase fusion was constructed.

A 2.2 kbp fragment containing the collagenase gene from *vibrio alginolyticus* was PCR amplified from genomic bacterial DNA using primers in accordance with the published sequence (Takeuchi et al., 1992, Biochem. Journal, 281: 703–708). The fragment 2.2 kbp was then subcloned into pUC19 yielding pZAP1. Subsequently, the collagenase gene was introduced into pNOS8 containing the NOS terminator. The collagenase gene was ligated to the oleosin promoter and coding sequence of pThromb (van Rooijen, 1993, PhD Thesis, University of Calgary) containing a thrombin cleavage site and introduced into the binary vector pCGN1559 (McBride and Summerfelt, 1990, Plant Mol. Biol. 14: 269–276).

The collagenase construct may be introduced in a transgenic plant containing a second oleosin gene fusion to, for example, a gene encoding the enzyme chitinase isolated from tobacco (Melchers et al., 1994, Plant Journal 5: 469–480) and containing a collagenase recognition sequence engineered between the oleosin sequence and the second fusion protein. Introduction of the two fusion genes may be accomplished by sexual crossing of two lines which each contain one of the fusion genes or by transformation of a plant containing the first construct the second construct.

Expression in Plant Hosts

Example 16

Expression of Oleosin/GUS Fusions in Various Plant Species

It is a feature of the present invention that a wide variety of host cells may be employed. In order to illustrate the expression of oleosin fusions in a number of plant species, the expression of the *A. thaliana* oleosin fused to the reporter gene GUS was assessed in the embryos of nine different plant species, including the monocotelydenous plant species *Zea mays* (corn).

Plasmid pCGYOBPGUS containing the intact *A. thaliana* oleosin gene with a carboxyl terminal fused GUS gene (van Rooijen et al., 1995, Plant Physiol. 109: 1353–1361) was used to transform oilseed embryos of the following plant species: *Brassica napus* (canola), *Helianthus anuus* (sunflower), *Carthamus tinctorius* (safflower), *Glycine max* (soybean), *Ricinus communis* (castor bean), *Linum usitatissimum* (flax), *Gossypium hirsutum* (cotton), *Coriandrum sativum* (coriander) and *Zea mays* (corn). Transformation was accomplished by particle bombardment (Klein et al., 1987, Nature, 327: 70–73) and plasmid pGN, containing a promoterless GUS gene was used as a control. Histochemical GUS staining (Klein et al., 1988, Proc. Natl. Acad. Sci. 85: 8502–8505) of the embryos was used to assess GUS expression.

The embryos of the 9 species transformed with plasmid pCGTYOBPGUS containing the oleosin-GUS fusion gene all exhibited substantial GUS expression as judged by histochemical staining. In contrast, no appreciable levels of GUS activity was detected in embryos transformed with the promoterless GUS construct.

Expression in Prokaryotes

Example 17

Isolation of a *B. napus* Oleosin cDNA

The Arabidopsis oleosin gene described in Example 1 contains an intron, and as such is not suitable for use in a prokaryotic expression system. In order to express oleosin fusions in a microorganism such as bacteria, a coding sequence devoid of introns must be used. To accomplish this, a *B. napus* cDNA library was made using standard techniques and was used to isolate oleosin cDNAs. Four clones were obtained and were called pcDNA#7, pcDNA#8, pcDNA#10 and pcDNA#12. These cDNA clones were partly sequenced, and one clone pcDNA#8, was sequenced completely. All the clones showed high levels of identity to oleosins. pcDNA#10 was identical to pcDNA#12, but different from pcDNA#8 and pcDNA#7. The deduced amino acid sequence of the insert of pcDNA#8 is very similar to the Arabidopsis oleosin and is shown in FIG. 4. This coding region of oleosin can be used to isolate other oleosin genes or for expression of oleosin fusions in prokaryotic systems. It also provides a convenient coding region for fusion with various other promoters for heterologous expression of foreign proteins due to the ability of the protein (oleosin) to specifically interact with the oilbody fraction of plant extracts.

Example 18

Expression of a Oleosin/GUS Fusion in the Heterologous Host *E. coli*

Figure 5:
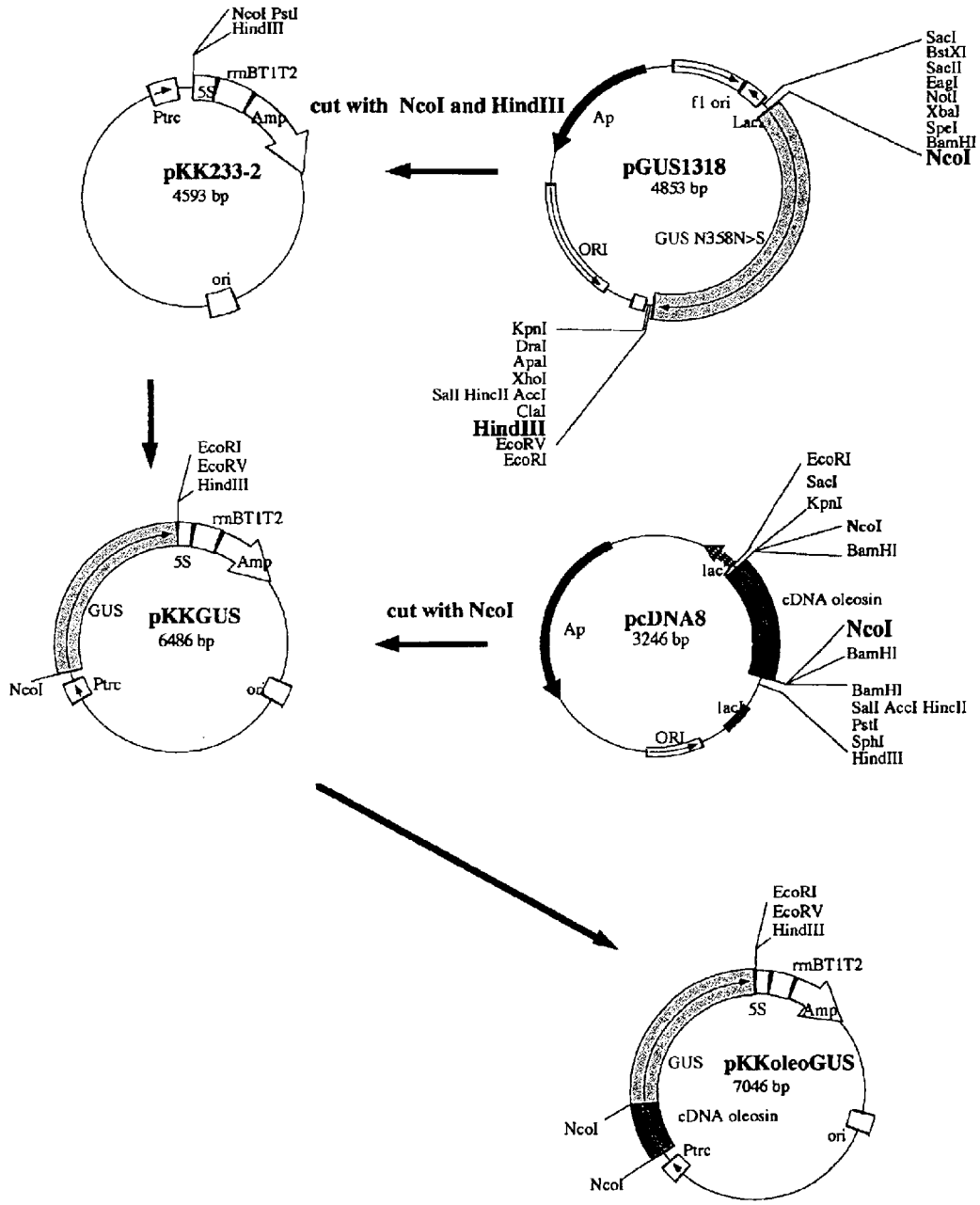
FIG. 5 describes the construction of a oleosin/GUS fusion for expression in *E. coli*.

In order to further illustrate the invention, an oleosin/GUS gene fusion was expressed in *E. coli* strain JM109. The oleosin cDNA pcDNA#8 described in example 17 was digested with Nco I and ligated into the Nco I site of pKKGUS, an expression vector containing the LacZ promoter fused to GUS. The plasmid pKKGUS was constructed by adding the GUS coding region to the vector pKK233 (Pharmacia) to generate the plasmid pKKoleoGUS and the anti-sense construct pKKoeloGUS. This construct is shown in FIG. 5. These plasmids were introduced into *E. coli* strain JM109 and expression was induced by IPTG. The *E. coli* cells were prepared for GUS activity measurements. In bacterial cells containing the vector pKKGUS, strong induction of GUS activity is observed following addition of ITPG. In cells containing pKKoleoGUS similar strong induction of GUS activity was seen following addition of IPTG. In cells containing pKKoeloGUS (GUS in the antisense orientation) no induction over background was observed following the addition of IPTG. These results suggest that the oleosin/GUS fusion is active in bacteria. Although that activity observed for the fusion product is less than the unfused product, the oleosin coding sequence was not optimized for expression in bacteria. It is apparent to those skilled in the art that simple modification of codons or other sequences such as ribosome binding sites could be employed to increase expression. The results are summarized in Table VII.

The fusion protein can be isolated from the bulk of the cellular material by utilizing the ability of the oleosin portion of the fusion proteins to specifically associate with oil bodies.

Expression in Fungi

Example 19

Expression of an Oleosin/GUS Fusion in the Heterologous Host *Saccharomyces cerevisiae*

Figure 7:
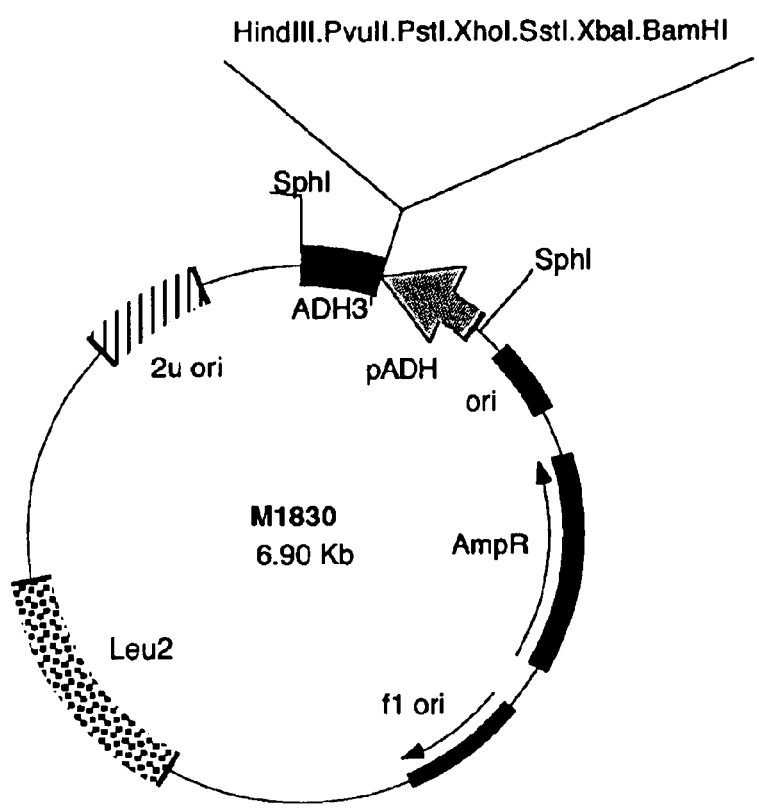
FIG. 7 shows a schematic drawing of plasmid M1830. The plasmid was constructed by replacing the Ura3 gene from pVT102-U (Gene 52: 225–233, 1987) with the Leu2 gene.
Figure 8:
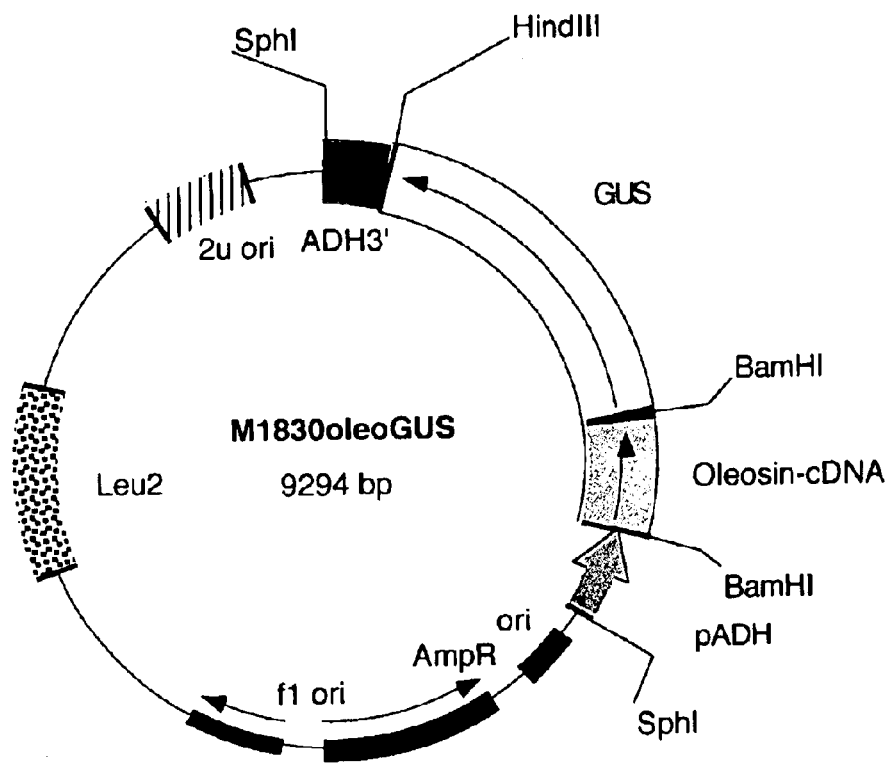
FIG. 8 shows a schematic drawing of plasmid M1830oleoGUS. A BamHI-GUS-hindIII fragment was inserted into the multiple cloning site of M1830, resulting in M1830GUS. A *B. napus* oleosin cDNA was furnished with BamHI sites at the 5' and 3' ends of the gene and inserted in frame and in the right orientation in the BamHI site of M1830GUS yielding plasmid M1830oleoGUS.

As an example of the utility of the disclosed invention for expression in fungal systems, an oleosin-GUS fusion was expressed in *S. cerevisiae*. Plasmids pM1830OleoGUS, containing an oleosin-GUS fusion, and control plasmid pM1830 (FIGS. 7 and 8) were used to to transform *S. cerevisiae* strain 1788 (Mata/Matα) an isogenic diploid of EG123 (MATα leu2-3,112 ura3-52trp1his4canI$^r$; Kyung and Levin, 1992, Mol. Cel. Biol. 12: 172–182) according to the method of Elbe (1992, Biotechniques: 13: 18–19). Briefly, strain 1788 was grown on YPD (1% yeast extract, 2% peptone, 2% dextrose; Sherman et al., methods in yeast genetics, Cold Spring Harbor Laboratory Press) at 30° C. for 1 day. The strain was then transformed with plasmids pM1830 and pM1830OleoGUS. Transformants were selected on synthetic media (SC, Sherman et al. Methods in yeast genetics, Cold Spring Harbor Laboratory Press), lacking leucine at 30° C. for 3 days. Individual colonies were grown in SC (minus leucine) for 1 day, reinoculated into fresh medium at equal starting densities ($OD_{600}$=0.05), then grown to mid-log phase ($OD_{600}$)=2.0–3.0). Cultures were centrifuged at 41,000 rpm for 5 min and the supernatant was removed. The pellet was resuspended in 100 mM Tris-Cl (pH 7.5), 1 mM PMSF (phenyl methyl sulphonyl fluoride) and the cells were lysed using a French Press. GUS activity measurements were done according to Jefferson (1987) and protein determination was done as described by Bradford et al. (1976, Anal. Biochem. 72: 248–254).

Western blotting using a polyclonal anti-oleosin antibody revealed the presence of a 90 kDa polypeptide, which is in agreement with the molecular weight deduced from the amino acid sequence of the fusion protein (89.7 kDa). No cross-reactivity was observed in extracts from the untransformed strain or in extract transformed with the control plasmid pM1830. Significant GUS activity could be detected in *S. cerevisiae* cells transformed with pM1830OleoGUS, while no appriciable levels of GUS activity were measured in untransformed cells or cells transformed with pM1830 (table VIII).

Example 20
Isolation of an Arabidopsis Caleosin Gene

An Arabidopsis silique cDNA library CD4–12 was obtained from the Arabidopsis Biological Resource Centre (ABRC, http://aims.cps.msu.edu) Arabidopsis stock centre and used as a template for the isolation of the caleosin gene from Arabidopsis. For the isolation of the caleosin gene the following primers were synthesized:

GVR979:
5' TA<u>CCATGGG</u>GTCAAAGACGGAG 3'   (SEQ ID NO.32)

The sequence of the caleosin identical to the 5' end of the Arabidopsis caleosin gene (as reported in the EMBL, Genbank and DDBJ Nucleotide Sequence Database under the accession number AF067857), is indicated in bold. Underlined is an NcoI restriction site to facilitate cloning.

GVR980:
5' AT<u>CCATGG</u>CGTAGTATGCTGTCTTGTCT 3'   (SEQ ID NO.33)

The sequence complementary to the 3' end of the caleosin is indicated in bold. Underlined is an NcoI restriction site to facilitate cloning.

A Polymerase Chain Reaction (PCR) was carried out using GVR979 and GVR980 as primers and the cDNA library CD4–12 as a template. Note that this PCR has eliminated the stopcodon. This stopcodon is now replaced by an NcoI restriction site which will allow for an in-frame fusion with the GUS sequence (See example 21). The resulted PCR fragment was isolated, cloned into pBluescript (Strategene) and sequenced. The sequence of the PCR fragment and a comparison of this sequence with the published caleosin is shown in FIG. 9. The isolated sequence encoding caleosin was identical to coding sequence of the reported caleosin gene accession number AF067857 except for one nucleotide at position 69 (See FIG. 9). This nucleotide change did not result in an change in the deduced aminoacid sequence. The pBluescript vector containing the caleosin gene is called pSBS2099.

Example 21
Construction of a Plant Expression Vectors

Construction of Plant Transformation Vector pSBS2098.

Figure 13:
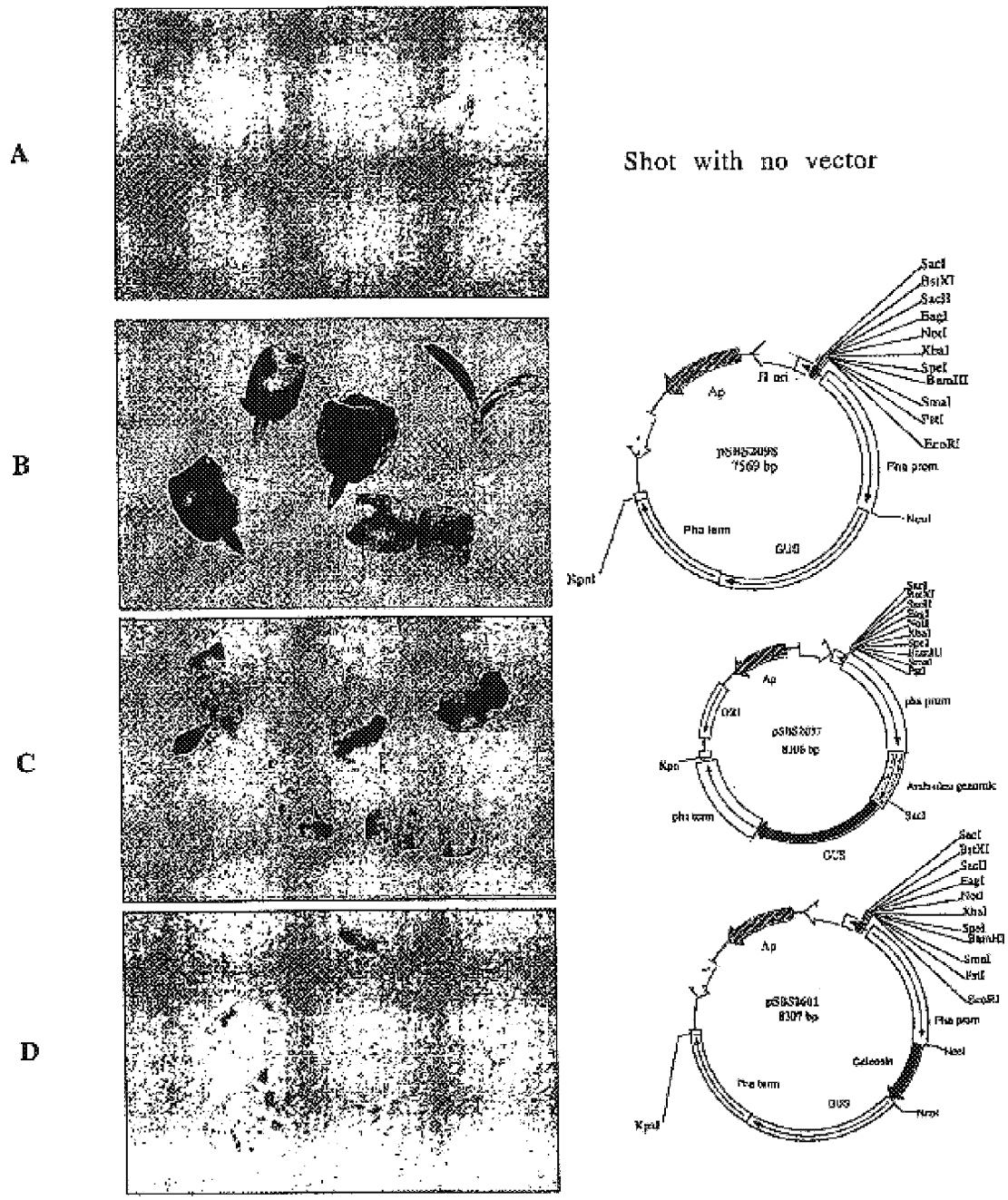
FIGS. 13A–13D. Histochemical staining of β-Glucuronidase (GUS) activity in flax embryos bombarded with vectors pBluescriptIIKS+ (negative control), pSBS2098 (GUS) pSBS2037 (oleosinGUS), and pSBS2601 (caleosinGUS).

An expression vector was constructed to allow for the seed specific expression of β-glucuronidase (GUS) in seeds. The β-glucuronidase gene was obtained from the plasmid pGUSN358S (Clontech laboratories). Standard molecular biology laboratory techniques (see e.g.: Sambrook et al. (1990) Molecular Cloning, $2^{nd}$ ed. Cold Spring Harbor Press) were used to place the GUS gene between the phaseolin promoter and the phaseolin terminator derived from the common bean *Phaseolus vulgaris* (Slightom et al (1983) Proc. Natl Acad Sc USA 80: 1897–1901; Sengupta-Gopalan et al., (1985) PNAS USA 82: 3320–3324. Standard molecular biology laboratory techniques (see e.g.: Sambrook et al. (1990) Molecular Cloning, $2^{nd}$ ed. Cold Spring Harbor Press) were also used to furnish the phaseolin terminator with a KpnI site using the Polymerase Chain reaction (PCR) (see FIG. 10). The phaseolin promoter contains a native EcoRI site at its 5' site. This EcoRI-phaseolin promoter—GUS—phaseolin terminator-KpnI sequence was cloned in the EcoRI-KpnI sites of cloned into pBluescript (Strategene). This vector was called pSBS2098. A map of pSBS2098 is shown in FIG. 13. The complete sequence of the insert of pSBS2098 is shown in FIG. 10.

Construction of Plant Transformation Vector pSBS2037

An expression vector was constructed to allow for the seed specific expression of a oleosin-β-glucuronidase (oleosinGUS) fusion in seeds. An Arabidopsis oleosin gene as described Van Rooijen et al (1992) Plant Mol. Biol.18:

1177–1179) was placed upstream and in-frame (again the native stop codon was removed) to the GUS coding sequence of pSBS2099 using standard molecular biology laboratory techniques (see e.g.: Sambrook et al. (1990) Molecular Cloning, $2^{nd}$ ed. Cold Spring Harbor Press). This vector was called pSBS2037. A map of pSBS2037 is shown in FIG. 13 and the complete sequence of the insert of pSBS2037 is shown in FIG. 11.

Construction of Plant Transformation Vector pSBS2601.

An expression vector was constructed to allow for the seed specific expression of a caleosin-β-Glucuronidase (caleosinGUS) translational fusion in seeds.

The Arabidopsis caleosin gene as described in Example 20 was cloned as an NcoI fragment upstream (and in-frame) of the GUS coding This vector was called pSBS2601. A map of pSBS2601 is shown in FIG. 13 and the complete sequence of the insert of pSBS2061 is shown in FIG. 12.

EXAMPLE 22

Transient Expression of β-glucuronidase, Oleosin-β-glucuronidase and Caleosin-β-glucuronidase in Flax Embryos Expression vectors pSBS2037, pSBS2098 and pSBS2601 were tested for their ability to transiently express GUS, oleosinGUS and caleosinGUS respectively. This transient expression was carried out bombarding flax embryos. As a control flax embryos were bombarded with gold particles with no DNA added. The subcellular location of the "free" GUS (as a result of transient expression of pSBS2098) the oleosinGUS fusion (as a result of expression of pSBS2037) and the caleosinGUS (as a result of expression of pSBS2601), and histochemical staining was determined/done essentially as described in Abenes, et al (1997) Plant Cell reports 17:1–7, with several minor modifications. In brief, the protocol was as follows: Three plates with 10 embryos each were separately bombarded with each plasmid (or just gold particles for the control). After particle bombardment one plate was used for histochemical staining (see FIG. 13) and the embryos from the two remaining plates were combined for activity measurements. These were ground in 200 μl oilbody extraction buffer (5 mM Tris-Cl pH 7.5, 0.4 M sucrose, 500 mM NaCl). An aliquot was taken, this sample is referred to as "Total extract". The remainder is spun in an eppendorf microfuge at 15,000× g, resulting in a supernatant fraction of 150 μl and an oilbody fraction. The oilbody fraction is resuspended in 150 μl. 10 μl of total extract, supernatant and oilbody fraction are added to 100 μl GUS assay buffer (see Jefferson R A (1987) Assaying chimeric genes in plants: The GUS gene fusion system. Plant Mol Biol Rep 5: 387–405). This is done in duplicate. The reaction is incubated at 37° C. for 2 hours after which 20 μl of this reaction is added to 1 ml 0.2 M Sodium Carbonate (Stop buffer). Fluorescence is measured according to Jefferson R A (1987). Plant Mol Biol Rep 5: 387–405. As can be seen in FIG. 13, GUS expression is visible in panel B, C and D. This means that both oleosinGUS (panel C) and caleosinGUS (panel D) fusion proteins are expressed and result in a biologically active enzyme. Table IX shows the result of the GUS activity measurements. As can be seen from this table, both the "free" GUS, oleosinGUS and caleosinGUS are expressed. The "free" GUS is predominantly found in the supernatant fraction, whereas oleosinGUS and caleosinGUS are predominantly found in the oilbody fraction. This indicates that both oleosin and caleosin sequences are sufficient for the efficient targeting to oilbodies.

Additional Applications of the Invention

The above examples describe various proteins that can be fused to an oil body protein and expressed in oil bodies in plants, bacteria and yeast. The above also provides the methodology to prepare such transgenic plants. Therefore one skilled in the art can readily modify the above in order to prepare fusion proteins containing any desired protein or polypeptide fused to an oil body protein in a variety of host systems. Several examples of other applications of the present invention are provided below.

a) Construction of an Oleosin/Single Chain Antibody Fusion Protein.

As a further example of the invention, an antibody may be expressed in *B. napus*. Prior to the construction of an oleosin gene fusion, the deduced amino acid sequence of the coding region for the antibody may be back-translated using a *B. napus* codon usage table derived from several known *B. napus* genes and 'inside-out' recursive PCR (Prodomou & Pearl, 1992, Protein Eng. 5: 827–829) and yielding a synthetic scFv gene.

Gene fusion between the oleosin gene and the antibody gene can be accomplished by joining the synthetic antibody gene to the 5' end of the oleosin gene in a plasmid using cloning strategies well known to a person skilled in the art and similar to those outlined in the subject application in e.g. examples 9 to 11. The insert from the plasmid may be cloned into the binary vector pCGN1559 and used to transform *A. tumefaciens*. Cotelydonary petioles of *B. napus* may be transformed with the recombinant binary vector as described in Moloney et al. (1989, Plant Cell Reports, 8: 238–242).

Oil body extracts from transgenic *B. napus* plants may analysed by Western blotting using an anti oleosin antibody for the presence of the fusion protein.

b) Combination of Two Oleosin Fusion Proteins to Release a Protein Product from Oil Bodies.

Two different oil body protein fusions associated with oil bodies can be used as a means to obtain a final product. For example, a transgenic *B. napus* may be obtained which contains a gene that comprises the GUS enzyme fused to the 3' coding sequence of oleosin separated by a collagenase protease recognition site. Oil bodies may be obtained from the seed of this plant. These oil bodies can be mixed with the oil bodies described above, which contains collagenase fused to oleosin. The collagenase activity of the oleosin/collagenase fusion protein oil bodies can release the GUS enzyme from the oleosin/GUS fusion proteins oil bodies. The GUS enzyme remains in the aqueous phase after removal of the oil bodies. No collagenase enzyme or contaminating oleosins will remain associated with the purified GUS enzyme illustrating the utility of the invention in obtaining easily purified proteins.

c) Expression of a Oleosin/Phytase fusion protein in *B. napus*.

A microbial phytase from a Aspergillus may be isolated based on the published sequence (van Gorcom et al, European Patent Application 90202565.9, publication number 0 420 358 A1). This gene can be fused to the carboxy terminus of the oleosin protein using techniques described above and a collagenase recognition protease cleave site may be included to allow for separation of the phytase from the oil body if desired. The construct may contain, in the following order, the promoter region of the Arabidopsis oleosin gene, the coding sequence of the oleosin protein including the intron, a collagenase cleavage site and the phytase gene followed by the nos terminator polyadenylation signal. The construct can be inserted into the binary plasmid Bin 19 and the resultant plasmid introduced into Agrobacterium. The resulting strain can be used to transform *B. napus*. The seed of the transgenic plants will contain phytase activity. The phytase activity will be associated with the oil body fraction.

The phytase activity is useful for the enhancement of meal for monogastric animal feed. The phytase may be purified by treatment with collagenase as described in a), or the transgenic seed may be used as a feed additive.

d) Expression of a Oleosin/Glucose Isomerase.

The enzyme glucose isomerase can be expressed as a oleosin fusion protein by joining the coding sequence for the enzyme, (for example, described by Wilhelm Hollenberg, 1985, Nucl. Acid. Res. 13:5717–5722) to the oleosin protein as described above. The construct may be used to transform *B. napus*.

e) Expression of a Oleosin/High Lysine Fusion Protein.

In order to increase the lysine content of transgenic seeds, a polylysine oligonucleotide may be added to the 3' coding region of the oleosin gene. For example, a repetitive oligonucleotide encoding a polylysine coding sequence can be made by synthesizing a $(AAG)_{20}$ oligonucleotide that is joined to the 3' coding region of the oleosin gene by replacement of the hirudin coding sequence contained within pCBOGHIRT plasmid described above in example 8 with the polylysine oligonucleotide through the use of cohesive restriction termini. The construct may contain, in the following order, the promoter region of the Arabidopsis oleosin gene, the coding sequence of the oleosin protein including the intron, 20 codons for the amino acid lysine followed by the nos terminator polyadenylation signal. The construct may be inserted into the binary plasmid Bin 19 and the resultant plasmid may be introduced into the Agrobacterium. The resulting strain can be used to transform *B. napus*.

f) Expression of an Fungicidal Protein as an Oleosin Fusion Protein.

As a further example of the invention, a oleosin fusion protein may be constructed which encodes a protein that is toxic to fungi. For example, the gene for the enzyme chitinase isolated from tobacco (Melchers et al, 1994, Plant Journal 5:469–480) may be fused to the 3' coding region of oleosin under the control of the native oleosin promoter. Included in this construct may be an oligonucleotide that encodes a collagenase recognition site located between the oleosin and chitinase coding regions. The expression of this construct will result in the production of a oleosin/chitinase fusion protein from which the chitinase enzyme can be released from the oleosin by treatment with collagenase. To this construct may be added a second chimeric gene capable of expression of a collagenase enzyme during seed germination. This second gene can comprise approximately 1.5 Kb of the 5' promoter region for isocitrate lyase, the collagenase coding sequence of *Vibrio alginolyticus* (Takeuchi et al., 1992, Biochemical Journal, 281:703–708) and the nos terminator. Isocitrate lyase is a glyoxysomal enzyme expressed under transcriptional control during early stages of seed germination (Comai et al., 1989, The Plant Cell, 1:293–300). This second construct therefore will express collagenase during the germination of the seed and mobilization of the oil body reserves. Expression of isocitrate lyase is restricted to germination and is not expressed in developing seeds. This second gene, joined to the oleosin/chitinase gene can be inserted into the binary vector Bin 19. The resultant vector may be introduced into Agrobacterium and used to transform *Brassica napus* plants. It is noted that the two genes may also be introduced independently or in two different plants which are then combined through sexual crossing. Seed from transgenic plants would be collected and tested for resistance to fungi.

g) Expression of an Oleosin Fusion Protein that Provides Protection from Insect Predation.

As a further example of the invention, a fusion oleosin protein may be constructed which encodes a protein toxic to foraging insects. For example, the gene for cowpea trypsin inhibitor (Hilder et al., 1987, Nature, 330:160–163) may be used to replace the chitinase gene described in e). The expression of this construct will result in the production of a oleosin/trypsin inhibitor fusion protein from which the trypsin inhibitor can be released from the oleosin by treatment with collagenase. By replacement of the chitinase gene in e) with the trypsin inhibitor, the construct also contains the collagenase gene under control of the germination specific promoter from the isocitrate lyase gene. This construct may be inserted into the binary vector Bin19. The resultant vector can be introduced into Agrobacterium and used to transform *Brassica napus* plants. Seed from transgenic plants were collected and tested for resistance to insect predation.

h) Expression of an Enzyme to Alter Secondary Metabolites in Seeds.

In order to alter specific secondary metabolites in the seed, an enzyme encoding tryptophan decarboxylase (TDC) can be expressed in the seed as a fusion to oleosin. This particular enzyme (DeLuca et al., 1989, Proc. Natl. Acad. Sci. USA, 86:2582–2586), redirects tryptophan into tryptamine and causes a depletion of tryptophan derived glucosinolates. This lowers the amount of the antinutritional glucosinolates in the seed and provides a means to further reduce glucosinolate production in crucifer plant species. To accomplish this, a fusion protein may be constructed between the TDC gene and the oleosin coding region. The construct may contain, in the following order, the promoter region of the Arabidopsis oleosin gene, the coding sequence of the oleosin protein including the intron, the TDC gene followed by the nos terminator polyadenylation signal. The construct may be inserted into the binary plasmid Bin 19 and the resultant plasmid introduced into Agrobacterium. The resulting strain can be used to transform *B. napus*.

i) Expression of Heterologous Proteins in Mammalian Cells.

The oil body protein—heterologous protein fusion may also be prepared in mammalian host cells. For example, an oleosin/GUS fusion may be inserted into a mammalian expression vector and introduced into mammalian cells as described below.

Expression of an oleosin/GUS fusion in mammalian cells would require the cloning of the GUS gene as described in example 17 in commercially available mammalian expression vectors. For example, mammalian expression vectors pMSG, pSVL SV40, pCH 110, (all available from Pharmacia code No. 27-4506-01, 27-4509-01 and 27-4508-1 respectively) may be used. The oleosin/GUS fusion gene may be fused in the plasmid. These plasmids can be introduced into mammalian cells using established protocols (See e.g. Introduction of DNA into mammalian cells (1995) Current Protocols in Molecular Biology, Ausubel et al. (ed) Supplement 29, Section 9). Accumulation of the oleosin/GUS transcript in mammalian cells can be determined after preparation of mammalian cell RNA (See e.g. Direct analysis of RNA after transfection (1995) Current Protocols in Molecular Biology, Ausubel et al. (ed) Supplement 29, Section 9.8), northern blotting, and hybridization of this northern blot to a $^{32}P$ labelled Brassica oleosin cDNA as described in Example 18. After preparation of a total protein extract from the transfected mammalian cell culture, GUS activity can be measured, demonstrating the accumulation of the oleosin/GUS protein. Alternatively, immunoblotting can be performed on this protein extract using commercially available GUS antibodies and/or oleosin antibodies.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE I

Expression of Arabidopsis oleosin chimearic promoter constructs in transgenic Brassica napus.

| Promoter Construct | Expression of GUS Activity (pmol/MU/mg protein/min) | | | | |
|---|---|---|---|---|---|
| (GUS fusion) | Early Seed (torpedo) | Root | Leaf | Stem | Late Seed (cotyledon) |
| 2500 | 7709 | 444 | 47 | 88 | 11607 |
| 1200 | 1795 | — | — | — | 8980 |
| 800 | 475 | — | — | — | 7130 |
| 600 | 144 | — | — | — | 1365 |
| 200 | 65 | 260 | 6 | 26 | 11 |
| control | 14 | 300 | 6 | 30 | 14 |

Oleosin promoter-GUS fusions were constructed as described in example 3. Included are GUS values obtained from a control non-transformed plant. A (−) indicated the tissue was not tested. Units are picomoles of methyl umbelliferone (producct) per mg protein per minute.

TABLE II

Expression of Arabidopsis oleosin chimearic promoter constructs in transgenic tobacco (Nicotiana tabacum).

| Promoter Constructs (GUS fusions) | GUS Activity in Seed (pmol/MU/mg protein/min) |
|---|---|
| 2500 | 11330 |
| 800 | 10970 |
| Control | 0 |

Oleosin promoter-GUS fusions were constructed as described in example 3. Included are GUS values obtained from a control non-transformed plant. Units are picomoles of methyl umbelliferone (product) per mg protein per minute.

TABLE III

Specific partitioning of GUS/oleosin fusions into oil bodies when expressed in transgenic Brassica napus plants.

| Plant Number | Percent GUS Activity in Oil Bodies (%) | GUS Activity in Oil bodies | GUS Activity 100,000 × g Supernatant | GUS Activity in 100,000 × g Pellet |
|---|---|---|---|---|
| A1 | 88 | 493 | 1 | 67 |
| B7 | 90 | 243 | 5 | 22 |
| control | 0 | 0 | 0 | 0 |

Plants were transformed with an oleosin/GUS fusion protein under the control of the Arabidopsis oleosin promoter. Transformed seeds were obtained and fractionated. The initial fractionation consisted of grinding the seeds in 1.5 mL of buffer A consisting of 15 mM Tricine-KOH, pH 7.5, 10 mM KCl, 1 mM Mg $Cl_2$, 1 mM EDTA, 100 mM sucrose followed by centrifugation at 14,000× g for 15 minutes at 4° C. From this three fractions were obtained consisting of a floating oil body layer, an aqueous layer and a pellet. The oil body fraction was recovered and assayed for GUS activity. The remaining aqueous phase was further centrifuged for 2 hours at 100,000× g. The pellet and supernatant from this centrifugation was also tested for GUS activity. Units are nmol MU per mg protein per min.

TABLE IV

Cleavage of GUS enzyme from oleosin/GUS fusions associated with oil bodies derived from transgenic Brassica napus containing an oleosin/GUS fusion protein.

| | GUS Activity (nmol product/mg protein/min) | | |
|---|---|---|---|
| Fraction | Before Cleavage | After Cleavage | % Activity |
| Oil bodies | 113 | 26.4 | 24 |
| 100,000 × g supernatant | 14.3 | 83.6 | 76 |
| 100,000 × g pellet | 15.7 | — | — |

Oil bodies containing an oleosin/GUS fusion protein were subjected to cleavage using the endopeptidase thrombin as described in example 5. Values shown are GUS activities before and after cleavage with thrombin. The values are also expressed as a percentage of total GUS activity released following enzyme fusion. Units are nmol methyl umbelliferone per mg protein/min.

TABLE V

Reuse of oil body associated enzymatic activities.

| | % GUS Activity | |
|---|---|---|
| # Times Oil Bodies Washed | Oil bodies | Supernatant |
| 1 | 100 | 8 ± 5 |
| 2 | 118 ± 7 | 5 ± 3 |
| 3 | 115 ± 8 | 3 ± 4 |
| 4 | 119 ± 8 | 1 ± 20 |

Oil bodies containing an oleosin/GUS protein were isolated from the seeds of transgenic Brassica napus. The oil bodies were added to the fluorometric GUS substrate MUG and allowed to react for one hour. The oil bodies were then recovered and added to a new tube containing the substrate and allowed to react for one hour again. This process was repeated a total of four times. The table illustrates the reusable activity of the GUS enzyme while still associated with the oil bodies. Values are normalized to 100% as the GUS activity of original oil body isolates.

TABLE VI

Recovery of active hirudin following synthesis of hirudin in plant seeds.

| Treatment | Thrombin Units Per Assay | Antithrombin Units per mg Oil Body Proteins |
|---|---|---|
| Buffer only | 0.143 | 0 |
| Wild-type seed | 0.146 | 0 |
| Wild-type seed + factor Xa | 0.140 | <0.001 |
| Transformed (uncut) | 0.140 | <0.001 |
| Transformed + factor Xa | 0.0065 | 0.55 |

Oil bodies containing a hirudin/GUS fusion protein were isolated according to the method and treated with the endoprotease Factor Xa inhibition assay using N-p tosyl-gly-pro-arg-p-nitro anilide (Sigma). Hirudin activity was measured by the use of a thrombin in the method of Dodt et al (1984, FEBS Lett. 65, 180–183). Hirudin activity is expressed as thrombin units per assay in presence of 255 μg of oil body proteins, and also as antithrombin units per mg oil body protein.

As described in example 22, oleosin/GUS fusions were expressed in E. coli. Cells were grown, induced with ITPG and GUS activity measured.

TABLE VII

Expression of active oleosin/GUS fusions in E. coli.

| Plasmid | Gus Activity |
| --- | --- |
| pKK233–2 | 2.5 |
| pKKoeloGUS | 3.1 |
| pKKoleoGUS | 28.1 |
| pkkGUS | 118.2 |

TABLE VIII

GUS activity of total extracts of untransformed S. Cerevisiae strain 1788, transformed with M1830 and M1830oleoGUS

| S. Cerevisiae strain 1788 | Specific Activity (pmol MU.min$^{-1}$.μg prot$^{-1}$) |
| --- | --- |
| untransformed | 0.001 |
| transformed with M1830 | 0.001 |
| Transformed with M1830 OleosinGUS | 41.3 |

TABLE IX

Transient GUS activity as a result of bombardment with plasmids pSBS2037, pSBS2098 and pSBS2601. The percentage of oilbody targeting was calculated as follows: (GUS activity on oibodies) / (GUS activity on oilbodies + GUS activity in supernatant)) × 100%. As indicated in the text every experiment was done in duplicate.

| | Plasmid used | protein produced | Activity nmol/l MU produced in cuvet | Activity minus control | % targeting to oil body |
| --- | --- | --- | --- | --- | --- |
| Total extract | no plasmid | | 72 | — | |
| Total extract | no plasmid | | 55 | — | |
| Total extract | 2037 | oleosinGUS | 394 | 294.5 | |
| Total extract | 2037 | oleosinGUS | 457 | 357.5 | |
| Total extract | 2098 | GUS | 1561 | 1461.5 | |
| Total extract | 2098 | GUS | 1728 | 1628.5 | |
| Total extract | 2061 | caleosinGUS | 217 | 117.5 | |
| Total extract | 2061 | caleosinGUS | 170 | 70.5 | |
| supernatant | no plasmid | | 58 | — | |
| supernatant | no plasmid | | 56 | — | |
| supernatant | 2037 | oleosinGUS | 66 | 9.0 | |
| supernatant | 2037 | oleosinGUS | 65 | 8.0 | |
| supernatant | 2098 | GUS | 799 | 742.0 | |
| supernatant | 2098 | GUS | 1356 | 1299.0 | |
| supernatant | 2061 | caleosinGUS | 61 | 4.0 | |
| supernatant | 2061 | caleosinGUS | 64 | 7.0 | |
| oilbody | no plasmid | | 50 | — | |
| oilbody | no plasmid | | 46 | — | |
| oilbody | 2037 | oleosinGUS | 203 | 145 | 94 |
| oilbody | 2037 | oleosinGUS | 244 | 186 | 96 |
| oilbody | 2098 | GUS | 94 | 36 | 5 |
| oilbody | 2098 | GUS | 103 | 45 | 3 |
| oilbody | 2061 | caleosinGUS | 98 | 40 | 91 |
| oilbody | 2061 | caleosinGUS | 102 | 44 | 86 |

We claim:

1. A method for the expression of a heterologous polypeptide by a plant host cell said method comprising:
   a) introducing into a plant host cell a chimeric nucleic acid sequence comprising:
      1) a first nucleic acid sequence capable of regulating the transcription in said host cell of
      2) a second nucleic acid sequence, wherein said second sequence encodes a fusion polypeptide and comprises (i) a nucleic acid sequence encoding a sufficient portion of a plant oil body protein gene to provide targeting of the fusion polypeptide to a lipid phase linked in reading frame to (ii) a nucleic acid sequence encoding the heterologous polypeptide; and
      3) a third nucleic acid sequence encoding a termination region functional in the host cell; and
   b) growing said host cell to produce the fusion polypeptide.

2. The method according to claim 1 further including separating the recombinant fusion polypeptide from cellular host cell components by selective partitioning into a lipid phase.

3. The method according to claim 2 wherein said selective partitioning comprises centrifugation, floatation or size exclusion.

4. The method according to claim 1 further including separating the recombinant fusion polypeptide from cellular host components by selective partitioning into a lipid phase comprising oil bodies.

5. The method according to claim 4 wherein said recombinant fusion polypeptide is separated by addition of oil body components and reconstitution of the oil bodies.

6. The method according to claim 2 further comprising releasing the heterologous polypeptide from the fusion polypeptide associated with the lipid phase, said method comprising:
   c) including in said second nucleic acid sequence (2) between said nucleic acid sequence (i) encoding the oil body protein and the nucleic acid sequence (ii) encoding the heterologous polypeptide, a linker nucleic acid sequence (iii) encoding an amino acid sequence that is specifically cleavable by enzymatic or chemical means; and
   d) contacting the lipid phase with said enzymatic or chemical means such that said heterologous polypeptide is released from the fusion polypeptide.

7. The method according to claim 6 wherein said linker nucleic acid sequence encodes an amino acid sequence that is recognizable by the proteolytic action of an enzyme selected from the group consisting of thrombin, factor Xa, collagenase, chymosin, clostrapain and viral protease.

8. The method according to claim 6 wherein said enzymatic means comprises an enzyme that is immobilized.

9. The method according to claim 8 wherein said enzyme is immobilized by attachment to an oil body protein that is associated with an oil body.

10. The method according to claim 1 wherein said recombinant polypeptide is an enzyme.

11. The method according to claim 10 wherein said recombinant polypeptide is an enzyme that retains its enzymatic properties while part of the fusion polypeptide is associated with the oil body.

12. A method for producing an altered seed meal by producing a heterologous polypeptide in association with a plant seed oil body fraction, said method comprising:
   a) introducing into a plant cell a chimeric nucleic acid sequence comprising:
      1) a first nucleic acid sequence capable of regulating the transcription in said plant cell of
      2) a second nucleic acid sequence wherein said second sequence encodes a fusion polypeptide and comprises (i) a nucleic acid sequence encoding a sufficient portion of a plant oil body protein gene to provide targeting of the fusion polypeptide to an oil body, linked in reading frame to (ii) a nucleic acid sequence encoding the heterologous polypeptide and
      3) a third nucleic acid sequence encoding a termination region;
   b) regenerating a plant from said plant cell and growing said plant to produce seed whereby said heterologous polypeptide is expressed and associated with oil bodies; and
   c) crushing said seed and preparing an altered seed meal.

13. The method according to claim 1 wherein said heterologous polypeptide is selected from the group consisting of antibodies, glycanases, hormones, proteases, protease inhibitors and seed storage proteins.

14. The method according to claim 1 wherein said heterologous polypeptide is selected from the group consisting of a thrombin inhibitor, hirudin, an interleukin, chymosin, cystatin, xylanase, carp growth hormone, zein, an antibody and a collagenase.

15. The method according to claim 1 wherein said plant is dicotyledonous.

16. The method according to claim 1 wherein said plant is monocotyledenous.

17. The method according to claim 1 wherein said plant is from the family Brassicaceae, Compositae, Euphorbiaceae, Leguminosae, Linaceae, Malvaceae, Umbilliferae or Graminae.

18. The method according to claim 17 wherein said plant is from the species *Brassica napus* (canola), *Helianthus anuus* (sunflower), *Carthamus tinctorius* (safflower), *Glycine max* (soybean), *Ricinus communis* (castor bean), *Linum usitatissimum* (flax), *Gossypium hirsutum* (cotton), *Coriandrum sativum* (coriander) or *Zea mays* (corn).

19. A method according to claim 1 wherein said oil body protein gene is an oleosin or a caleosin.

20. A method for the expression of a heterologous polypeptide by a plant host cell said method comprising:
   a) generating by homologous recombination into a plant host cell a chimeric nucleic acid sequence comprising:
      1) a first nucleic acid sequence capable of regulating transcription in said host cell
      2) a second nucleic acid sequence, wherein said second sequence encodes a fusion polypeptide and comprises (i) a nucleic acid sequence encoding a sufficient amount of a plant oil body protein gene to provide targeting of the fusion polypeptide to a lipid phase, linked in reading frame to (ii) a nucleic acid sequence encoding the heterologous polypeptide; and
      3) a third nucleic acid sequence encoding a termination region functional in the host cell; and
   b) growing said host cell to produce the heterologous polypeptide.

21. A chimeric nucleic acid sequence, capable of being expressed in association with an oil body of a plant host cell comprising:
   1) a first nucleic acid sequence capable of regulating the transcription in said host cell of
   2) a second nucleic acid sequence, wherein said second sequence encodes a fusion polypeptide and comprises (i) a nucleic acid sequence encoding a sufficient portion of a plant oil body protein gene to provide targeting of the fusion polypeptide to a lipid phase linked in reading frame to (ii) a nucleic acid sequence encoding the heterologous polypeptide; and
   3) a third nucleic acid sequence encoding a termination region functional in the host cell.

22. The chimeric nucleic acid sequence according to claim 21 wherein said nucleic acid sequence (ii) encodes an enzyme.

23. The chimeric nucleic acid sequence according to claim 21 further including (iii) a linker nucleic acid sequence encoding an amino acid sequence that is specifically cleavable by enzymatic means wherein said linker nucleic acid sequence (iii) is located between said (i) nucleic acid sequence encoding the oil body protein and said (ii) nucleic acid sequence encoding the heterologous polypeptide.

24. The chimeric nucleic acid according to claim 23 wherein said linker nucleic acid sequence (iii) encodes a cleavage site for an enzyme selected from the group consisting of thrombin, factor Xa, collagenase chymosin and viral protease.

25. A chimeric nucleic acid sequence according to claim 21 wherein said oil body protein gene is an oleosin or a caleosin.

26. An expression cassette comprising a chimeric nucleic acid sequence according to claim 21.

27. A plant transformed with a chimeric nucleic acid sequence according to claim 21.

28. A plant cell culture containing a chimeric nucleic acid sequence according to claim 21.

29. A plant seed containing a chimeric nucleic acid sequence according to claim 21.

* * * * *